US009101572B2

(12) United States Patent
Pushko et al.

(10) Patent No.: US 9,101,572 B2

(45) Date of Patent: Aug. 11, 2015

(54) INFECTIOUS DNA VACCINES AGAINST CHIKUNGUNYA VIRUS

(75) Inventors: Peter Pushko, Frederick, MD (US); Irina Tretyakova, Frederick, MD (US); Igor Lukashevich, Louisville, KY (US)

(73) Assignee: MEDIGEN, INC., Frederick, MD (US)

( * ) Notice: Subject to any disclaimer, the term of this patent is extended or adjusted under 35 U.S.C. 154(b) by 0 days.

(21) Appl. No.: 13/519,948

(22) PCT Filed: Jan. 3, 2011

(86) PCT No.: PCT/US2011/000001

§ 371 (c)(1), (2), (4) Date: Nov. 7, 2012

(87) PCT Pub. No.: WO2011/082388

PCT Pub. Date: Jul. 7, 2011

(65) Prior Publication Data

US 2013/0052225 A1 Feb. 28, 2013

Related U.S. Application Data

(60) Provisional application No. 61/291,682, filed on Dec. 31, 2009.

(51) Int. Cl.

*A61K 39/12* (2006.01)
*C07K 14/005* (2006.01)
*A61K 39/00* (2006.01)

(52) U.S. Cl.

CPC ............... *A61K 39/12* (2013.01); *C07K 14/005* (2013.01); *A61K 2039/53* (2013.01); *C12N 2770/36122* (2013.01); *C12N 2770/36134* (2013.01)

(58) Field of Classification Search

None

See application file for complete search history.

(56) References Cited

U.S. PATENT DOCUMENTS

| | | | | |
|---|---|---|---|---|
| 5,789,245 | A | 8/1998 | Dubensky, Jr. et al. | |
| 6,015,686 | A | 1/2000 | Dubensky, Jr. et al. | |
| 6,296,854 | B1 | 10/2001 | Pushko et al. | |
| 2006/0099587 | A1 * | 5/2006 | Johnston et al. | 435/6 |
| 2008/0260775 | A1 | 10/2008 | Johnston et al. | |
| 2013/0022631 | A1 * | 1/2013 | Ella et al. | 424/186.1 |

FOREIGN PATENT DOCUMENTS

| | | | | |
|---|---|---|---|---|
| KR | 10-2008-0003989 | A | 1/2008 |
| WO | 2004/055161 | A2 | 7/2004 |
| WO | 2008/030220 | A2 | 3/2008 |
| WO | 2009/048633 | A2 | 4/2009 |

OTHER PUBLICATIONS

Nougairede et al., Random Codon Re-encoding Induces Stable Reduction of Replicative Fitness of Chikungunya Virus in Primate and Mosquito Cells, 2013, PLOS Pathogens, vol. 9, No. 2, pp. 1-18.*

Tsetsarkin et al., Research Paper Infectious Clones of Chikungunya Virus (La Rèunion Isolate) for Vector Competence Studies, 2006, Vector-Borne and Zoonotic Diseases, vol. 6, No. 4, pp. 325-337.*

Invitrogen, pcDNA3.1(+) pcDNA3.1(−): Catalog Nos. V790-20 and V795-20, 2001, Retrieved from the Internet: http://www.pcr.cn/download.asp?filename=V790-20%20V795-20%20pcdna3.1_man.pdf&dl_id=27, Accessed May 6, 2011.

L37661.3, Chikungunya virus strain TSI-GSD-218, complete genome, GenBank, Feb. 28, 2007, Retrieved from the Internet: http://www.ncbi.nlm.nih.gov/nuccore/L37661, Accessed May 6, 2011.

International Search Report issued on Jun. 16, 2011 by the U. S. Patent and Trademark Office as the International Searching Authority in International Patent Application No. PCT/US11/000001.

Wang et al., "Chimeric alphavirus vaccine candidates for chikungunya", Vaccine, 2008, Sep. 15, pp. 5030-5039, vol. 26.

Edelman et al., "Phase II safety and immunogenicity study of live chikungunya virus vaccine TSI-GSD-218", American Journal of Tropical Medicine & Hygiene, Jun. 1, 2000, pp. 681-685, vol. 62.

Berglund et al., "Enhancing immune responses using suicidal DNA vaccines", Nature Biotechnology, Jun. 1, 1998, pp. 562-565, vol. 16.

L37661.3, Chikungunya virus strain TSI-GSD-218, complete genome, GenBank, created Jan. 4, 1995, last updated Mar. 1, 2007.

Supplementary European Search Report issued on Jun. 21, 2013 by the European Patent Office in corresponding European Application No. 11728540.

* cited by examiner

*Primary Examiner* — Benjamin P Blumel

(74) *Attorney, Agent, or Firm* — Dentons US LLP

(57) ABSTRACT

Described herein are i-DNA™ vectors and vaccines and methods for using the same. The i-DNA™ generates live attenuated vaccines in eukaryotic cells in vitro or in vivo for pathogenic RNA viruses, particularly chikungunya virus (CHIKV). When iDNA is injected into the vaccine recipient, RNA of live attenuated virus is generated by in vivo transcription in the recipient's tissues. This initiates production of progeny attenuated viruses in the tissues of the vaccine recipient, as well as elicitation of an effective immune response protecting against wild-type, non-attenuated virus.

30 Claims, 36 Drawing Sheets

Figure 1.

| Vaccine Requirements | Live Attenuated Vaccines | DNA Vaccines | CHIKV i- DNA Vaccine |
|---|---|---|---|
| Genetic Stability | No | Yes | Yes |
| Simple Manufacturing | No | Yes | Yes |
| Inexpensive | No | Yes | Yes |
| Cold Chain Not Required | No | Yes | Yes |
| High Purity | No | Yes | Yes |
| Single Dose Vaccination | Yes | No | Yes |
| Nuclear Involvement is Minimal | Yes | No | Yes |
| Rapid Onset of Immunity | Yes | No | Yes |
| Effective Protection | Yes | No | Yes |

Figures 3A-3E: The i-DNA sequence contains antigenomic ribozyme of HDV upstream from NotI site (highlighted in italics).

Figure 3A

```
   1 GGCGCGCCTG ACATTGATTA TTGACTAGTT ATTAATAGTA ATCAATTACG GGGTCATTAG
  61 TTCATAGCCC ATATATGGAG TTCCGCGTTA CATAACTTAC GGTAAATGGC CCGCCTGGCT
 121 GACCGCCCAA CGACCCCCGC CCATTGACGT CAATAATGAC GTATGTTCCC ATAGTAACGC
 181 CAATAGGGAC TTTCCATTGA CGTCAATGGG TGGAGTATTT ACGGTAAACT GCCCACTTGG
 241 CAGTACATCA AGTGTATCAT ATGCCAAGTA CGCCCCCTAT TGACGTCAAT GACGGTAAAT
 301 GGCCCGCCTG GCATTATGCC CAGTACATGA CCTTATGGGA CTTTCCTACT TGGCAGTACA
 361 TCTACGTATT AGTCATCGCT ATTACCATGG TGATGCGGTT TTGGCAGTAC ATCAATGGGC
 421 GTGGATAGCG GTTTGACTCA CGGGGATTTC CAAGTCTCCA CCCCATTGAC GTCAATGGGA
 481 GTTTGTTTTG GCACCAAAAT CAACGGGACT TTCCAAAATG TCGTAACAAC TCCGCCCCAT
 541 TGACGCAAAT GGGCGGTAGG CGTGTACGGT GGGAGGTCTA TATAAGCAGA GCTCTCTGGC
 601 TAACTAGAGa tggctgcgtg agacacacgt agcctaccag tttcttactg ctctactctg
 661 caaagcaaga gattaataac ccatcatgga ttctgtgtac gtggacatag acgctgacag
 721 cgccttttg aaggccctgc aacgtgcgta ccccatgttt gaggtggaac ctaggcaggt
 781 cacatcgaat gaccatgcta atgctagagc gttctcgcat ctagccataa aactaataga
 841 gcaggaaatt gatcccgact caaccatcct ggatataggt agtgcgccag caaggaggat
 901 gatgtcggac aggaagtacc actgcgtttg cccgatgcgc agcgcagaag atcccgagag
 961 actcgctaat tatgcgagaa agctcgcatc tgccgcagga aaagtcctgg acagaaacat
1021 ttctggaaag atcggggact tacaagcggt gatggccgtg ccagacacgg agacgccaac
1081 attttgctta cacacagatg tctcatgtag acagagagca gacgtcgcga tataccaaga
1141 cgtctatgct gtacacgcac ccacgtcgct ataccaccag gcgattaaag gagtccgagt
1201 ggcgtactgg gtagggttcg acacaacccc gttcatgtac aacgctatgg cgggtgccta
1261 cccctcatac tcgacaaatt gggcggatga gcaggtactg aaggctaaga acataggatt
1321 atgttcaaca gacctgacgg aaggtagacg aggcaaattg tctatcatga gagggaaaaa
1381 gctaaaaccg tgcgaccgtg tgctgttctc agtagggtca acgctttacc cggaaagccg
1441 cacgctactt aagagctggc acctaccatc ggtgttccat ctaaagggca agcttagctt
1501 cacatgccgc tgtgacacag tggtttcgtg tgagggctac gtcgttaaga gaataacgat
1561 gagcccaggc ctttatggaa aaaccatagg gtatgcggta acccaccacg cagacggatt
1621 cttgatgtgc aagactaccg acacggttga cggcgaaaga gtgtcattct cggtgtgcac
1681 gtacgtgccg gcgaccattt gtgatcaaat gaccggcatc cttgctacag aagtcacgcc
1741 ggaggatgca cagaagctgt tggtggggct gaaccagagg atagtggtta acggcagaac
1801 gcaacggaac acgaacacca tgaagaacta cctacttccc gtggtcgccc aggccttcag
1861 taagtgggca aaggagtgcc ggaaggacat ggaagatgag aagcttctgg gggtcagaga
1921 aagaacacta acctgctgct gtctatgggc atttaagaag cagaaaacac acacggtcta
1981 caagaggcct gatacccagt caatccagaa ggttcaggcc gaatttgaca gctttgtagt
2041 accgggcctg tggtcgtccg ggttgtcaat cccgttgagg actagaatca agtggttgtt
2101 acgcaaggtg ccgaaaacag acctgatccc atacagcggg aatgcccaag aagcccagga
2161 tgcagaaaaa gaagcagagg aagaacgaga agcagaactg actcatgagg ctctaccacc
2221 cctacaggca gcacaggaag atgtccaggt cgaaatcgac gtggaacagc ttgaggatag
2281 agctggtgct ggaataatag agactccgag aggcgctatc aaagttactg cccaactaac
2341 agaccacgtc gtgggggagt acctggtact ttccccgcag accgtactac gcagccagaa
2401 gctcagcctg atccacgctt tagcggagca agtgaagacg tgtacgcaca gcggacgagc
2461 agggaggtat gcggtcgaag cgtacgatgg ccgagtccta gtgccctcag gctatgcaat
```

Figure 3B

```
2521 ttcgcctgaa gacttccaga gtctaagcga aagcgcaacg atggtgtaca acgaaagaga
2581 gttcgtaaac agaaagttac accacattgc gatgcacgga ccagccctga acactgacga
2641 agagtcgtat gagctggtga gggcagagag gacagaacac gagtacgtct acgacgtgga
2701 ccagagaaga tgctgtaaga aggaagaagc tgcaggactg gtactggtgg gcgacttgac
2761 taatccgccc taccacgaat tcgcatacga agggctaaaa attcgccccg cctgcccata
2821 caaaattgca gtcataggag tcttcggggt accaggatct ggcaagtcag ccattatcaa
2881 gaacctagtt accaggcaag acctggtgac tagcggaaag aaagaaaact gccaagaaat
2941 cagcaccgac gtgatgagac agagaggtct agagatatct gcacgtacgg tagattcgct
3001 gctcttgaat ggatgcaaca gaccagtcga cgtgttgtac gtagacgagg cgtttgcgtg
3061 ccactctgga acgttacttg ctttgatcgc cttggtgaga ccaagacaga aagttgtact
3121 ttgtggtgac ccgaagcagt gcggcttctt caatatgatg cagatgaaag tcaactacaa
3181 tcataacatc tgcacccaag tgtaccacaa aagtatctcc aggcggtgta cactgcctgt
3241 gactgccatt gtgtcatcgt tgcattacga aggcaaaatg cgcactacga atgagtacaa
3301 catgccgatt gtagtggaca ctacaggctc aacgaaacct gaccctggag acctcgtgtt
3361 aacgtgcttc agagggtggg ttaaacaact gcaaattgac tatcgtggac acgaggtcat
3421 gacagcagcc gcatcccaag ggttaactag aaaaggagtt tacgcagtta ggcaaaaagt
3481 taacgaaaac ccactctatg catcaacatc agagcacgtc aacgtactcc taacgcgtac
3541 ggaaggtaaa ctggtatgga agacactctc tggtgacccg tggataaaga cgctgcagaa
3601 cccaccgaaa ggaaacttca aagcaactat taaggagtgg gaggtggagc acgcatcgat
3661 aatggcgggc atctgcagtc accaagtgac ctttgacaca ttccaaaaca aagccaacgt
3721 ttgctgggct aagagcttgg tccctatcct cgaaacagcg ggataaaac taaatgatag
3781 gcagtggtcc cagataattc aagccttcaa agaagacaaa gcatactcac ccgaagtagc
3841 cctgaatgaa atatgcacgc gcatgtatgg ggtggatcta gacagtgggc tattctctaa
3901 accgttggta tctgtgtatt acgcggataa ccattgggat aataggccgg gaggaaagat
3961 gttcggattc aaccctgagg cagcgtccat tctagaaaga aagtacccat ttacaaaagg
4021 aaagtggaac atcaacaagc agatctgcgt gactaccagg aggatagaag acttcaaccc
4081 taccaccaac attataccgg tcaacaggag actaccacac tcattagtgg ccgaacaccg
4141 cccagtaaaa ggggaaagaa tggaatggct ggttaacaag ataaacggac accacgtact
4201 cctggttagc ggctataacc ttgcactgcc tactaagaga gtcacctggg tagcgccact
4261 aggtgtccgc ggagcggact atacatacaa cctagagctg ggtctaccag caacrcttgg
4321 taggtatgac ctagtggtca taaacatcca cacacctttt cgcatacacc attaccaaca
4381 gtgcgtagat cacgcaatga aactgcaaat gctagggggt gactcactga gactgctcaa
4441 accgggtggc tctctattga tcagagcata cggttacgca gatagaacca gtgaacgagt
4501 catctgcgta ctgggacgca agtttagatc gtctagagca ttgaaaccac catgtgtcac
4561 cagtaatact gagatgtttt tcctatttag caattttgac aatggcagaa ggaattttac
4621 aacgcatgtc atgaacaatc aactgaatgc agcctttgta ggacaggcca cccgagcagg
4681 atgtgcacca tcgtaccggg taaaacgcat ggacatcgcg aagaacgatg aagagtgcgt
4741 ggttaacgcc gccaaccctc gcgggttacc aggtgacggt gtttgcaagg cagtatataa
4801 aaagtggccg gagtccttta aaaacagtgc aacaccagta ggaaccgcaa aaacagttat
4861 gtgcggtacg tatccagtaa tccacgccgt aggaccaaac ttctcaaatt attcggagtc
4921 tgaaggggac cgggaattgg cggctgccta tcgagaagtc gcaaaggaag taactagact
4981 gggagtaaat agcgtagcta tacctctcct ctccacaggt gtatactcag gagggaaaga
5041 caggctaacc cagtcactga accacctctt tacagccatg gactcgacgg atgcagacgt
5101 ggtcatctac tgccgagaca aggaatggga gaagaaaata tctgaggcca tacagatgcg
5161 gacccaagtg gagctgctgg atgagcacat ctccatagac tgcgatgtca ttcgcgtgca
```

Figure 3C

```
5221 ccctgacagt agcttggcag gcagaaaagg atacagcacc acggaaggcg cactgtattc
5281 atatctagaa gggacacgtt ttcaccagac ggcagtggat atggcagaga tatacactat
5341 gtggccaaag caaacagagg ccaatgagca agtctgccta tatgccctgg gggaaagtat
5401 tgaatcaatc aggcagaaat gcccggtgga tgatgcagac gcatcatctc ccccgaaaac
5461 tgtcccgtgt ctttgccggt atgccatgac tcctgaacgc gtcacccgac ttcgcatgaa
5521 ccatgtcaca aatataattg tgtgttcttc atttcccctt ccaaagtaca agatagaagg
5581 agtgcaaaaa gtcaaatgct ccaaggtaat gttattcgat cacaatgtgc catcgcgcgt
5641 aagtccaagg gaatacagat cttcccagga gtctgtacag gaagtgagta cgacaacgtc
5701 attgacgcat agccagtttg atctaagcgc cgatggcgag acactgcctg tcccgtcaga
5761 cctggatgct gacgccccag ccctagaacc ggccctagac gacggggcgg tacatacatt
5821 accaaccata atcggaaacc ttgcggccgt gtctgactgg gtaatgagca ccgtacctgt
5881 cgcgccgcct agaagaagga gagggagaaa cctgactgtg acatgtgacg agagagaagg
5941 gaatataaca cccatggcta gcgtccgatt ctttagagca gagctgtgtc cggccgtaca
6001 agaaacagcg gagacgcgtg acacagctat ttcccttcag gcaccgccaa gtaccaccat
6061 ggaactgagc catccaccga tctccttcgg agcaccaagc gagacgttcc ccatcacatt
6121 tggggacttc gacgaaggag aaatcgaaag cttgtcttct gagctactaa ctttcggaga
6181 cttcctaccc ggtgaagtgg atgatctgac agatagcgac tggtccacgt gcccagacac
6241 ggacgacgag ttatgactag acagggcagg tgggtatata ttctcgtcgg acactggtcc
6301 aggccattta caacagaagt cggtacgcca gtcagtgctg ccggtaaaca ccctggagga
6361 agtccacgag gagaagtgtt acccacctaa gctggatgaa ttaaaggagc aactactact
6421 taagaaactc caggagagtg cgtccatggc caatagaagc aggtatcagt cacgcaaagt
6481 ggaaaatatg aaagcaacaa tcatccagag actaaagaga ggctgtaaac tgtatttaat
6541 ggcagagacc ccgaaagtcc cgacttatcg gaccatatac ccggcgcctg tgtactcgcc
6601 tccgatcaat gtccgattgt ccaaccccga gtccgcagtg gcagcatgta atgagttctt
6661 agctagaaac tacccaactg tttcatcata ccaaatcacc gacgagtatg atgcatatct
6721 agacatggtg gacgggtcgg agagttgctt ggaccgagcg acattcaatc cgtcaaaact
6781 taggagctac ccgaaacaac atgcttatca cgcgccttct atcagaagcg ctgtaccttc
6841 cccattccag aacacactac agaatgtact ggcagcagcc acgaaaagga actgcaacgt
6901 cacacagatg agggaattac ccactttgga ctcagcagta ttcaacgtgg agtgtttaa
6961 aaaattcgca tgtaaccgag aatactggga agaatttgca gccagcccta tcaggataac
7021 aactgagaat ctaacaacct atgtcactaa actaaagggg ccaaaagcag cagcgctgtt
7081 tgcaaaaacc cataatctgc tgccactgca ggatgtacca atggataggt tcacagtaga
7141 tatgaaaagg gatgtgaagg taactcctgg tacaaagcat acagaggaaa gacctaaggt
7201 gcaggttata caggcggctg aacccttggc aacagcgtac ctatgtggaa ttcacagaga
7261 actggttagg agattgaacg ccgtcctcct acccaatgtg catacactat ttgacatgtc
7321 tgccgaggac ttcgatgcca ttatagccgc acacttcaag ccaggagacg ctgttttaga
7381 aacggacata gcctcctttg ataagagcca agatgattca cttgcgctta ccgccttaat
7441 gctgttagaa gatttgggag tggatcactc cctgttggac ttgatagagg ctgctttcgg
7501 agagatttcc agctgtcatc tgccgacagg tacgcgcttc aagttcggcg ctatgatgaa
7561 atccggtatg ttcctaactc tgttcgtcaa cacgttgtta aatatcacca tcgctagccg
7621 ggtgttggaa gatcgtctga caaaatccgc atgcgcggcc ttcatcggcg acgacaacat
7681 aatacatggt gtcgtctccg atgaattgat ggcagccaga tgcgctactt ggatgaacat
7741 ggaagtgaag atcatagatg cagttgtatc ccagaaagct ccttactttt gtggagggtt
7801 tatactgcat gatactgtga caggaacagc ttgcagagtg gcggacccgc taaaaaggtt
7861 atttaaattg ggcaaaccgt tagcggcagg tgacgaacaa gatgaagaca gaagacgggc
```

Figure 3D

```
 7921 gctggctgat gaagtaatca gatggcaacg aacagggcta atagatgagc tggagaaagc
 7981 ggtgtactct aggtacgaag tgcagggtat atcagttgcg gtaatgtcca tggccacctt
 8041 tgcaagctcc agatccaact tcgagaagct cagaggaccc gtcataactt tgtacggcgg
 8101 tcctaaatag gtacgcacta cagctaccta ttttgcagaa gccgacagca ggtacctaaa
 8161 taccaatcag ccataatgga gtttatccca acccaaactt tctacaatag gaggtaccag
 8221 cctcgacctt ggactccgcg ccctactatc caagttatca gacccagacc gcgtccgcaa
 8281 aggaaagccg ggcaacttgc ccagctgatc tcagcagtta ataaactgac aatgcgcgcg
 8341 gtacctcaac agaagccgcg caagaatcgg aagaataaga agcaaaagca aaagcagcag
 8401 gcgccacgaa acaacatgaa tcaaaagaag cagcccccta aaaagaaacc ggctcaaaag
 8461 aaaaagaagc cgggccgtag agagagaatg tgcatgaaaa tcgaaaatga ttgcatcttc
 8521 gaagtcaagc atgaaggtaa ggtaacaggt tacgcgtgct tggtagggga caaagtaatg
 8581 aagccagcac acgtaaaggg gaccatcgat aatgcggacc tggccaaatt ggccttcaag
 8641 cggtcatcta agtacgacct tgaatgcgcg cagatacccg tgcacatgaa gtccgacgct
 8701 tcgaagttca cccatgagaa accggagggg tactacaact ggcaccacgg agcagtacag
 8761 tactcaggag gccggttcac catccctaca ggtgcgggca aaccagggga cagcggtaga
 8821 ccgatcttcg acaacaaggg gcgcgtggtg gccatagttt taggaggagc taatgaagga
 8881 gcccgtacag ccctctcggt ggtgacctgg aacaaagaca tcgtcacgaa aatcaccccct
 8941 gagggggccg aagagtggag tcttgccatt ccagttatgt gcctgctggc aaataccacg
 9001 ttcccctgct cccagccccc ttgcacaccc tgctgctacg aaaaagagcc ggagaaaacc
 9061 ctgcgcatgc tagaagacaa cgtcatgagc cccgggtact atcagctgct acaagcatcc
 9121 ttaacatgtt ctccccgccg ccagcgacgc agtattaagg acaacttcaa tgtctataaa
 9181 gccataagac cgtacctagc tcactgtccc gactgtggag aagggcactc gtgccatagt
 9241 cccgtagcgc tagaacgcat cagaaacgaa gcgacagacg ggacgctgaa aatccaggtt
 9301 tccttgcaaa tcggaataaa gacggatgat agccatgatt ggaccaagct gcgttacatg
 9361 gacaatcata tgccagcaga cgcagagagg gccaggctat ttgtaagaac gtcagcaccg
 9421 tgcacgatta ctggaacaat gggacacttc atcctggccc gatgtccgaa aggagaaact
 9481 ctgacggtgg gattcactga cggtaggaag atcagtcact catgtacgca cccatttcac
 9541 cacgaccctc ctgtgatagg ccgggaaaaa tttcattccc gaccgcagca cggtagagaa
 9601 ctaccttgca gcacgtacgc gcagagcacc gctgcaactg ccgaggagat agaggtacat
 9661 atgcccccag acaccccaga tcgcacattg atgtcacaac agtccggtaa tgtaaagatc
 9721 acagtcaata gtcagacggt gcggtacaag tgtaattgcg gtgactcaaa tgaaggacta
 9781 accactacag acaaagtgat taataactgc aaggttgatc aatgccatgc cgcggtcacc
 9841 aatcacaaaa aatggcagta taattcccct ctggtcccgc gtaatgctga actcggggac
 9901 cgaaaaggaa aagttcacat tccgtttcct ctggcaaatg tgacatgcag ggtgcctaag
 9961 gcaaggaacc ccaccgtgac gtacggaaaa aaccaagtca tcatgctgct gtatcctgac
10021 cacccaacgc tcctgtccta ccggaatatg ggagaagaac caaactatca agaagagtgg
10081 gtgacgcata agaaggagat caggttaacc gtgccgactg aagggctcga ggtcacgtgg
10141 ggcaacaacg agccgtacaa gtattggccg cagttatcca caaacggtac agcccacggc
10201 cacccgcatg agataatttt gtattattat gagctgtacc ctactatgac tgtggtagtt
10261 gtgtcagtgg cctcgttcgt actcctgtcg atggtgggtg tggcagtggg gatgtgcatg
10321 tgtgcacgac gcagatgcat tacaccgtac gaactgacac caggagctac cgtccctttc
10381 ctgcttagcc taatatgctg cattagaaca gctaaagcgg ccacatacca agaggctgcg
10441 gtatacctgt ggaacgagca gcagcctttg ttttggctgc aagcccttat tccgctggca
10501 gccctgattg tcctatgcaa ctgtctgaga ctcttaccat gcttttgtaa aacgttgact
10561 tttttagccg taatgagcgt cggtgcccac actgtgagcg cgtacgaaca cgtaacagtg
```

Figure 3E 10621 atcccgaaca cggtgggagt accgtataag actctagtca acagaccggg ctacagcccc  
10681 atggtactgg agatggagct tctgtcagtc actttggagc caacgctatc gcttgattac  
10741 atcacgtgcg agtataaaac cgtcatcccg tctccgtacg tgaaatgctg cggtacagca  
10801 gagtgcaagg acaagagcct acctgattac agctgtaagg tcttcaccgg cgtctaccca  
10861 ttcatgtggg gcggcgccta ctgcttctgc gacactgaaa atacgcaatt gagcgaagca  
10921 catgtggaga agtccgaatc atgcaaaaca gaatttgcat cagcatatag ggctcatacc  
10981 gcatccgcat cagctaagct ccgcgtcctt taccaaggaa ataatgttac tgtatctgct  
11041 tatgcaaacg gcgatcatgc cgtcacagtt aaggacgcta aattcattgt ggggccaatg  
11101 tcttcagcct ggacaccttt tgacaataaa atcgtggtgt acaaaggcga cgtctacaac  
11161 atggactacc cgcccttcgg cgcaggaaga ccaggacaat ttggcgacat ccaaagtcgc  
11221 acgcctgaga gcgaagacgt ctatgctaac acacaactgg tactgcagag accgtccgcg  
11281 ggtacggtgc acgtgccgta ctctcaggca ccatctggct tcaagtattg gctaaaagaa  
11341 cgaggggcgt cgctgcagca cacagcacca tttggctgtc aaatagcaac aaacccggta  
11401 agagcgatga actgcgccgt agggaacatg cctatctcca tcgacatacc ggacgcggcc  
11461 ttcactaggg tcgtcgacgc gccatcttta acggacatgt cgtgtgaggt accagcctgc  
11521 acccactcct cagactttgg gggcgtagcc atcattaaat atgcagccag caagaaaggc  
11581 aagtgtgcgg tgcattcgat gactaacgcc gtcactattc gggaagctga aatagaagta  
11641 gaagggaact ctcagttgca aatctctttt tcgacggccc tagccagcgc cgaattccgc  
11701 gtacaagtct gttctacaca agtacactgt gcagccgagt gccatccacc gaaagaccat  
11761 atagtcaatt acccggcgtc acacaccacc ctcggggtcc aagacatttc cgttacggcg  
11821 atgtcatggg tgcagaagat cacgggaggt gtgggactgg ttgtcgctgt tgcagcactg  
11881 atcctaatcg tggtgctatg cgtgtcgttt agcaggcact aacttgacaa ctaggtacga  
11941 aggtatatgt gtcccctaag agacacacca catatagcta agaatcaata gataagtata  
12001 gatcaaaggg ctgaacaacc cctgaatagt aacaaaatat aaaaatcaac aaaaatcata  
12061 aaatagaaaa ccagaaacag aagtaggtaa gaaggtatat gtgtccccta agagacacac  
12121 catatatagc taagaatcaa tagataagta tagatcaaag ggctgaataa cccctgaata  
12181 ataacaaaat ataaaaatca ataaaaatca taaaatagaa aaccataaac agaagtagtt  
12241 caaagggcta taaaacccct gaatagtaac aaaacataaa actaataaaa atcaaatgaa  
12301 taccataatt ggcaatcgga agagatgtag gtacttaagc ttcctaaaag cagccgaact  
12361 cgctttgaga tgtaggcgta gcacaccgaa ctcttccata attctccgaa cccacaggga  
12421 cgtaggagat gttcaaagtg gctataaaac cctgaacagt aataaaacat aaaattaata  
12481 aggatcaaat gagtaccata attggcaaac ggaagagatg taggtactta agcttcctaa  
12541 aagcagccga actcactttg agatgtaggc atagcatacc gaactcttcc acaattctcc  
12601 gtacccatag ggacgtagga gatgttattt tgtttttaat atttcAAAAA AAAAAAAAAA  
12661 AAAAAAAAGG GTAC*tgggtc* *ggcatggcat* *ctccacctcc* *tcgcggtccg* *acctgggcat*  
*12721* *ccgaaggagg* *acgcacgtcc* *actcggatgg* *ctaagggaga* *gccacgagct* *cctcgacaga*  
*12781* *tcataatcag* *ccataccaca* *tttgtagagg* *ttttacttgc* *tttaaaaaac* *ctcccacacc*  
*12841* *tcccctgaa* *cctgaaacat* *aaaatgaatg* *caattgttgt* *tgttaacttg* *tttattgcag*  
*12901* *cttataatgg* *ttacaaataa* *agcaatagca* *tcacaaattt* *cacaaataaa* *gcattttttt*  
*12961* *cactgcattc* *tagttgtggt* *ttgtccaaac* *tcatcaagat* GCGGCCGCCA CTGTGCTGGA  
13021 TATCTGCAGA ATTCCACCAC ACTGGACTAG TGGATCAGCT TAAGTTTAAA CCGCTGATCA  
13081 GCCTCGACTG TGCCTTCTAG TTGCCAGCCA TCTGTTGTTT GCCCCTCCCC CGTGCCTTCC  
13141 TTGACCCTGG AAGGTGCCAC TCCCACTGTC CTTTCCTAAT AAAATGAGGA AATTGCATCG  
13201 CATTGTCTGA GTAGGTGTCA TTCTATTCTG GGGGGTGGGG TGGGGCAGGA C Figures 4A-4E: An i-DNA sequence.

Figure 4A

```
   1 GGCGCGCCTG ACATTGATTA TTGACTAGTT ATTAATAGTA ATCAATTACG GGGTCATTAG
  61 TTCATAGCCC ATATATGGAG TTCCGCGTTA CATAACTTAC GGTAAATGGC CCGCCTGGCT
 121 GACCGCCCAA CGACCCCCGC CCATTGACGT CAATAATGAC GTATGTTCCC ATAGTAACGC
 181 CAATAGGGAC TTTCCATTGA CGTCAATGGG TGGAGTATTT ACGGTAAACT GCCCACTTGG
 241 CAGTACATCA AGTGTATCAT ATGCCAAGTA CGCCCCCTAT TGACGTCAAT GACGGTAAAT
 301 GGCCCGCCTG GCATTATGCC CAGTACATGA CCTTATGGGA CTTTCCTACT TGGCAGTACA
 361 TCTACGTATT AGTCATCGCT ATTACCATGG TGATGCGGTT TTGGCAGTAC ATCAATGGGC
 421 GTGGATAGCG GTTTGACTCA CGGGGATTTC CAAGTCTCCA CCCCATTGAC GTCAATGGGA
 481 GTTTGTTTTG GCACCAAAAT CAACGGGACT TTCCAAAATG TCGTAACAAC TCCGCCCCAT
 541 TGACGCAAAT GGGCGGTAGG CGTGTACGGT GGGAGGTCTA TATAAGCAGA GCTCTCTGGC
 601 TAACTAGAGa tggctgcgtg agacacacgt agcctaccag tttcttactg ctctactctg
 661 caaagcaaga gattaataac ccatcatgga ttctgtgtac gtggacatag acgctgacag
 721 cgcctttttg aaggccctgc aacgtgcgta ccccatgttt gaggtggaac ctaggcaggt
 781 cacatcgaat gaccatgcta atgctagagc gttctcgcat ctagccataa aactaataga
 841 gcaggaaatt gatcccgact caaccatcct ggatataggt agtgcgccag caaggaggat
 901 gatgtcggac aggaagtacc actgcgtttg cccgatgcgc agcgcagaag atcccgagag
 961 actcgctaat tatgcgagaa agctcgcatc tgccgcagga aaagtcctgg acagaaacat
1021 ttctggaaag atcggggact tacaagcggt gatggccgtg ccagacacgg agacgccaac
1081 attttgctta cacacagatg tctcatgtag acagagagca gacgtcgcga tataccaaga
1141 cgtctatgct gtacacgcac ccacgtcgct ataccaccag gcgattaaag gagtccgagt
1201 ggcgtactgg gtagggttcg acacaacccc gttcatgtac aacgctatgg cgggtgccta
1261 cccctcatac tcgacaaatt gggcggatga gcaggtactg aaggctaaga acataggatt
1321 atgttcaaca gacctgacgg aaggtagacg aggcaaattg tctatcatga gagggaaaaa
1381 gctaaaaccg tgcgaccgtg tgctgttctc agtagggtca acgctttacc cggaaagccg
1441 cacgctactt aagagctggc acctaccatc ggtgttccat ctaaagggca agcttagctt
1501 cacatgccgc tgtgacacag tggtttcgtg tgagggctac gtcgttaaga gaataacgat
1561 gagcccaggc ctttatggaa aaaccatagg gtatgcggta acccaccacg cagacggatt
1621 cttgatgtgc aagactaccg acacggttga cggcgaaaga gtgtcattct cggtgtgcac
1681 gtacgtgccg gcgaccattt gtgatcaaat gaccggcatc cttgctacag aagtcacgcc
1741 ggaggatgca cagaagctgt tggtggggct gaaccagagg atagtggtta acggcagaac
1801 gcaacggaac acgaacacca tgaagaacta cctacttccc gtggtcgccc aggccttcag
1861 taagtgggca aaggagtgcc ggaaggacat ggaagatgag aagcttctgg gggtcagaga
1921 aagaacacta acctgctgct gtctatgggc atttaagaag cagaaaacac acacggtcta
1981 caagaggcct gatacccagt caatccagaa ggttcaggcc gaatttgaca gctttgtagt
2041 accgggcctg tggtcgtccg ggttgtcaat cccgttgagg actagaatca agtggttgtt
2101 acgcaaggtg ccgaaaacag acctgatccc atacagcggg aatgcccaag aagcccagga
2161 tgcagaaaaa gaagcagagg aagaacgaga agcagaactg actcatgagg ctctaccacc
2221 cctacaggca gcacaggaag atgtccaggt cgaaatcgac gtggaacagc ttgaggatag
2281 agctggtgct ggaataatag agactccgag aggcgctatc aaagttactg cccaactaac
2341 agaccacgtc gtgggggagt acctggtact ttccccgcag accgtactac gcagccagaa
2401 gctcagcctg atccacgctt tagcggagca agtgaagacg tgtacgcaca gcggacgagc
2461 agggaggtat gcggtcgaag cgtacgatgg ccgagtccta gtgccctcag gctatgcaat
2521 ttcgcctgaa gacttccaga gtctaagcga aagcgcaacg atggtgtaca acgaaagaga
```

Figure 4B

```
2581 gttcgtaaac agaaagttac accacattgc gatgcacgga ccagccctga acactgacga
2641 agagtcgtat gagctggtga gggcagagag gacagaacac gagtacgtct acgacgtgga
2701 ccagagaaga tgctgtaaga aggaagaagc tgcaggactg gtactggtgg gcgacttgac
2761 taatccgccc taccacgaat tcgcatacga agggctaaaa attcgccccg cctgcccata
2821 caaaattgca gtcataggag tcttcggggt accaggatct ggcaagtcag ccattatcaa
2881 gaacctagtt accaggcaag acctggtgac tagcggaaag aaagaaaact gccaagaaat
2941 cagcaccgac gtgatgagac agagaggtct agagatatct gcacgtacgg tagattcgct
3001 gctcttgaat ggatgcaaca gaccagtcga cgtgttgtac gtagacgagg cgtttgcgtg
3061 ccactctgga acgttacttg ctttgatcgc cttggtgaga ccaagacaga aagttgtact
3121 ttgtggtgac ccgaagcagt gcggcttctt caatatgatg cagatgaaag tcaactacaa
3181 tcataacatc tgcacccaag tgtaccacaa aagtatctcc aggcggtgta cactgcctgt
3241 gactgccatt gtgtcatcgt tgcattacga aggcaaaatg cgcactacga atgagtacaa
3301 catgccgatt gtagtggaca ctacaggctc aacgaaacct gaccctggag acctcgtgtt
3361 aacgtgcttc agagggtggg ttaaacaact gcaaattgac tatcgtggac acgaggtcat
3421 gacagcagcc gcatcccaag ggttaactag aaaaggagtt tacgcagtta ggcaaaaagt
3481 taacgaaaac ccactctatg catcaacatc agagcacgtc aacgtactcc taacgcgtac
3541 ggaaggtaaa ctggtatgga agacactctc tggtgacccg tggataaaga cgctgcagaa
3601 cccaccgaaa ggaaacttca aagcaactat taaggagtgg gaggtggagc acgcatcgat
3661 aatggcgggc atctgcagtc accaagtgac ctttgacaca ttccaaaaca aagccaacgt
3721 ttgctgggct aagagcttgg tccctatcct cgaaacagcg ggataaaac taaatgatag
3781 gcagtggtcc cagataattc aagccttcaa agaagacaaa gcatactcac ccgaagtagc
3841 cctgaatgaa atatgcacgc gcatgtatgg ggtggatcta gacagtgggc tattctctaa
3901 accgttggta tctgtgtatt acgcggataa ccattgggat aataggccgg gaggaaagat
3961 gttcggattc aaccctgagg cagcgtccat tctagaaaga aagtacccat ttacaaaagg
4021 aaagtggaac atcaacaagc agatctgcgt gactaccagg aggatagaag acttcaaccc
4081 taccaccaac attataccgg tcaacaggag actaccacac tcattagtgg ccgaacaccg
4141 cccagtaaaa ggggaaagaa tggaatggct ggttaacaag ataaacggac accacgtact
4201 cctggttagc ggctataacc ttgcactgcc tactaagaga gtcacctggg tagcgccact
4261 aggtgtccgc ggagcggact atacatacaa cctagagctg ggtctaccag caacrcttgg
4321 taggtatgac ctagtggtca taaacatcca cacacctttt cgcatacacc attaccaaca
4381 gtgcgtagat cacgcaatga aactgcaaat gctagggggt gactcactga gactgctcaa
4441 accgggtggc tctctattga tcagagcata cggttacgca gatagaacca gtgaacgagt
4501 catctgcgta ctgggacgca agtttagatc gtctagagca ttgaaaccac catgtgtcac
4561 cagtaatact gagatgtttt tcctatttag caattttgac aatggcagaa ggaattttac
4621 aacgcatgtc atgaacaatc aactgaatgc agcctttgta ggacaggcca cccgagcagg
4681 atgtgcacca tcgtaccggg taaaacgcat ggacatcgcg aagaacgatg aagagtgcgt
4741 ggttaacgcc gccaaccctc gcgggttacc aggtgacggt gtttgcaagg cagtatataa
4801 aaagtggccg gagtccttta aaaacagtgc aacaccagta ggaaccgcaa aaacagttat
4861 gtgcggtacg tatccagtaa tccacgccgt aggaccaaac ttctcaaatt attcggagtc
4921 tgaaggggac cgggaattgg cggctgccta tcgagaagtc gcaaaggaag taactagact
4981 gggagtaaat agcgtagcta tacctctcct ctccacaggt gtatactcag gagggaaaga
5041 caggctaacc cagtcactga accacctctt tacagccatg gactcgacgg atgcagacgt
5101 ggtcatctac tgccgagaca aggaatggga gaagaaaata tctgaggcca tacagatgcg
5161 gacccaagtg gagctgctgg atgagcacat ctccatagac tgcgatgtca ttcgcgtgca
5221 ccctgacagt agcttggcag gcagaaaagg atacagcacc acggaaggcg cactgtattc
```

Figure 4C

```
5281 atatctagaa gggacacgtt ttcaccagac ggcagtggat atggcagaga tatacactat
5341 gtggccaaag caaacagagg ccaatgagca agtctgccta tatgccctgg gggaaagtat
5401 tgaatcaatc aggcagaaat gcccggtgga tgatgcagac gcatcatctc ccccgaaaac
5461 tgtcccgtgt ctttgccggt atgccatgac tcctgaacgc gtcacccgac ttcgcatgaa
5521 ccatgtcaca aatataattg tgtgttcttc atttcccctt ccaaagtaca agatagaagg
5581 agtgcaaaaa gtcaaatgct ccaaggtaat gttattcgat cacaatgtgc catcgcgcgt
5641 aagtccaagg gaatacagat cttcccagga gtctgtacag gaagtgagta cgacaacgtc
5701 attgacgcat agccagtttg atctaagcgc cgatggcgag acactgcctg tcccgtcaga
5761 cctggatgct gacgccccag ccctagaacc ggccctagac gacggggcgg tacatacatt
5821 accaaccata atcggaaacc ttgcggccgt gtctgactgg gtaatgagca ccgtacctgt
5881 cgcgccgcct agaagaagga gagggagaaa cctgactgtg acatgtgacg agagagaagg
5941 gaatataaca cccatggcta gcgtccgatt ctttagagca gagctgtgtc cggccgtaca
6001 agaaacagcg gagacgcgtg acacagctat ttcccttcag gcaccgccaa gtaccaccat
6061 ggaactgagc catccaccga tctccttcgg agcaccaagc gagacgttcc ccatcacatt
6121 tggggacttc gacgaaggag aaatcgaaag cttgtcttct gagctactaa ctttcggaga
6181 cttcctaccc ggtgaagtgg atgatctgac agatagcgac tggtccacgt gcccagacac
6241 ggacgacgag ttatgactag acagggcagg tgggtatata ttctcgtcgg acactggtcc
6301 aggccattta caacagaagt cggtacgcca gtcagtgctg ccggtaaaca ccctggagga
6361 agtccacgag gagaagtgtt acccacctaa gctggatgaa ttaaaggagc aactactact
6421 taagaaactc caggagagtg cgtccatggc caatagaagc aggtatcagt cacgcaaagt
6481 ggaaaatatg aaagcaacaa tcatccagag actaaagaga ggctgtaaac tgtatttaat
6541 ggcagagacc ccgaaagtcc cgacttatcg gaccatatac ccggcgcctg tgtactcgcc
6601 tccgatcaat gtccgattgt ccaaccccga gtccgcagtg gcagcatgta atgagttctt
6661 agctagaaac tacccaactg tttcatcata ccaaatcacc gacgagtatg atgcatatct
6721 agacatggtg gacgggtcgg agagttgctt ggaccgagcg acattcaatc cgtcaaaact
6781 taggagctac ccgaaacaac atgcttatca cgcgccttct atcagaagcg ctgtaccttc
6841 cccattccag aacacactac agaatgtact ggcagcagcc acgaaaagga actgcaacgt
6901 cacacagatg agggaattac ccactttgga ctcagcagta ttcaacgtgg agtgttttaa
6961 aaaattcgca tgtaaccgag aatactggga agaatttgca gccagcccta tcaggataac
7021 aactgagaat ctaacaacct atgtcactaa actaaagggg ccaaaagcag cagcgctgtt
7081 tgcaaaaacc cataatctgc tgccactgca ggatgtacca atggataggt tcacagtaga
7141 tatgaaaagg gatgtgaagg taactcctgg tacaaagcat acagaggaaa gacctaaggt
7201 gcaggttata caggcggctg aacccttggc aacagcgtac ctatgtggaa ttcacagaga
7261 actggttagg agattgaacg ccgtcctcct acccaatgtg catacactat ttgacatgtc
7321 tgccgaggac ttcgatgcca ttatagccgc acacttcaag ccaggagacg ctgttttaga
7381 aacggacata gcctcctttg ataagagcca agatgattca cttgcgctta ccgccttaat
7441 gctgttagaa gatttgggag tggatcactc cctgttggac ttgatagagg ctgctttcgg
7501 agagatttcc agctgtcatc tgccgacagg tacgcgcttc aagttcggcg ctatgatgaa
7561 atccggtatg ttcctaactc tgttcgtcaa cacgttgtta aatatcacca tcgctagccg
7621 ggtgttggaa gatcgtctga caaaatccgc atgcgcggcc ttcatcggcg acgacaacat
7681 aatacatggt gtcgtctccg atgaattgat ggcagccaga tgcgctactt ggatgaacat
7741 ggaagtgaag atcatagatg cagttgtatc ccagaaagct ccttactttt gtggagggtt
7801 tatactgcat gatactgtga caggaacagc ttgcagagtg gcggacccgc taaaaaggtt
7861 atttaaattg ggcaaaccgt tagcggcagg tgacgaacaa gatgaagaca gaagacgggc
7921 gctggctgat gaagtaatca gatggcaacg aacagggcta atagatgagc tggagaaagc
```

Figure 4D

```
 7981 ggtgtactct aggtacgaag tgcagggtat atcagttgcg gtaatgtcca tggccacctt
 8041 tgcaagctcc agatccaact tcgagaagct cagaggaccc gtcataactt tgtacggcgg
 8101 tcctaaatag gtacgcacta cagctaccta ttttgcagaa gccgacagca ggtacctaaa
 8161 taccaatcag ccataatgga gtttatccca acccaaactt tctacaatag gaggtaccag
 8221 cctcgacctt ggactccgcg ccctactatc caagttatca gacccagacc gcgtccgcaa
 8281 aggaaagccg ggcaacttgc ccagctgatc tcagcagtta ataaactgac aatgcgcgcg
 8341 gtacctcaac agaagccgcg caagaatcgg aagaataaga agcaaaagca aaagcagcag
 8401 gcgccacgaa acaacatgaa tcaaaagaag cagcccccta aaaagaaacc ggctcaaaag
 8461 aaaaagaagc cgggccgtag agagagaatg tgcatgaaaa tcgaaaatga ttgcatcttc
 8521 gaagtcaagc atgaaggtaa ggtaacaggt tacgcgtgct tggtagggga caaagtaatg
 8581 aagccagcac acgtaaaggg gaccatcgat aatgcggacc tggccaaatt ggccttcaag
 8641 cggtcatcta agtacgacct tgaatgcgcg cagatacccg tgcacatgaa gtccgacgct
 8701 tcgaagttca cccatgagaa accggagggg tactacaact ggcaccacgg agcagtacag
 8761 tactcaggag gccggttcac catccctaca ggtgcgggca aaccagggga cagcggtaga
 8821 ccgatcttcg acaacaaggg gcgcgtggtg gccatagttt taggaggagc taatgaagga
 8881 gcccgtacag ccctctcggt ggtgacctgg aacaaagaca tcgtcacgaa aatcacccct
 8941 gagggggccg aagagtggag tcttgccatt ccagttatgt gcctgctggc aaataccacg
 9001 ttcccctgct cccagccccc ttgcacaccc tgctgctacg aaaaagagcc ggagaaaacc
 9061 ctgcgcatgc tagaagacaa cgtcatgagc cccgggtact atcagctgct acaagcatcc
 9121 ttaacatgtt ctccccgccg ccagcgacgc agtattaagg acaacttcaa tgtctataaa
 9181 gccataagac cgtacctagc tcactgtccc gactgtggag aagggcactc gtgccatagt
 9241 cccgtagcgc tagaacgcat cagaaacgaa gcgacagacg ggacgctgaa aatccaggtt
 9301 tccttgcaaa tcggaataaa gacggatgat agccatgatt ggaccaagct gcgttacatg
 9361 gacaatcata tgccagcaga cgcagagagg gccaggctat ttgtaagaac gtcagcaccg
 9421 tgcacgatta ctggaacaat gggacacttc atcctggccc gatgtccgaa aggagaaact
 9481 ctgacggtgg gattcactga cggtaggaag atcagtcact catgtacgca cccatttcac
 9541 cacgaccctc ctgtgatagg ccgggaaaaa tttcattccc gaccgcagca cggtagagaa
 9601 ctaccttgca gcacgtacgc gcagagcacc gctgcaactg ccgaggagat agaggtacat
 9661 atgcccccag acacccccga tcgcacattg atgtcacaac agtccggtaa tgtaaagatc
 9721 acagtcaata gtcagacggt gcggtacaag tgtaattgcg gtgactcaaa tgaaggacta
 9781 accactacag acaaagtgat taataactgc aaggttgatc aatgccatgc cgcggtcacc
 9841 aatcacaaaa aatggcagta taattcccct ctggtcccgc gtaatgctga actcggggac
 9901 cgaaaaggaa aagttcacat tccgtttcct ctggcaaatg tgacatgcag ggtgcctaag
 9961 gcaaggaacc ccaccgtgac gtacggaaaa aaccaagtca tcatgctgct gtatcctgac
10021 cacccaacgc tcctgtccta ccggaatatg ggagaagaac caaactatca agaagagtgg
10081 gtgacgcata agaaggagat caggttaacc gtgccgactg aagggctcga ggtcacgtgg
10141 ggcaacaacg agccgtacaa gtattggccg cagttatcca caaacggtac agcccacggc
10201 cacccgcatg agataatttt gtattattat gagctgtacc ctactatgac tgtggtagtt
10261 gtgtcagtgg cctcgttcgt actcctgtcg atggtgggtg tggcagtggg gatgtgcatg
10321 tgtgcacgac gcagatgcat tacaccgtac gaactgacac caggagctac cgtccctttc
10381 ctgcttagcc taatatgctg cattagaaca gctaaagcgg ccacatacca agaggctgcg
10441 gtatacctgt ggaacgagca gcagcctttg ttttggctgc aagcccttat tccgctggca
10501 gccctgattg tcctatgcaa ctgtctgaga ctcttaccat gcttttgtaa aacgttgact
10561 tttttagccg taatgagcgt cggtgcccac actgtgagcg cgtacgaaca cgtaacagtg
10621 atcccgaaca cggtgggagt accgtataag actctagtca acagaccggg ctacagcccc
```

Figure 4E

```
10681 atggtactgg agatggagct tctgtcagtc actttggagc caacgctatc gcttgattac
10741 atcacgtgcg agtataaaac cgtcatcccg tctccgtacg tgaaatgctg cggtacagca
10801 gagtgcaagg acaagagcct acctgattac agctgtaagg tcttcaccgg cgtctaccca
10861 ttcatgtggg gcggcgccta ctgcttctgc gacactgaaa atacgcaatt gagcgaagca
10921 catgtggaga agtccgaatc atgcaaaaca gaatttgcat cagcatatag ggctcatacc
10981 gcatccgcat cagctaagct ccgcgtcctt taccaaggaa ataatgttac tgtatctgct
11041 tatgcaaacg gcgatcatgc cgtcacagtt aaggacgcta aattcattgt ggggccaatg
11101 tcttcagcct ggacaccttt tgacaataaa atcgtggtgt acaaaggcga cgtctacaac
11161 atggactacc cgcccttcgg cgcaggaaga ccaggacaat ttggcgacat ccaaagtcgc
11221 acgcctgaga gcgaagacgt ctatgctaac acacaactgg tactgcagag accgtccgcg
11281 ggtacggtgc acgtgccgta ctctcaggca ccatctggct tcaagtattg gctaaaagaa
11341 cgaggggcgt cgctgcagca cacagcacca tttggctgtc aaatagcaac aaacccggta
11401 agagcgatga actgcgccgt agggaacatg cctatctcca tcgacatacc ggacgcggcc
11461 ttcactaggg tcgtcgacgc gccatcttta acggacatgt cgtgtgaggt accagcctgc
11521 acccactcct cagactttgg gggcgtagcc atcattaaat atgcagccag caagaaaggc
11581 aagtgtgcgg tgcattcgat gactaacgcc gtcactattc gggaagctga aatagaagta
11641 gaagggaact ctcagttgca aatctctttt tcgacggccc tagccagcgc cgaattccgc
11701 gtacaagtct gttctacaca agtacactgt gcagccgagt gccatccacc gaaagaccat
11761 atagtcaatt acccggcgtc acacaccacc ctcggggtcc aagacatttc cgttacggcg
11821 atgtcatggg tgcagaagat cacgggaggt gtgggactgg ttgtcgctgt tgcagcactg
11881 atcctaatcg tggtgctatg cgtgtcgttt agcaggcact aacttgacaa ctaggtacga
11941 aggtatatgt gtcccctaag agacacacca catatagcta agaatcaata gataagtata
12001 gatcaaaggg ctgaacaacc cctgaatagt aacaaaatat aaaaatcaac aaaaatcata
12061 aaatagaaaa ccagaaacag aagtaggtaa gaaggtatat gtgtccccta agagacacac
12121 catatatagc taagaatcaa tagataagta tagatcaaag ggctgaataa cccctgaata
12181 ataacaaaat ataaaaatca ataaaaatca taaaatagaa aaccataaac agaagtagtt
12241 caaagggcta taaaacccct gaatagtaac aaaacataaa actaataaaa atcaaatgaa
12301 taccataatt ggcaatcgga agagatgtag gtacttaagc ttcctaaaag cagccgaact
12361 cgctttgaga tgtaggcgta gcacaccgaa ctcttccata attctccgaa cccacaggga
12421 cgtaggagat gttcaaagtg gctataaaac cctgaacagt aataaaacat aaaattaata
12481 aggatcaaat gagtaccata attggcaaac ggaagagatg taggtactta agcttcctaa
12541 aagcagccga actcactttg agatgtaggc atagcatacc gaactcttcc acaattctcc
12601 gtacccatag ggacgtagga gatgttattt tgtttttaat atttcAAAAA AAAAAAAAAA
12661 AAAAAAGGGT ACGCGGCCGC CACTGTGCTG GATATCTGCA GAATTCCACC ACACTGGACT
12721 AGTGGATCAG CTTAAGTTTA AACCGCTGAT CAGCCTCGAC TGTGCCTTCT AGTTGCCAGC
12781 CATCTGTTGT TTGCCCCTCC CCCGTGCCTT CCTTGACCCT GGAAGGTGCC ACTCCCACTG
12841 TCCTTTCCTA ATAAAATGAG GAAATTGCAT CGCATTGTCT GAGTAGGTGT CATTCTATTC
12901 TGGGGGGTGG GGTGGGGCAG GAC
```

Figures 5A-5E: An i-DNA sequence with a duplicated 26S promoter (highlighted in italics).

Figure 5A

```
   1 GGCGCGCCTG ACATTGATTA TTGACTAGTT ATTAATAGTA ATCAATTACG GGGTCATTAG
  61 TTCATAGCCC ATATATGGAG TTCCGCGTTA CATAACTTAC GGTAAATGGC CCGCCTGGCT
 121 GACCGCCCAA CGACCCCCGC CCATTGACGT CAATAATGAC GTATGTTCCC ATAGTAACGC
 181 CAATAGGGAC TTTCCATTGA CGTCAATGGG TGGAGTATTT ACGGTAAACT GCCCACTTGG
 241 CAGTACATCA AGTGTATCAT ATGCCAAGTA CGCCCCCTAT TGACGTCAAT GACGGTAAAT
 301 GGCCCGCCTG GCATTATGCC CAGTACATGA CCTTATGGGA CTTTCCTACT TGGCAGTACA
 361 TCTACGTATT AGTCATCGCT ATTACCATGG TGATGCGGTT TTGGCAGTAC ATCAATGGGC
 421 GTGGATAGCG GTTTGACTCA CGGGGATTTC CAAGTCTCCA CCCCATTGAC GTCAATGGGA
 481 GTTTGTTTTG GCACCAAAAT CAACGGGACT TTCCAAAATG TCGTAACAAC TCCGCCCCAT
 541 TGACGCAAAT GGGCGGTAGG CGTGTACGGT GGGAGGTCTA TATAAGCAGA GCTCTCTGGC
 601 TAACTAGAGa tggctgcgtg agacacacgt agcctaccag tttcttactg ctctactctg
 661 caaagcaaga gattaataac ccatcatgga ttctgtgtac gtggacatag acgctgacag
 721 cgcctttttg aaggccctgc aacgtgcgta ccccatgttt gaggtggaac ctaggcaggt
 781 cacatcgaat gaccatgcta atgctagagc gttctcgcat ctagccataa aactaataga
 841 gcaggaaatt gatcccgact caaccatcct ggatataggt agtgcgccag caaggaggat
 901 gatgtcggac aggaagtacc actgcgtttg cccgatgcgc agcgcagaag atcccgagag
 961 actcgctaat tatgcgagaa agctcgcatc tgccgcagga aaagtcctgg acagaaacat
1021 ttctggaaag atcggggact tacaagcggt gatggccgtg ccagacacgg agacgccaac
1081 attttgctta cacacagatg tctcatgtag acagagagca gacgtcgcga tataccaaga
1141 cgtctatgct gtacacgcac ccacgtcgct ataccaccag gcgattaaag gagtccgagt
1201 ggcgtactgg gtagggttcg acacaacccc gttcatgtac aacgctatgg cgggtgccta
1261 cccctcatac tcgacaaatt gggcggatga gcaggtactg aaggctaaga acataggatt
1321 atgttcaaca gacctgacgg aaggtagacg aggcaaattg tctatcatga gagggaaaaa
1381 gctaaaaccg tgcgaccgtg tgctgttctc agtagggtca acgctttacc cggaaagccg
1441 cacgctactt aagagctggc acctaccatc ggtgttccat ctaaagggca agcttagctt
1501 cacatgccgc tgtgacacag tggtttcgtg tgagggctac gtcgttaaga gaataacgat
1561 gagcccaggc ctttatggaa aaaccatagg gtatgcggta acccaccacg cagacggatt
1621 cttgatgtgc aagactaccg acacggttga cggcgaaaga gtgtcattct cggtgtgcac
1681 gtacgtgccg gcgaccattt gtgatcaaat gaccggcatc cttgctacag aagtcacgcc
1741 ggaggatgca cagaagctgt tggtggggct gaaccagagg atagtggtta acggcagaac
1801 gcaacggaac acgaacacca tgaagaacta cctacttccc gtggtcgccc aggccttcag
1861 taagtgggca aaggagtgcc ggaaggacat ggaagatgag aagcttctgg gggtcagaga
1921 aagaacacta acctgctgct gtctatgggc atttaagaag cagaaaacac acacggtcta
1981 caagaggcct gatacccagt caatccagaa ggttcaggcc gaatttgaca gctttgtagt
2041 accgggcctg tggtcgtccg ggttgtcaat cccgttgagg actagaatca agtggttgtt
2101 acgcaaggtg ccgaaaacag acctgatccc atacagcggg aatgcccaag aagcccagga
2161 tgcagaaaaa gaagcagagg aagaacgaga agcagaactg actcatgagg ctctaccacc
2221 cctacaggca gcacaggaag atgtccaggt cgaaatcgac gtggaacagc ttgaggatag
2281 agctggtgct ggaataatag agactccgag aggcgctatc aaagttactg cccaactaac
2341 agaccacgtc gtgggggagt acctggtact ttccccgcag accgtactac gcagccagaa
2401 gctcagcctg atccacgctt tagcggagca agtgaagacg tgtacgcaca gcggacgagc
```

Figure 5B 2461 agggaggtat gcggtcgaag cgtacgatgg ccgagtccta gtgccctcag gctatgcaat
2521 ttcgcctgaa gacttccaga gtctaagcga aagcgcaacg atggtgtaca acgaaagaga
2581 gttcgtaaac agaaagttac accacattgc gatgcacgga ccagccctga acactgacga
2641 agagtcgtat gagctggtga gggcagagag gacagaacac gagtacgtct acgacgtgga
2701 ccagagaaga tgctgtaaga aggaagaagc tgcaggactg gtactggtgg gcgacttgac
2761 taatccgccc taccacgaat tcgcatacga agggctaaaa attcgccccg cctgcccata
2821 caaaattgca gtcataggag tcttcggggt accaggatct ggcaagtcag ccattatcaa
2881 gaacctagtt accaggcaag acctggtgac tagcggaaag aaagaaaact gccaagaaat
2941 cagcaccgac gtgatgagac agagaggtct agagatatct gcacgtacgg tagattcgct
3001 gctcttgaat ggatgcaaca gaccagtcga cgtgttgtac gtagacgagg cgtttgcgtg
3061 ccactctgga acgttacttg ctttgatcgc cttggtgaga ccaagacaga aagttgtact
3121 ttgtggtgac ccgaagcagt gcggcttctt caatatgatg cagatgaaag tcaactacaa
3181 tcataacatc tgcacccaag tgtaccacaa aagtatctcc aggcggtgta cactgcctgt
3241 gactgccatt gtgtcatcgt tgcattacga aggcaaaatg cgcactacga atgagtacaa
3301 catgccgatt gtagtggaca ctacaggctc aacgaaacct gaccctggag acctcgtgtt
3361 aacgtgcttc agagggtggg ttaaacaact gcaaattgac tatcgtggac acgaggtcat
3421 gacagcagcc gcatcccaag ggttaactag aaaaggagtt tacgcagtta ggcaaaaagt
3481 taacgaaaac ccactctatg catcaacatc agagcacgtc aacgtactcc taacgcgtac
3541 ggaaggtaaa ctggtatgga agacactctc tggtgacccg tggataaaga cgctgcagaa
3601 cccaccgaaa ggaaacttca aagcaactat taaggagtgg gaggtggagc acgcatcgat
3661 aatggcgggc atctgcagtc accaagtgac ctttgacaca ttccaaaaca aagccaacgt
3721 ttgctgggct aagagcttgg tccctatcct cgaaacagcg ggataaaac taaatgatag
3781 gcagtggtcc cagataattc aagccttcaa agaagacaaa gcatactcac ccgaagtagc
3841 cctgaatgaa atatgcacgc gcatgtatgg ggtggatcta gacagtgggc tattctctaa
3901 accgttggta tctgtgtatt acgcggataa ccattgggat aataggccgg gaggaaagat
3961 gttcggattc aaccctgagg cagcgtccat tctagaaaga aagtacccat ttacaaaagg
4021 aaagtggaac atcaacaagc agatctgcgt gactaccagg aggatagaag acttcaaccc
4081 taccaccaac attataccgg tcaacaggag actaccacac tcattagtgg ccgaacaccg
4141 cccagtaaaa ggggaaagaa tggaatggct ggttaacaag ataaacggac accacgtact
4201 cctggttagc ggctataacc ttgcactgcc tactaagaga gtcacctggg tagcgccact
4261 aggtgtccgc ggagcggact atacatacaa cctagagctg ggtctaccag caacrcttgg
4321 taggtatgac ctagtggtca taaacatcca cacacctttt cgcatacacc attaccaaca
4381 gtgcgtagat cacgcaatga aactgcaaat gctagggggt gactcactga gactgctcaa
4441 accgggtggc tctctattga tcagagcata cggttacgca gatagaacca gtgaacgagt
4501 catctgcgta ctgggacgca agtttagatc gtctagagca ttgaaaccac catgtgtcac
4561 cagtaatact gagatgtttt tcctatttag caattttgac aatggcagaa ggaattttac
4621 aacgcatgtc atgaacaatc aactgaatgc agcctttgta ggacaggcca cccgagcagg
4681 atgtgcacca tcgtaccggg taaaacgcat ggacatcgcg aagaacgatg aagagtgcgt
4741 ggttaacgcc gccaaccctc gcgggttacc aggtgacggt gtttgcaagg cagtatataa
4801 aaagtggccg gagtccttta aaaacagtgc aacaccagta ggaaccgcaa aaacagttat
4861 gtgcggtacg tatccagtaa tccacgccgt aggaccaaac ttctcaaatt attcggagtc
4921 tgaaggggac cgggaattgg cggctgccta tcgagaagtc gcaaaggaag taactagact
4981 gggagtaaat agcgtagcta tacctctcct ctccacaggt gtatactcag gagggaaaga
5041 caggctaacc cagtcactga accacctctt tacagccatg gactcgacgg atgcagacgt
5101 ggtcatctac tgccgagaca aggaatggga gaagaaaata tctgaggcca tacagatgcg

Figure 5C

```
5161 gacccaagtg gagctgctgg atgagcacat ctccatagac tgcgatgtca ttcgcgtgca
5221 ccctgacagt agcttggcag gcagaaaagg atacagcacc acggaaggcg cactgtattc
5281 atatctagaa gggacacgtt ttcaccagac ggcagtggat atggcagaga tatacactat
5341 gtggccaaag caaacagagg ccaatgagca agtctgccta tatgccctgg gggaaagtat
5401 tgaatcaatc aggcagaaat gcccggtgga tgatgcagac gcatcatctc ccccgaaaac
5461 tgtcccgtgt ctttgccggt atgccatgac tcctgaacgc gtcacccgac ttcgcatgaa
5521 ccatgtcaca aatataattg tgtgttcttc atttcccctt ccaaagtaca agatagaagg
5581 agtgcaaaaa gtcaaatgct ccaaggtaat gttattcgat cacaatgtgc catcgcgcgt
5641 aagtccaagg gaatacagat cttcccagga gtctgtacag gaagtgagta cgacaacgtc
5701 attgacgcat agccagtttg atctaagcgc cgatggcgag acactgcctg tcccgtcaga
5761 cctggatgct gacgccccag ccctagaacc ggccctagac gacggggcgg tacatacatt
5821 accaaccata atcggaaacc ttgcggccgt gtctgactgg gtaatgagca ccgtacctgt
5881 cgcgccgcct agaagaagga gagggagaaa cctgactgtg acatgtgacg agagagaagg
5941 gaatataaca cccatggcta gcgtccgatt ctttagagca gagctgtgtc cggccgtaca
6001 agaaacagcg gagacgcgtg acacagctat ttcccttcag gcaccgccaa gtaccaccat
6061 ggaactgagc catccaccga tctccttcgg agcaccaagc gagacgttcc ccatcacatt
6121 tggggacttc gacgaaggag aaatcgaaag cttgtcttct gagctactaa ctttcggaga
6181 cttcctaccc ggtgaagtgg atgatctgac agatagcgac tggtccacgt gcccagacac
6241 ggacgacgag ttatgactag acagggcagg tgggtatata ttctcgtcgg acactggtcc
6301 aggccattta caacagaagt cggtacgcca gtcagtgctg ccggtaaaca ccctggagga
6361 agtccacgag gagaagtgtt acccacctaa gctggatgaa ttaaaggagc aactactact
6421 taagaaactc caggagagtg cgtccatggc caatagaagc aggtatcagt cacgcaaagt
6481 ggaaaatatg aaagcaacaa tcatccagag actaaagaga ggctgtaaac tgtatttaat
6541 ggcagagacc ccgaaagtcc cgacttatcg gaccatatac ccggcgcctg tgtactcgcc
6601 tccgatcaat gtccgattgt ccaaccccga gtccgcagtg gcagcatgta atgagttctt
6661 agctagaaac tacccaactg tttcatcata ccaaatcacc gacgagtatg atgcatatct
6721 agacatggtg gacgggtcgg agagttgctt ggaccgagcg acattcaatc cgtcaaaact
6781 taggagctac ccgaaacaac atgcttatca cgcgccttct atcagaagcg ctgtaccttc
6841 cccattccag aacacactac agaatgtact ggcagcagcc acgaaaagga actgcaacgt
6901 cacacagatg agggaattac ccactttgga ctcagcagta ttcaacgtgg agtgttttaa
6961 aaaattcgca tgtaaccgag aatactggga agaatttgca gccagcccta tcaggataac
7021 aactgagaat ctaacaacct atgtcactaa actaaagggg ccaaaagcag cagcgctgtt
7081 tgcaaaaacc cataatctgc tgccactgca ggatgtacca atggataggt tcacagtaga
7141 tatgaaaagg gatgtgaagg taactcctgg tacaaagcat acagaggaaa gacctaaggt
7201 gcaggttata caggcggctg aacccttggc aacagcgtac ctatgtggaa ttcacagaga
7261 actggttagg agattgaacg ccgtcctcct acccaatgtg catacactat ttgacatgtc
7321 tgccgaggac ttcgatgcca ttatagccgc acacttcaag ccaggagacg ctgttttaga
7381 aacggacata gcctcctttg ataagagcca agatgattca cttgcgctta ccgccttaat
7441 gctgttagaa gatttgggag tggatcactc cctgttggac ttgatagagg ctgctttcgg
7501 agagatttcc agctgtcatc tgccgacagg tacgcgcttc aagttcggcg ctatgatgaa
7561 atccggtatg ttcctaactc tgttcgtcaa cacgttgtta aatatcacca tcgctagccg
7621 ggtgttggaa gatcgtctga caaaatccgc atgcgcggcc ttcatcggcg acgacaacat
7681 aatacatggt gtcgtctccg atgaattgat ggcagccaga tgcgctactt ggatgaacat
7741 ggaagtgaag atcatagatg cagttgtatc ccagaaagct ccttactttt gtggagggtt
7801 tatactgcat gatactgtga caggaacagc ttgcagagtg gcggacccgc taaaaaggtt
```

Figure 5D 7861 atttaaattg ggcaaaccgt tagcggcagg tgacgaacaa gatgaagaca gaagacgggc
7921 gctggctgat gaagtaatca gatggcaacg aacagggcta atagatgagc tggagaaagc
7981 ggtgtactct aggtacgaag tgcagggtat atcagttgcg gtaatgtcca tggccacctt
8041 tgcaagctcc agatccaact tcgagaagct cagaggaccc gtcataactt tgtacggcgg
8101 tcctaaatag gtacgcacta cagctaccta ttttgcagaa gccgacagca ggtacctaaa
8161 taccaatcag ccataatgga gtttatccca acccaaactt tctacaatag gaggtaccag
8221 cctcgacctt ggactccgcg ccctactatc caagttatca gacccagacc gcgtccgcaa
8281 aggaaagccg ggcaacttgc ccagctgatc tcagcagtta ataaactgac aatgcgcgcg
8341 gtacctcaac agaagccgcg caagaatcgg aagaataaga agcaaaagca aaagcagcag
8401 gcgccacgaa acaacatgaa tcaaaagaag cagcccccta aaaagaaacc ggctcaaaag
8461 aaaaagaagc cgggccgtag agagagaatg tgcatgaaaa tcgaaaatga ttgcatcttc
8521 gaagtcaagc atgaaggtaa ggtaacaggt tacgcgtgct tggtagggga caaagtaatg
8581 aagccagcac acgtaaaggg gaccatcgat aatgcggacc tggccaaatt ggccttcaag
8641 cggtcatcta agtacgacct tgaatgcgcg cagatacccg tgcacatgaa gtccgacgct
8701 tcgaagttca cccatgagaa accggagggg tactacaact ggcaccacgg agcagtacag
8761 tactcaggag gccggttcac catccctaca ggtgcgggca aaccagggga cagcggtaga
8821 ccgatcttcg acaacaaggg gcgcgtggtg gccatagttt taggaggagc taatgaagga
8881 gcccgtacag ccctctcggt ggtgacctgg aacaaagaca tcgtcacgaa aatcacccct
8941 gaggggggccg aagagtggag tcttgccTAG *aggacccgtc ataactttgt acggcggtcc*
*9001 taaataggta cgcactacag ctacctattt tgcagaagcc gacagcaggt acctaaatac*
*9061 caatcagcca* *ta*ATGattcc agttatgtgc ctgctggcaa ataccacgtt cccctgctcc
9121 cagcccccctt gcacaccctg ctgctacgaa aaagagccgg agaaaccct gcgcatgcta
9181 gaagacaacg tcatgagccc cgggtactat cagctgctac aagcatcctt aacatgttct
9241 ccccgccgcc agcgacgcag tattaaggac aacttcaatg tctataaagc cataagaccg
9301 tacctagctc actgtcccga ctgtggagaa gggcactcgt gccatagtcc cgtagcgcta
9361 gaacgcatca gaaacgaagc gacagacggg acgctgaaaa tccaggtttc cttgcaaatc
9421 ggaataaaga cggatgatag ccatgattgg accaagctgc gttacatgga caatcatatg
9481 ccagcagacg cagagagggc caggctattt gtaagaacgt cagcaccgtg cacgattact
9541 ggaacaatgg gacacttcat cctggcccga tgtccgaaag gagaaactct gacggtggga
9601 ttcactgacg gtaggaagat cagtcactca tgtacgcacc catttcacca cgaccctcct
9661 gtgataggcc gggaaaaatt tcattcccga ccgcagcacg gtagagaact accttgcagc
9721 acgtacgcgc agagcaccgc tgcaactgcc gaggagatag aggtacatat gcccccagac
9781 accccagatc gcacattgat gtcacaacag tccggtaatg taaagatcac agtcaatagt
9841 cagacggtgc ggtacaagtg taattgcggt gactcaaatg aaggactaac cactacagac
9901 aaagtgatta ataactgcaa ggttgatcaa tgccatgccg cggtcaccaa tcacaaaaaa
9961 tggcagtata attcccctct ggtcccgcgt aatgctgaac tcggggaccg aaaaggaaaa
10021 gttcacattc cgtttcctct ggcaaatgtg acatgcaggg tgcctaaggc aaggaacccc
10081 accgtgacgt acggaaaaaa ccaagtcatc atgctgctgt atcctgacca cccaacgctc
10141 ctgtcctacc ggaatatggg agaagaacca aactatcaag aagagtgggt gacgcataag
10201 aaggagatca ggttaaccgt gccgactgaa gggctcgagg tcacgtgggg caataacgag
10261 ccgtacaagt attggccgca gttatccaca aacggtacag cccacggcca cccgcatgag
10321 ataattttgt attattatga gctgtaccct actatgactg tggtagttgt gtcagtggcc
10381 tcgttcgtac tcctgtcgat ggtgggtgtg gcagtgggga tgtgcatgtg tgcacgacgc
10441 agatgcatta caccgtacga actgacacca ggagctaccg tccctttcct gcttagccta
10501 atatgctgca ttagaacagc taaagcggcc acataccaag aggctgcggt atacctgtgg

Figure 5E

```
10561 aacgagcagc agcctttgtt ttggctgcaa gcccttattc cgctggcagc cctgattgtc
10621 ctatgcaact gtctgagact cttaccatgc ttttgtaaaa cgttgacttt tttagccgta
10681 atgagcgtcg gtgcccacac tgtgagcgcg tacgaacacg taacagtgat cccgaacacg
10741 gtgggagtac cgtataagac tctagtcaac agacccggct acagccccat ggtactggag
10801 atggagcttc tgtcagtcac tttggagcca acgctatcgc ttgattacat cacgtgcgag
10861 tataaaaccg tcatcccgtc tccgtacgtg aaatgctgcg gtacagcaga gtgcaaggac
10921 aagagcctac ctgattacag ctgtaaggtc ttcaccggcg tctacccatt catgtggggc
10981 ggcgcctact gcttctgcga cactgaaaat acgcaattga gcgaagcaca tgtggagaag
11041 tccgaatcat gcaaaacaga atttgcatca gcatataggg ctcataccgc atccgcatca
11101 gctaagctcc gcgtccttta ccaaggaaat aatgttactg tatctgctta tgcaaacggc
11161 gatcatgccg tcacagttaa ggacgctaaa ttcattgtgg ggccaatgtc ttcagcctgg
11221 acaccttttg acaataaaat cgtggtgtac aaaggcgacg tctacaacat ggactacccg
11281 cccttcggcg caggaagacc aggacaattt ggcgacatcc aaagtcgcac gcctgagagc
11341 gaagacgtct atgctaacac acaactggta ctgcagagac cgtccgcggg tacggtgcac
11401 gtgccgtact ctcaggcacc atctggcttc aagtattggc taaaagaacg aggggcgtcg
11461 ctgcagcaca cagcaccatt tggctgtcaa atagcaacaa acccggtaag agcgatgaac
11521 tgcgccgtag ggaacatgcc tatctccatc gacataccgg acgcggcctt cactagggtc
11581 gtcgacgcgc catctttaac ggacatgtcg tgtgaggtac cagcctgcac ccactcctca
11641 gactttgggg gcgtagccat cattaaatat gcagccagca agaaaggcaa gtgtgcggtg
11701 cattcgatga ctaacgccgt cactattcgg gaagctgaaa tagaagtaga agggaactct
11761 cagttgcaaa tctctttttc gacggcccta gccagcgccg aattccgcgt acaagtctgt
11821 tctacacaag tacactgtgc agccgagtgc catccaccga aagaccatat agtcaattac
11881 ccggcgtcac acaccaccct cggggtccaa gacatttccg ttacggcgat gtcatgggtg
11941 cagaagatca cgggaggtgt gggactggtt gtcgctgttg cagcactgat cctaatcgtg
12001 gtgctatgcg tgtcgtttag caggcactaa cttgacaact aggtacgaag gtatatgtgt
12061 cccctaagag acacaccaca tatagctaag aatcaataga taagtataga tcaaagggct
12121 gaacaacccc tgaatagtaa caaaatataa aaatcaacaa aaatcataaa atagaaaacc
12181 agaaacagaa gtaggtaaga aggtatatgt gtcccctaag agacacacca tatatagcta
12241 agaatcaata gataagtata gatcaaaggg ctgaataacc cctgaataat aacaaaatat
12301 aaaaatcaat aaaaatcata aaatagaaaa ccataaacag aagtagttca aagggctata
12361 aaacccctga atagtaacaa aacataaaac taataaaaat caaatgaata ccataattgg
12421 caatcggaag agatgtaggt acttaagctt cctaaaagca gccgaactcg ctttgagatg
12481 taggcgtagc acaccgaact cttccataat tctccgaacc cacagggacg taggagatgt
12541 tcaaagtggc tataaaaccc tgaacagtaa taaaacataa aattaataag gatcaaatga
12601 gtaccataat tggcaaacgg aagagatgta ggtacttaag cttcctaaaa gcagccgaac
12661 tcactttgag atgtaggcat agcataccga actcttccac aattctccgt acccataggg
12721 acgtaggaga tgttattttg tttttaatat ttcAAAAAAA AAAAAAAAAA AAAAGGGTAC
12781 GCGGCCGCCA CTGTGCTGGA TATCTGCAGA ATTCCACCAC ACTGGACTAG TGGATCAGCT
12841 TAAGTTTAAA CCGCTGATCA GCCTCGACTG TGCCTTCTAG TTGCCAGCCA TCTGTTGTTT
12901 GCCCCTCCCC CGTGCCTTCC TTGACCCTGG AAGGTGCCAC TCCCACTGTC CTTTCCTAAT
12961 AAAATGAGGA AATTGCATCG CATTGTCTGA GTAGGTGTCA TTCTATTCTG GGGGGTGGGG
13021 TGGGGCAGGA C
```

Figures 6A-6E: An i-DNA sequence with a Group D RNA transport element (RTE)-related sequence (highlighted in italics).

Figure 6A

1 GGCGCGCCTG ACATTGATTA TTGACTAGTT ATTAATAGTA ATCAATTACG GGGTCATTAG
61 TTCATAGCCC ATATATGGAG TTCCGCGTTA CATAACTTAC GGTAAATGGC CCGCCTGGCT
121 GACCGCCCAA CGACCCCCGC CCATTGACGT CAATAATGAC GTATGTTCCC ATAGTAACGC
181 CAATAGGGAC TTTCCATTGA CGTCAATGGG TGGAGTATTT ACGGTAAACT GCCCACTTGG
241 CAGTACATCA AGTGTATCAT ATGCCAAGTA CGCCCCCTAT TGACGTCAAT GACGGTAAAT
301 GGCCCGCCTG GCATTATGCC CAGTACATGA CCTTATGGGA CTTTCCTACT TGGCAGTACA
361 TCTACGTATT AGTCATCGCT ATTACCATGG TGATGCGGTT TTGGCAGTAC ATCAATGGGC
421 GTGGATAGCG GTTTGACTCA CGGGGATTTC CAAGTCTCCA CCCCATTGAC GTCAATGGGA
481 GTTTGTTTTG GCACCAAAAT CAACGGGACT TTCCAAAATG TCGTAACAAC TCCGCCCCAT
541 TGACGCAAAT GGGCGGTAGG CGTGTACGGT GGGAGGTCTA TATAAGCAGA GCTCTCTGGC
601 TAACTAGAGa tggctgcgtg agacacacgt agcctaccag tttcttactg ctctactctg
661 caaagcaaga gattaataac ccatcatgga ttctgtgtac gtggacatag acgctgacag
721 cgccttttttg aaggccctgc aacgtgcgta ccccatgttt gaggtggaac ctaggcaggt
781 cacatcgaat gaccatgcta atgctagagc gttctcgcat ctagccataa aactaataga
841 gcaggaaatt gatcccgact caaccatcct ggatataggt agtgcgccag caaggaggat
901 gatgtcggac aggaagtacc actgcgtttg cccgatgcgc agcgcagaag atcccgagag
961 actcgctaat tatgcgagaa agctcgcatc tgccgcagga aaagtcctgg acagaaacat
1021 ttctggaaag atcggggact tacaagcggt gatggccgtg ccagacacgg agacgccaac
1081 attttgctta cacacagatg tctcatgtag acagagagca gacgtcgcga tataccaaga
1141 cgtctatgct gtacacgcac ccacgtcgct ataccaccag gcgattaaag gagtccgagt
1201 ggcgtactgg gtagggttcg acacaacccc gttcatgtac aacgctatgg cgggtgccta
1261 cccctcatac tcgacaaatt gggcggatga gcaggtactg aaggctaaga acataggatt
1321 atgttcaaca gacctgacgg aaggtagacg aggcaaattg tctatcatga gagggaaaaa
1381 gctaaaaccg tgcgaccgtg tgctgttctc agtagggtca acgctttacc cggaaagccg
1441 cacgctactt aagagctggc acctaccatc ggtgttccat ctaaagggca agcttagctt
1501 cacatgccgc tgtgacacag tggtttcgtg tgagggctac gtcgttaaga gaataacgat
1561 gagcccaggc ctttatggaa aaaccatagg gtatgcggta acccaccacg cagacggatt
1621 cttgatgtgc aagactaccg acacggttga cggcgaaaga gtgtcattct cggtgtgcac
1681 gtacgtgccg gcgaccattt gtgatcaaat gaccggcatc cttgctacag aagtcacgcc
1741 ggaggatgca cagaagctgt tggtggggct gaaccagagg atagtggtta acggcagaac
1801 gcaacggaac acgaacacca tgaagaacta cctacttccc gtggtcgccc aggccttcag
1861 taagtgggca aaggagtgcc ggaaggacat ggaagatgag aagcttctgg gggtcagaga
1921 aagaacacta acctgctgct gtctatgggc atttaagaag cagaaaacac acacggtcta
1981 caagaggcct gatacccagt caatccagaa ggttcaggcc gaatttgaca gctttgtagt
2041 accgggcctg tggtcgtccg ggttgtcaat cccgttgagg actagaatca agtggttgtt
2101 acgcaaggtg ccgaaaacag acctgatccc atacagcggg aatgcccaag aagcccagga
2161 tgcagaaaaa gaagcagagg aagaacgaga agcagaactg actcatgagg ctctaccacc
2221 cctacaggca gcacaggaag atgtccaggt cgaaatcgac gtggaacagc ttgaggatag
2281 agctggtgct ggaataatag agactccgag aggcgctatc aaagttactg cccaactaac
2341 agaccacgtc gtgggggagt acctggtact ttccccgcag accgtactac gcagccagaa
2401 gctcagcctg atccacgctt tagcggagca agtgaagacg tgtacgcaca gcggacgagc

Figure 6B 2461 agggaggtat gcggtcgaag cgtacgatgg ccgagtccta gtgccctcag gctatgcaat
2521 ttcgcctgaa gacttccaga gtctaagcga aagcgcaacg atggtgtaca acgaaagaga
2581 gttcgtaaac agaaagttac accacattgc gatgcacgga ccagccctga acactgacga
2641 agagtcgtat gagctggtga gggcagagag gacagaacac gagtacgtct acgacgtgga
2701 ccagagaaga tgctgtaaga aggaagaagc tgcaggactg gtactggtgg gcgacttgac
2761 taatccgccc taccacgaat tcgcatacga agggctaaaa attcgccccg cctgcccata
2821 caaaattgca gtcataggag tcttcggggt accaggatct ggcaagtcag ccattatcaa
2881 gaacctagtt accaggcaag acctggtgac tagcggaaag aaagaaaact gccaagaaat
2941 cagcaccgac gtgatgagac agagaggtct agagatatct gcacgtacgg tagattcgct
3001 gctcttgaat ggatgcaaca gaccagtcga cgtgttgtac gtagacgagg cgtttgcgtg
3061 ccactctgga acgttacttg ctttgatcgc cttggtgaga ccaagacaga aagttgtact
3121 ttgtggtgac ccgaagcagt gcggcttctt caatatgatg cagatgaaag tcaactacaa
3181 tcataacatc tgcacccaag tgtaccacaa aagtatctcc aggcggtgta cactgcctgt
3241 gactgccatt gtgtcatcgt tgcattacga aggcaaaatg cgcactacga atgagtacaa
3301 catgccgatt gtagtggaca ctacaggctc aacgaaacct gaccctggag acctcgtgtt
3361 aacgtgcttc agagggtggg ttaaacaact gcaaattgac tatcgtggac acgaggtcat
3421 gacagcagcc gcatcccaag ggttaactag aaaaggagtt tacgcagtta ggcaaaaagt
3481 taacgaaaac ccactctatg catcaacatc agagcacgtc aacgtactcc taacgcgtac
3541 ggaaggtaaa ctggtatgga agacactctc tggtgacccg tggataaaga cgctgcagaa
3601 cccaccgaaa ggaaacttca aagcaactat taaggagtgg gaggtggagc acgcatcgat
3661 aatggcgggc atctgcagtc accaagtgac ctttgacaca ttccaaaaca aagccaacgt
3721 ttgctgggct aagagcttgg tccctatcct cgaaacagcg ggataaaac taaatgatag
3781 gcagtggtcc cagataattc aagccttcaa agaagacaaa gcatactcac ccgaagtagc
3841 cctgaatgaa atatgcacgc gcatgtatgg ggtggatcta gacagtgggc tattctctaa
3901 accgttggta tctgtgtatt acgcggataa ccattgggat aataggccgg gaggaaagat
3961 gttcggattc aaccctgagg cagcgtccat tctagaaaga aagtacccat ttacaaaagg
4021 aaagtggaac atcaacaagc agatctgcgt gactaccagg aggatagaag acttcaaccc
4081 taccaccaac attataccgg tcaacaggag actaccacac tcattagtgg ccgaacaccg
4141 cccagtaaaa ggggaaagaa tggaatggct ggttaacaag ataaacggac accacgtact
4201 cctggttagc ggctataacc ttgcactgcc tactaagaga gtcacctggg tagcgccact
4261 aggtgtccgc ggagcggact atacatacaa cctagagctg ggtctaccag caacrcttgg
4321 taggtatgac ctagtggtca taaacatcca cacacctttt cgcatacacc attaccaaca
4381 gtgcgtagat cacgcaatga aactgcaaat gctagggggt gactcactga gactgctcaa
4441 accgggtggc tctctattga tcagagcata cggttacgca gatagaacca gtgaacgagt
4501 catctgcgta ctgggacgca agtttagatc gtctagagca ttgaaaccac catgtgtcac
4561 cagtaatact gagatgtttt tcctatttag caattttgac aatggcagaa ggaattttac
4621 aacgcatgtc atgaacaatc aactgaatgc agcctttgta ggacaggcca cccgagcagg
4681 atgtgcacca tcgtaccggg taaaacgcat ggacatcgcg aagaacgatg aagagtgcgt
4741 ggttaacgcc gccaaccctc gcgggttacc aggtgacggt gtttgcaagg cagtatataa
4801 aaagtggccg gagtccttta aaaacagtgc aacaccagta ggaaccgcaa aaacagttat
4861 gtgcggtacg tatccagtaa tccacgccgt aggaccaaac ttctcaaatt attcggagtc
4921 tgaaggggac cgggaattgg cggctgccta tcgagaagtc gcaaaggaag taactagact
4981 gggagtaaat agcgtagcta tacctctcct ctccacaggt gtatactcag gagggaaaga
5041 caggctaacc cagtcactga accacctctt tacagccatg gactcgacgg atgcagacgt
5101 ggtcatctac tgccgagaca aggaatggga gaagaaaata tctgaggcca tacagatgcg

Figure 6C

```
5161 gacccaagtg gagctgctgg atgagcacat ctcccatagac tgcgatgtca ttcgcgtgca
5221 ccctgacagt agcttggcag gcagaaaagg atacagcacc acggaaggcg cactgtattc
5281 atatctagaa gggacacgtt ttcaccagac ggcagtggat atggcagaga tatacactat
5341 gtggccaaag caaacagagg ccaatgagca agtctgccta tatgccctgg gggaaagtat
5401 tgaatcaatc aggcagaaat gcccggtgga tgatgcagac gcatcatctc ccccgaaaac
5461 tgtcccgtgt ctttgccggt atgccatgac tcctgaacgc gtcacccgac ttcgcatgaa
5521 ccatgtcaca aatataattg tgtgttcttc atttcccctt ccaaagtaca agatagaagg
5581 agtgcaaaaa gtcaaatgct ccaaggtaat gttattcgat cacaatgtgc catcgcgcgt
5641 aagtccaagg gaatacagat cttcccagga gtctgtacag gaagtgagta cgacaacgtc
5701 attgacgcat agccagtttg atctaagcgc cgatggcgag acactgcctg tcccgtcaga
5761 cctggatgct gacgccccag ccctagaacc ggccctagac gacggggcgg tacatacatt
5821 accaaccata atcggaaacc ttgcggccgt gtctgactgg gtaatgagca ccgtacctgt
5881 cgcgccgcct agaagaagga gagggagaaa cctgactgtg acatgtgacg agagagaagg
5941 gaatataaca cccatggcta gcgtccgatt ctttagagca gagctgtgtc cggccgtaca
6001 agaaacagcg gagacgcgtg acacagctat ttcccttcag gcaccgccaa gtaccaccat
6061 ggaactgagc catccaccga tctccttcgg agcaccaagc gagacgttcc ccatcacatt
6121 tggggacttc gacgaaggag aaatcgaaag cttgtcttct gagctactaa ctttcggaga
6181 cttcctaccc ggtgaagtgg atgatctgac agatagcgac tggtccacgt gcccagacac
6241 ggacgacgag ttatgactag acagggcagg tgggtatata ttctcgtcgg acactggtcc
6301 aggccattta caacagaagt cggtacgcca gtcagtgctg ccggtaaaca ccctggagga
6361 agtccacgag gagaagtgtt acccacctaa gctggatgaa ttaaaggagc aactactact
6421 taagaaactc caggagagtg cgtccatggc caatagaagc aggtatcagt cacgcaaagt
6481 ggaaaatatg aaagcaacaa tcatccagag actaaagaga ggctgtaaac tgtatttaat
6541 ggcagagacc ccgaaagtcc cgacttatcg gaccatatac ccggcgcctg tgtactcgcc
6601 tccgatcaat gtccgattgt ccaaccccga gtccgcagtg gcagcatgta atgagttctt
6661 agctagaaac tacccaactg tttcatcata ccaaatcacc gacgagtatg atgcatatct
6721 agacatggtg gacgggtcgg agagttgctt ggaccgagcg acattcaatc cgtcaaaact
6781 taggagctac ccgaaacaac atgcttatca cgcgccttct atcagaagcg ctgtaccttc
6841 cccattccag aacacactac agaatgtact ggcagcagcc acgaaaagga actgcaacgt
6901 cacacagatg agggaattac ccactttgga ctcagcagta ttcaacgtgg agtgtttaa
6961 aaaattcgca tgtaaccgag aatactggga agaatttgca gccagcccta tcaggataac
7021 aactgagaat ctaacaacct atgtcactaa actaaagggg ccaaaagcag cagcgctgtt
7081 tgcaaaaacc cataatctgc tgccactgca ggatgtacca atggataggt tcacagtaga
7141 tatgaaaagg gatgtgaagg taactcctgg tacaaagcat acagaggaaa gacctaaggt
7201 gcaggttata caggcggctg aacccttggc aacagcgtac ctatgtggaa ttcacagaga
7261 actggttagg agattgaacg ccgtcctcct acccaatgtg catacactat ttgacatgtc
7321 tgccgaggac ttcgatgcca ttatagccgc acacttcaag ccaggagacg ctgttttaga
7381 aacggacata gcctcctttg ataagagcca agatgattca cttgcgctta ccgccttaat
7441 gctgttagaa gatttgggag tggatcactc cctgttggac ttgatagagg ctgctttcgg
7501 agagatttcc agctgtcatc tgccgacagg tacgcgcttc aagttcggcg ctatgatgaa
7561 atccggtatg ttcctaactc tgttcgtcaa cacgttgtta aatatcacca tcgctagccg
7621 ggtgttggaa gatcgtctga caaaatccgc atgcgcggcc ttcatcggcg acgacaacat
7681 aatacatggt gtcgtctccg atgaattgat ggcagccaga tgcgctactt ggatgaacat
7741 ggaagtgaag atcatagatg cagttgtatc ccagaaagct ccttactttt gtggagggtt
7801 tatactgcat gatactgtga caggaacagc ttgcagagtg gcggacccgc taaaaaggtt
```

Figure 6D

```
 7861 atttaaattg ggcaaaccgt tagcggcagg tgacgaacaa gatgaagaca gaagacgggc
 7921 gctggctgat gaagtaatca gatggcaacg aacagggcta atagatgagc tggagaaagc
 7981 ggtgtactct aggtacgaag tgcagggtat atcagttgcg gtaatgtcca tggccacctt
 8041 tgcaagctcc agatccaact tcgagaagct cagaggaccc gtcataactt tgtacggcgg
 8101 tcctaaatag gtacgcacta cagctaccta ttttgcagaa gccgacagca ggtacctaaa
 8161 taccaatcag ccataatgga gtttatccca acccaaactt tctacaatag gaggtaccag
 8221 cctcgacctt ggactccgcg ccctactatc caagttatca gacccagacc gcgtccgcaa
 8281 aggaaagccg ggcaacttgc ccagctgatc tcagcagtta ataaactgac aatgcgcgcg
 8341 gtacctcaac agaagccgcg caagaatcgg aagaataaga agcaaaagca aaagcagcag
 8401 gcgccacgaa acaacatgaa tcaaaagaag cagcccccta aaaagaaacc ggctcaaaag
 8461 aaaaagaagc cgggccgtag agagagaatg tgcatgaaaa tcgaaaatga ttgcatcttc
 8521 gaagtcaagc atgaaggtaa ggtaacaggt tacgcgtgct tggtagggga caaagtaatg
 8581 aagccagcac acgtaaaggg gaccatcgat aatgcggacc tggccaaatt ggccttcaag
 8641 cggtcatcta agtacgacct tgaatgcgcg cagatacccg tgcacatgaa gtccgacgct
 8701 tcgaagttca cccatgagaa accggagggg tactacaact ggcaccacgg agcagtacag
 8761 tactcaggag gccggttcac catccctaca ggtgcgggca aaccagggga cagcggtaga
 8821 ccgatcttcg acaacaaggg gcgcgtggtg gccatagttt taggaggagc taatgaagga
 8881 gcccgtacag ccctctcggt ggtgacctgg aacaaagaca tcgtcacgaa aatcacccct
 8941 gagggggccg aagagtggag tcttgccatt ccagttatgt gcctgctggc aaataccacg
 9001 ttcccctgct cccagccccc ttgcacaccc tgctgctacg aaaaagagcc ggagaaaacc
 9061 ctgcgcatgc tagaagacaa cgtcatgagc cccgggtact atcagctgct acaagcatcc
 9121 ttaacatgtt ctccccgccg ccagcgacgc agtattaagg acaacttcaa tgtctataaa
 9181 gccataagac cgtacctagc tcactgtccc gactgtggag aagggcactc gtgccatagt
 9241 cccgtagcgc tagaacgcat cagaaacgaa gcgacagacg ggacgctgaa aatccaggtt
 9301 tccttgcaaa tcggaataaa gacggatgat agccatgatt ggaccaagct gcgttacatg
 9361 gacaatcata tgccagcaga cgcagagagg gccaggctat ttgtaagaac gtcagcaccg
 9421 tgcacgatta ctggaacaat gggacacttc atcctggccc gatgtccgaa aggagaaact
 9481 ctgacggtgg gattcactga cggtaggaag atcagtcact catgtacgca cccatttcac
 9541 cacgaccctc ctgtgatagg ccgggaaaaa tttcattccc gaccgcagca cggtagagaa
 9601 ctaccttgca gcacgtacgc gcagagcacc gctgcaactg ccgaggagat agaggtacat
 9661 atgcccccag acaccccaga tcgcacattg atgtcacaac agtccggtaa tgtaaagatc
 9721 acagtcaata gtcagacggt gcggtacaag tgtaattgcg gtgactcaaa tgaaggacta
 9781 accactacag acaaagtgat taataactgc aaggttgatc aatgccatgc cgcggtcacc
 9841 aatcacaaaa aatggcagta taattcccct ctggtcccgc gtaatgctga actcggggac
 9901 cgaaaaggaa aagttcacat tccgtttcct ctggcaaatg tgacatgcag ggtgcctaag
 9961 gcaaggaacc ccaccgtgac gtacggaaaa aaccaagtca tcatgctgct gtatcctgac
10021 cacccaacgc tcctgtccta ccggaatatg ggagaagaac caaactatca agaagagtgg
10081 gtgacgcata agaaggagat caggttaacc gtgccgactg aagggctcga ggtcacgtgg
10141 ggcaacaacg agccgtacaa gtattggccg cagttatcca caaacggtac agcccacggc
10201 cacccgcatg agataatttt gtattattat gagctgtacc ctactatgac tgtggtagtt
10261 gtgtcagtgg cctcgttcgt actcctgtcg atggtgggtg tggcagtggg gatgtgcatg
10321 tgtgcacgac gcagatgcat tacaccgtac gaactgacac caggagctac cgtccctttc
10381 ctgcttagcc taatatgctg cattagaaca gctaaagcgg ccacatacca agaggctgcg
10441 gtatacctgt ggaacgagca gcagcctttg ttttggctgc aagcccttat tccgctggca
10501 gccctgattg tcctatgcaa ctgtctgaga ctcttaccat gcttttgtaa aacgttgact
```

Figure 6E 10561 tttttagccg taatgagcgt cggtgcccac actgtgagcg cgtacgaaca cgtaacagtg
10621 atcccgaaca cggtgggagt accgtataag actctagtca acagaccggg ctacagcccc
10681 atggtactgg agatggagct tctgtcagtc actttggagc caacgctatc gcttgattac
10741 atcacgtgcg agtataaaac cgtcatcccg tctccgtacg tgaaatgctg cggtacagca
10801 gagtgcaagg acaagagcct acctgattac agctgtaagg tcttcaccgg cgtctaccca
10861 ttcatgtggg gcggcgccta ctgcttctgc gacactgaaa atacgcaatt gagcgaagca
10921 catgtggaga agtccgaatc atgcaaaaca gaatttgcat cagcatatag ggctcatacc
10981 gcatccgcat cagctaagct ccgcgtcctt taccaaggaa ataatgttac tgtatctgct
11041 tatgcaaacg gcgatcatgc cgtcacagtt aaggacgcta aattcattgt ggggccaatg
11101 tcttcagcct ggacaccttt tgacaataaa atcgtggtgt acaaaggcga cgtctacaac
11161 atggactacc cgcccttcgg cgcaggaaga ccaggacaat ttggcgacat ccaaagtcgc
11221 acgcctgaga gcgaagacgt ctatgctaac acacaactgg tactgcagag accgtccgcg
11281 ggtacggtgc acgtgccgta ctctcaggca ccatctggct tcaagtattg gctaaaagaa
11341 cgaggggcgt cgctgcagca cacagcacca tttggctgtc aaatagcaac aaacccggta
11401 agagcgatga actgcgccgt agggaacatg cctatctcca tcgacatacc ggacgcggcc
11461 ttcactaggg tcgtcgacgc gccatcttta acggacatgt cgtgtgaggt accagcctgc
11521 acccactcct cagactttgg gggcgtagcc atcattaaat atgcagccag caagaaaggc
11581 aagtgtgcgg tgcattcgat gactaacgcc gtcactattc gggaagctga aatagaagta
11641 gaagggaact ctcagttgca aatctctttt tcgacggccc tagccagcgc cgaattccgc
11701 gtacaagtct gttctacaca agtacactgt gcagccgagt gccatccacc gaaagaccat
11761 atagtcaatt acccggcgtc acacaccacc ctcggggtcc aagacatttc cgttacggcg
11821 atgtcatggg tgcagaagat cacgggaggt gtgggactgg ttgtcgctgt tgcagcactg
11881 atcctaatcg tggtgctatg cgtgtcgttt agcaggcact aacttgacaa ctaggtacga
11941 aggtatatgt gtcccctaag agacacacca catatagcta agaatcaata gataagtata
12001 gatcaaaggg ctgaacaacc cctgaatagt aacaaaatat aaaaatcaac aaaaatcata
12061 aaatagaaaa ccagaaacag aagtaggtaa gaaggtatat gtgtccccta agagacacac
12121 catatatagc taagaatcaa tagataagta tagatcaaag ggctgaataa cccctgaata
12181 ataacaaaat ataaaaatca ataaaaatca taaaatagaa aaccataaac agaagtagtt
12241 caaagggcta taaaacccct gaatagtaac aaaacataaa actaataaaa atcaaatgaa
12301 taccataatt ggcaatcgga agagatgtag gtacttaagc ttcctaaaag cagccgaact
12361 cgctttgaga tgtaggcgta gcacaccgaa ctcttccata attctccgaa cccacaggga
12421 cgtaggagat gttcaaagtg gctataaaac cctgaacagt aataaaacat aaaattaata
12481 aggatcaaat gagtaccata attggcaaac ggaagagatg taggtactta agcttcctaa
12541 aagcagccga actcactttg agatgtaggc atagcatacc gaactcttcc acaattctcc
12601 gtacccatag ggacgtagga gatgttattt tgttttaat atttc*gagag agttgcaagg*
*12661 ctaagcactg caatggaaag gctctgcggc atatatgagc ctattctagg gagacatgtc*
*12721 atctttcatg aaggttcagt gtcctagttc ccttccccca ggcaaaacga cacgggagca*
*12781 ggtcagggtt gctctgggta aaagcctgta agcctaagag ctaatcctgt acatggctcc*
*12841 tttacctaca cactggggat ttgacctcta tctccactct catta*AAAAA AAAAAAAAAA
12901 AAAAAAGGGT ACGCGGCCGC CACTGTGCTG GATATCTGCA GAATTCCACC ACACTGGACT
12961 AGTGGATCAG CTTAAGTTTA AACCGCTGAT CAGCCTCGAC TGTGCCTTCT AGTTGCCAGC
13021 CATCTGTTGT TTGCCCCTCC CCCGTGCCTT CCTTGACCCT GGAAGGTGCC ACTCCCACTG
13081 TCCTTTCCTA ATAAAATGAG GAAATTGCAT CGCATTGTCT GAGTAGGTGT CATTCTATTC
13141 TGGGGGGTGG GGTGGGGCAG GAC Figures 7A-7E: An i-DNA sequence encoding a chimeric vaccine containing structural polyprotein of CHIKV within TC-83 iDNA (highlighted in italics).

Figure 7A

1 GGCGCGCCTG ACATTGATTA TTGACTAGTT ATTAATAGTA ATCAATTACG GGGTCATTAG
61 TTCATAGCCC ATATATGGAG TTCCGCGTTA CATAACTTAC GGTAAATGGC CCGCCTGGCT
121 GACCGCCCAA CGACCCCCGC CCATTGACGT CAATAATGAC GTATGTTCCC ATAGTAACGC
181 CAATAGGGAC TTTCCATTGA CGTCAATGGG TGGAGTATTT ACGGTAAACT GCCCACTTGG
241 CAGTACATCA AGTGTATCAT ATGCCAAGTA CGCCCCCTAT TGACGTCAAT GACGGTAAAT
301 GGCCCGCCTG GCATTATGCC CAGTACATGA CCTTATGGGA CTTTCCTACT TGGCAGTACA
361 TCTACGTATT AGTCATCGCT ATTACCATGG TGATGCGGTT TTGGCAGTAC ATCAATGGGC
421 GTGGATAGCG GTTTGACTCA CGGGGATTTC CAAGTCTCCA CCCCATTGAC GTCAATGGGA
481 GTTTGTTTTG GCACCAAAAT CAACGGGACT TTCCAAAATG TCGTAACAAC TCCGCCCCAT
541 TGACGCAAAT GGGCGGTAGG CGTGTACGGT GGGAGGTCTA TATAAGCAGA GCTCTCTGGC
601 TAACTAGAGA TAGGCGGCGC ATGAGAGAAG CCCAGACCAA TTACCTACCC AAAATGGAGA
661 AAGTTCACGT TGACATCGAG GAAGACAGCC CATTCCTCAG AGCTTTGCAG CGGAGCTTCC
721 CGCAGTTTGA GGTAGAAGCC AAGCAGGTCA CTGATAATGA CCATGCTAAT GCCAGAGCGT
781 TTTCGCATCT GGCTTCAAAA CTGATCGAAA CGGAGGTGGA CCCATCCGAC ACGATCCTTG
841 ACATTGGAAG TGCGCCCGCC CGCAGAATGT ATTCTAAGCA CAAGTATCAT TGTATCTGTC
901 CGATGAGATG TGCGGAAGAT CCGGACAGAT TGTATAAGTA TGCAACTAAG CTGAAGAAAA
961 ACTGTAAGGA AATAACTGAT AAGGAATTGG ACAAGAAAAT GAAGGAGCTC GCCGCCGTCA
1021 TGAGCGACCC TGACCTGGAA ACTGAGACTA TGTGCCTCCA CGACGACGAG TCGTGTCGCT
1081 ACGAAGGGCA AGTCGCTGTT TACCAGGATG TATACGCGGT TGACGGACCG ACAAGTCTCT
1141 ATCACCAAGC CAATAAGGGA GTTAGAGTCG CCTACTGGAT AGGCTTTGAC ACCACCCCTT
1201 TTATGTTTAA GAACTTGGCT GGAGCATATC CATCATACTC TACCAACTGG GCCGACGAAA
1261 CCGTGTTAAC GGCTCGTAAC ATAGGCCTAT GCAGCTCTGA CGTTATGGAG CGGTCACGTA
1321 GAGGGATGTC CATTCTTAGA AAGAAGTATT TGAAACCATC CAACAATGTT CTATTCTCTG
1381 TTGGCTCGAC CATCTACCAC GAGAAGAGGG ACTTACTGAG GAGCTGGCAC CTGCCGTCTG
1441 TATTTCACTT ACGTGGCAAG CAAAATTACA CATGTCGGTG TGAGACTATA GTTAGTTGCG
1501 ACGGGTACGT CGTTAAAAGA ATAGCTATCA GTCCAGGCCT GTATGGGAAG CCTTCAGGCT
1561 ATGCTGCTAC GATGCACCGC GAGGGATTCT TGTGCTGCAA AGTGACAGAC ACATTGAACG
1621 GGGAGAGGGT CTCTTTTCCC GTGTGCACGT ATGTGCCAGC TACATTGTGT GACCAAATGA
1681 CTGGCATACT GGCAACAGAT GTCAGTGCGG ACGACGCGCA AAAACTGCTG GTTGGGCTCA
1741 ACCAGCGTAT AGTCGTCAAC GGTCGCACCC AGAGAAACAC CAATACCATG AAAAATTACC
1801 TTTTGCCCGT AGTGGCCCAG GCATTTGCTA GGTGGGCAAA GGAATATAAG GAAGATCAAG
1861 AAGATGAAAG GCCACTAGGA CTACGAGATA GACAGTTAGT CATGGGGTGT TGTTGGGCTT
1921 TTAGAAGGCA CAAGATAACA TCTATTTATA AGCGCCCGGA TACCCAAACC ATCATCAAAG
1981 TGAACAGCGA TTTCCACTCA TTCGTGCTGC CCAGGATAGG CAGTAACACA TTGGAGATCG
2041 GGCTGAGAAC AAGAATCAGG AAAATGTTAG AGGAGCACAA GGAGCCGTCA CCTCTCATTA
2101 CCGCCGAGGA CGTACAAGAA GCTAAGTGCG CAGCCGATGA GGCTAAGGAG GTGCGTGAAG
2161 CCGAGGAGTT GCGCGCAGCT CTACCACCTT TGGCAGCTGA TGTTGAGGAG CCCACTCTGG
2221 AAGCCGATGT CGACTTGATG TTACAAGAGG CTGGGGCCGG CTCAGTGGAG ACACCTCGTG
2281 GCTTGATAAA GGTTACCAGC TACGCTGGCG AGGACAAGAT CGGCTCTTAC GCTGTGCTTT
2341 CTCCGCAGGC TGTACTCAAG AGTGAAAAAT TATCTTGCAT CCACCCTCTC GCTGAACAAG

Figure 7B

2401 TCATAGTGAT AACACACTCT GGCCGAAAAG GGCGTTATGC CGTGGAACCA TACCATGGTA
2461 AAGTAGTGGT GCCAGAGGGA CATGCAATAC CCGTCCAGGA CTTTCAAGCT CTGAGTGAAA
2521 GTGCCACCAT TGTGTACAAC GAACGTGAGT TCGTAAACAG GTACCTGCAC CATATTGCCA
2581 CACATGGAGG AGCGCTGAAC ACTGATGAAG AATATTACAA AACTGTCAAG CCCAGCGAGC
2641 ACGACGGCGA ATACCTGTAC GACATCGACA GGAAACAGTG CGTCAAGAAA GAACTAGTCA
2701 CTGGGCTAGG GCTCACAGGC GAGCTGGTGG ATCCTCCCTT CCATGAATTC GCCTACGAGA
2761 GTCTGAGAAC ACGACCAGCC GCTCCTTACC AAGTACCAAC CATAGGGGTG TATGGCGTGC
2821 CAGGATCAGG CAAGTCTGGC ATCATTAAAA GCGCAGTCAC CAAAAAAGAT CTAGTGGTGA
2881 GCGCCAAGAA AGAAAACTGT GCAGAAATTA TAAGGGACGT CAAGAAAATG AAAGGGCTGG
2941 ACGTCAATGC CAGAACTGTG GACTCAGTGC TCTTGAATGG ATGCAAACAC CCCGTAGAGA
3001 CCCTGTATAT TGACGAAGCT TTTGCTTGTC ATGCAGGTAC TCTCAGAGCG CTCATAGCCA
3061 TTATAAGACC TAAAAAGGCA GTGCTCTGCG GGGATCCCAA ACAGTGCGGT TTTTTTAACA
3121 TGATGTGCCT GAAAGTGCAT TTTAACCACG AGATTTGCAC ACAAGTCTTC CACAAAAGCA
3181 TCTCTCGCCG TTGCACTAAA TCTGTGACTT CGGTCGTCTC AACCTTGTTT TACGACAAAA
3241 AAATGAGAAC GACGAATCCG AAAGAGACTA AGATTGTGAT TGACACTACC GGCAGTACCA
3301 AACCTAAGCA GGACGATCTC ATTCTCACTT GTTTCAGAGG GTGGGTGAAG CAGTTGCAAA
3361 TAGATTACAA AGGCAACGAA ATAATGACGG CAGCTGCCTC TCAAGGGCTG ACCCGTAAAG
3421 GTGTGTATGC CGTTCGGTAC AAGGTGAATG AAAATCCTCT GTACGCACCC ACCTCAGAAC
3481 ATGTGAACGT CCTACTGACC CGCACGGAGG ACCGCATCGT GTGGAAAACA CTAGCCGGCG
3541 ACCCATGGAT AAAAACACTG ACTGCCAAGT ACCCTGGGAA TTTCACTGCC ACGATAGAGG
3601 AGTGGCAAGC AGAGCATGAT GCCATCATGA GGCACATCTT GGAGAGACCG GACCCTACCG
3661 ACGTCTTCCA GAATAAGGCA AACGTGTGTT GGGCCAAGGC TTTAGTGCCG GTGCTGAAGA
3721 CCGCTGGCAT AGACATGACC ACTGAACAAT GGAACACTGT GGATTATTTT GAAACGGACA
3781 AAGCTCACTC AGCAGAGATA GTATTGAACC AACTATGCGT GAGGTTCTTT GGACTCGATC
3841 TGGACTCCGG TCTATTTTCT GCACCCACTG TTCCGTTATC CATTAGGAAT AATCACTGGG
3901 ATAACTCCCC GTCGCCTAAC ATGTACGGGC TGAATAAAGA AGTGGTCCGT CAGCTCTCTC
3961 GCAGGTACCC ACAACTGCCT CGGGCAGTTG CCACTGGAAG AGTCTATGAC ATGAACACTG
4021 GTACACTGCG CAATTATGAT CCGCGCATAA ACCTAGTACC TGTAAACAGA AGACTGCCTC
4081 ATGCTTTAGT CCTCCACCAT AATGAACACC CACAGAGTGA CTTTTCTTCA TTCGTCAGCA
4141 AATTGAAGGG CAGAACTGTC CTGGTGGTCG GGGAAAAGTT GTCCGTCCCA GGCAAAATGG
4201 TTGACTGGTT GTCAGACCGG CCTGAGGCTA CCTTCAGAGC TCGGCTGGAT TTAGGCATCC
4261 CAGGTGATGT GCCCAAATAT GACATAATAT TTGTTAATGT GAGGACCCCA TATAAATACC
4321 ATCACTATCA GCAGTGTGAA GACCATGCCA TTAAGCTTAG CATGTTGACC AAGAAAGCTT
4381 GTCTGCATCT GAATCCCGGC GGAACCTGTG TCAGCATAGG TTATGGTTAC GCTGACAGGG
4441 CCAGCGAAAG CATCATTGGT GCTATAGCGC GGCAGTTCAA GTTTTCCCGG GTATGCAAAC
4501 CGAAATCCTC ACTTGAAGAG ACGGAAGTTC TGTTTGTATT CATTGGGTAC GATCGCAAGG
4561 CCCGTACGCA CAATCCTTAC AAGCTTTCAT CAACCTTGAC CAACATTTAT ACAGGTTCCA
4621 GACTCCACGA AGCCGGATGT GCACCCTCAT ATCATGTGGT GCGAGGGGAT ATTGCCACGG
4681 CCACCGAAGG AGTGATTATA AATGCTGCTA ACAGCAAAGG ACAACCTGGC GGAGGGGTGT
4741 GCGGAGCGCT GTATAAGAAG TTCCCGGAAA GCTTCGATTT ACAGCCGATC GAAGTAGGAA
4801 AAGCGCGACT GGTCAAAGGT GCAGCTAAAC ATATCATTCA TGCCGTAGGA CCAAACTTCA
4861 ACAAAGTTTC GGAGGTTGAA GGTGACAAAC AGTTGGCAGA GGCTTATGAG TCCATCGCTA
4921 AGATTGTCAA CGATAACAAT TACAAGTCAG TAGCGATTCC ACTGTTGTCC ACCGGCATCT
4981 TTTCCGGGAA CAAAGATCGA CTAACCCAAT CATTGAACCA TTTGCTGACA GCTTTAGACA
5041 CCACTGATGC AGATGTAGCC ATATACTGCA GGGACAAGAA ATGGGAAATG ACTCTCAAGG

Figure 7C

```
5101 AAGCAGTGGC TAGGAGAGAA GCAGTGGAGG AGATATGCAT ATCCGACGAC TCTTCAGTGA
5161 CAGAACCTGA TGCAGAGCTG GTGAGGGTGC ATCCGAAGAG TTCTTTGGCT GGAAGGAAGG
5221 GCTACAGCAC AAGCGATGGC AAAACTTTCT CATATTTGGA AGGGACCAAG TTTCACCAGG
5281 CGGCCAAGGA TATAGCAGAA ATTAATGCCA TGTGGCCCGT TGCAACGGAG GCCAATGAGC
5341 AGGTATGCAT GTATATCCTC GGAGAAAGCA TGAGCAGTAT TAGGTCGAAA TGCCCCGTCG
5401 AAGAGTCGGA AGCCTCCACA CCACCTAGCA CGCTGCCTTG CTTGTGCATC CATGCCATGA
5461 CTCCAGAAAG AGTACAGCGC CTAAAAGCCT CACGTCCAGA ACAAATTACT GTGTGCTCAT
5521 CCTTTCCATT GCCGAAGTAT AGAATCACTG GTGTGCAGAA GATCCAATGC TCCCAGCCTA
5581 TATTGTTCTC ACCGAAAGTG CCTGCGTATA TTCATCCAAG GAAGTATCTC GTGGAAACAC
5641 CACCGGTAGA CGAGACTCCG GAGCCATCGG CAGAGAACCA ATCCACAGAG GGGACACCTG
5701 AACAACCACC ACTTATAACC GAGGATGAGA CCAGGACTAG AACGCCTGAG CCGATCATCA
5761 TCGAAGAGGA AGAAGAGGAT AGCATAAGTT TGCTGTCAGA TGGCCCGACC CACCAGGTGC
5821 TGCAAGTCGA GGCAGACATT CACGGGCCGC CCTCTGTATC TAGCTCATCC TGGTCCATTC
5881 CTCATGCATC CGACTTTGAT GTGGACAGTT TATCCATACT TGACACCCTG GAGGGAGCTA
5941 GCGTGACCAG CGGGGCAACG TCAGCCGAGA CTAACTCTTA CTTCGCAAAG AGTATGGAGT
6001 TTCTGGCGCG ACCGGTGCCT GCGCCTCGAA CAGTATTCAG GAACCCTCCA CATCCCGCTC
6061 CGCGCACAAG AACACCGTCA CTTGCACCCA GCAGGGCCTG CTCGAGAACC AGCCTAGTTT
6121 CCACCCCGCC AGGCGTGAAT AGGGTGATCA CTAGAGAGGA GCTCGAGGCG CTTACCCCGT
6181 CACGCACTCC TAGCAGGTCG GTCTCGAGAA CCAGCCTGGT CTCCAACCCG CCAGGCGTAA
6241 ATAGGGTGAT TACAAGAGAG GAGTTTGAGG CGTTCGTAGC ACAACAACAA TGACGGTTTG
6301 ATGCGGGTGC ATACATCTTT TCCTCCGACA CCGGTCAAGG GCATTTACAA CAAAAATCAG
6361 TAAGGCAAAC GGTGCTATCC GAAGTGGTGT TGGAGAGGAC CGAATTGGAG ATTTCGTATG
6421 CCCCGCGCCT CGACCAAGAA AAAGAAGAAT TACTACGCAA GAAATTACAG TTAAATCCCA
6481 CACCTGCTAA CAGAAGCAGA TACCAGTCCA GGAAGGTGGA GAACATGAAA GCCATAACAG
6541 CTAGACGTAT TCTGCAAGGC CTAGGGCATT ATTTGAAGGC AGAAGGAAAA GTGGAGTGCT
6601 ACCGAACCCT GCATCCTGTT CCTTTGTATT CATCTAGTGT GAACCGTGCC TTCTCAAGCC
6661 CCAAGGTCGC AGTGGAAGCC TGTAACGCCA TGTTGAAAGA GAACTTTCCG ACTGTGGCTT
6721 CTTACTGTAT TATTCCAGAG TACGATGCCT ATTTGGACAT GGTTGACGGA GCTTCATGCT
6781 GCTTAGACAC TGCCAGTTTT TGCCCTGCAA AGCTGCGCAG CTTTCCAAAG AAACACTCCT
6841 ATTTGGAACC CACAATACGA TCGGCAGTGC CTTCAGCGAT CCAGAACACG CTCCAGAACG
6901 TCCTGGCAGC TGCCACAAAA AGAAATTGCA ATGTCACGCA AATGAGAGAA TTGCCCGTAT
6961 TGGATTCGGC GGCCTTTAAT GTGGAATGCT TCAAGAAATA TGCGTGTAAT AATGAATATT
7021 GGGAAACGTT TAAAGAAAAC CCCATCAGGC TTACTGAAGA AAACGTGGTA AATTACATTA
7081 CCAAATTAAA AGGACCAAAA GCTGCTGCTC TTTTTGCGAA GACACATAAT TTGAATATGT
7141 TGCAGGACAT ACCAATGGAC AGGTTTGTAA TGGACTTAAA GAGAGACGTG AAAGTGACTC
7201 CAGGAACAAA ACATACTGAA GAACGGCCCA AGGTACAGGT GATCCAGGCT GCCGATCCGC
7261 TAGCAACAGC GTATCTGTGC GGAATCCACC GAGAGCTGGT TAGGAGATTA AATGCGGTCC
7321 TGCTTCCGAA CATTCATACA CTGTTTGATA TGTCGGCTGA AGACTTTGAC GCTATTATAG
7381 CCGAGCACTT CCAGCCTGGG GATTGTGTTC TGGAAACTGA CATCGCGTCG TTTGATAAAA
7441 GTGAGGACGA CGCCATGGCT CTGACCGCGT TAATGATTCT GGAAGACTTA GGTGTGGACG
7501 CAGAGCTGTT GACGCTGATT GAGGCGGCTT TCGGCGAAAT TTCATCAATA CATTTGCCCA
7561 CTAAAACTAA ATTTAAATTC GGAGCCATGA TGAAATCTGG AATGTTCCTC ACACTGTTTG
7621 TGAACACAGT CATTAACATT GTAATCGCAA GCAGAGTGTT GAGAGAACGG CTAACCGGAT
7681 CACCATGTGC AGCATTCATT GGAGATGACA ATATCGTGAA AGGAGTCAAA TCGGACAAAT
7741 TAATGGCAGA CAGGTGCGCC ACCTGGTTGA ATATGGAAGT CAAGATTATA GATGCTGTGG
```

Figure 7D

```
7801 TGGGCGAGAA AGCGCCCTAT TTCTGTGGAG GGTTTATTTT GTGTGACTCC GTGACCGGCA
7861 CAGCGTGCCG TGTGGCAGAC CCCCTAAAAA GGCTGTTTAA GCTTGGCAAA CCTCTGGCAG
7921 CAGACGATGA ACATGATGAT GACAGGAGAA GGGCATTGCA TGAAGAGTCA ACACGCTGGA
7981 ACCGAGTGGG TATTCTTTCA GAGCTGTGCA AGGCAGTAGA ATCAAGGTAT GAAACCGTAG
8041 GAACTTCCAT CATAGTTATG GCCATGACTA CTCTAGCTAG CAGTGTTAAA TCATTCAGCT
8101 ACCTGAGAGG GGCCCCTATA ACTCTCTACG GCTAACCTGA ATGGACTACG ACATAGTCTA
8161 GTCCGCCAAG ATGgagttta tcccaaccca aactttctac aataggaggt accagcctcg
8221 accttggact ccgcgcccta ctatccaagt tatcagaccc agaccgcgtc cgcaaaggaa
8281 agccgggcaa cttgcccagc tgatctcagc agttaataaa ctgacaatgc gcgcggtacc
8341 tcaacagaag ccgcgcaaga atcggaagaa taagaagcaa aagcaaaagc agcaggcgcc
8401 acgaaacaac atgaatcaaa agaagcagcc ccctaaaaag aaaccggctc aaaagaaaaa
8461 gaagccgggc cgtagagaga gaatgtgcat gaaaatcgaa aatgattgca tcttcgaagt
8521 caagcatgaa ggtaaggtaa caggttacgc gtgcttggta ggggacaaag taatgaagcc
8581 agcacacgta aaggggacca tcgataatgc ggacctggcc aaattggcct tcaagcggtc
8641 atctaagtac gaccttgaat gcgcgcagat acccgtgcac atgaagtccg acgcttcgaa
8701 gttcacccat gagaaaccgg aggggtacta caactggcac cacggagcag tacagtactc
8761 aggaggccgg ttcaccatcc ctacaggtgc gggcaaacca ggggacagcg gtagaccgat
8821 cttcgacaac aaggggcgcg tggtggccat agttttagga ggagctaatg aaggagcccg
8881 tacagccctc tcggtggtga cctggaacaa agacatcgtc acgaaaatca cccctgaggg
8941 ggccgaagag tggagtcttg ccattccagt tatgtgcctg ctggcaaata ccacgttccc
9001 ctgctcccag cccccttgca caccctgctg ctacgaaaaa gagccggaga aaaccctgcg
9061 catgctagaa gacaacgtca tgagccccgg gtactatcag ctgctacaag catccttaac
9121 atgttctccc cgccgccagc gacgcagtat taaggacaac ttcaatgtct ataaagccat
9181 aagaccgtac ctagctcact gtcccgactg tggagaaggg cactcgtgcc atagtcccgt
9241 agcgctagaa cgcatcagaa acgaagcgac agacgggacg ctgaaaatcc aggtttcctt
9301 gcaaatcgga ataaagacgg atgatagcca tgattggacc aagctgcgtt acatggacaa
9361 tcatatgcca gcagacgcag agagggccag gctatttgta agaacgtcag caccgtgcac
9421 gattactgga acaatgggac acttcatcct ggcccgatgt ccgaaaggag aaactctgac
9481 ggtgggattc actgacggta ggaagatcag tcactcatgt acgcacccat ttcaccacga
9541 ccctcctgtg ataggccggg aaaaattcca ttcccgaccg cagcacggta gagaactacc
9601 ttgcagcacg tacgcgcaga gcaccgctgc aactgccgag gagatagagg tacatatgcc
9661 cccagacacc ccagatcgca cattgatgtc acaacagtcc ggtaatgtaa agatcacagt
9721 caatagtcag acggtgcggt acaagtgtaa ttgcggtgac tcaaatgaag gactaaccac
9781 tacagacaaa gtgattaata actgcaaggt tgatcaatgc catgccgcgg tcaccaatca
9841 caaaaaatgg cagtataatt cccctctggt cccgcgtaat gctgaactcg ggaccgaaa
9901 aggaaaagtt cacattccgt ttcctctggc aaatgtgaca tgcagggtgc ctaaggcaag
9961 gaaccccacc gtgacgtacg gaaaaaacca agtcatcatg ctgctgtatc ctgaccaccc
10021 aacgctcctg tcctaccgga atatgggaga agaaccaaac tatcaagaag agtgggtgac
10081 gcataagaag gagatcaggt taaccgtgcc gactgaaggg ctcgaggtca cgtggggcaa
10141 caacgagccg tacaagtatt ggccgcagtt atccacaaac ggtacagccc acggccaccc
10201 gcatgagata attttgtatt attatgagct gtaccctact atgactgtgg tagttgtgtc
10261 agtggcctcg ttcgtactcc tgtcgatggt gggtgtggca gtggggatgt gcatgtgtgc
10321 acgacgcaga tgcattacac cgtacgaact gacaccagga gctaccgtcc ctttcctgct
10381 tagcctaata tgctgcatta gaacagctaa agcggccaca taccaagagg ctgcggtata
10441 cctgtggaac gagcagcagc ctttgttttg gctgcaagcc cttattccgc tggcagccct
```

Figure 7E

```
10501 gattgtccta tgcaactgtc tgagactctt accatgcttt tgtaaaacgt tgactttttt
10561 agccgtaatg agcgtcggtg cccacactgt gagcgcgtac gaacacgtaa cagtgatccc
10621 gaacacggtg ggagtaccgt ataagactct agtcaacaga ccgggctaca gccccatggt
10681 actggagatg gagcttctgt cagtcacttt ggagccaacg ctatcgcttg attacatcac
10741 gtgcgagtat aaaaccgtca tcccgtctcc gtacgtgaaa tgctgcggta cagcagagtg
10801 caaggacaag agcctacctg attacagctg taaggtcttc accggcgtct acccattcat
10861 gtggggcggc gcctactgct tctgcgacac tgaaaatacg caattgagcg aagcacatgt
10921 ggagaagtcc gaatcatgca aaacagaatt tgcatcagca tatagggctc ataccgcatc
10981 cgcatcagct aagctccgcg tcctttacca aggaaataat gttactgtat ctgcttatgc
11041 aaacggcgat catgccgtca cagttaagga cgctaaattc attgtggggc caatgtcttc
11101 agcctggaca ccttttgaca ataaaatcgt ggtgtacaaa ggcgacgtct acaacatgga
11161 ctacccgccc ttcggcgcag gaagaccagg acaatttggc gacatccaaa gtcgcacgcc
11221 tgagagcgaa gacgtctatg ctaacacaca actggtactg cagagaccgt ccgcgggtac
11281 ggtgcacgtg ccgtactctc aggcaccatc tggcttcaag tattggctaa aagaacgagg
11341 ggcgtcgctg cagcacacag caccatttgg ctgtcaaata gcaacaaacc cggtaagagc
11401 gatgaactgc gccgtaggga acatgcctat ctccatcgac ataccggacg cggccttcac
11461 tagggtcgtc gacgcgccat ctttaacgga catgtcgtgt gaggtaccag cctgcaccca
11521 ctcctcagac tttgggggcg tagccatcat taaatatgca gccagcaaga aaggcaagtg
11581 tgcggtgcat tcgatgacta acgccgtcac tattcgggaa gctgaaatag aagtagaagg
11641 gaactctcag ttgcaaatct ctttttcgac ggccctagcc agcgccgaat tccgcgtaca
11701 agtctgttct acacaagtac actgtgcagc cgagtgccat ccaccgaaag accatatagt
11761 caattacccg gcgtcacaca ccaccctcgg ggtccaagac atttccgtta cggcgatgtc
11821 atgggtgcag aagatcacgg gaggtgtggg actggttgtc gctgttgcag cactgatcct
11881 aatcgtggtg ctatgcgtgt cgtttagcag gcacTGAATA CAGCAGCAAT TGGCAAGCTG
11941 CTTACATAGA ACTCGCGGCG ATTGGCATGC CGCCTTAAAA TTTTTATTTT ATTTTTTCTT
12001 TTCTTTTCCG AATCGGATTT TGTTTTTAAT ATTTCAAAAA AAAAAAAAAA AAAAAAGGGT
12061 ACGCGGCCGC CACTGTGCTG GATATCTGCA GAATTCCACC ACACTGGACT AGTGGATCAG
12121 CTTAAGTTTA AACCGCTGAT CAGCCTCGAC TGTGCCTTCT AGTTGCCAGC CAT
```

Figures 9A-9E: An i-DNA sequence encoding a chimeric CHIKV derived from live attenuated strain 181/25 that contains C-GPs from TC-83(structural polyproteins from TC-83 highlighted in italics).

Figure 9A

```
   1 GGCGCGCCTG ACATTGATTA TTGACTAGTT ATTAATAGTA ATCAATTACG GGGTCATTAG
  61 TTCATAGCCC ATATATGGAG TTCCGCGTTA CATAACTTAC GGTAAATGGC CCGCCTGGCT
 121 GACCGCCCAA CGACCCCCGC CCATTGACGT CAATAATGAC GTATGTTCCC ATAGTAACGC
 181 CAATAGGGAC TTTCCATTGA CGTCAATGGG TGGAGTATTT ACGGTAAACT GCCCACTTGG
 241 CAGTACATCA AGTGTATCAT ATGCCAAGTA CGCCCCCTAT TGACGTCAAT GACGGTAAAT
 301 GGCCCGCCTG GCATTATGCC CAGTACATGA CCTTATGGGA CTTTCCTACT TGGCAGTACA
 361 TCTACGTATT AGTCATCGCT ATTACCATGG TGATGCGGTT TTGGCAGTAC ATCAATGGGC
 421 GTGGATAGCG GTTTGACTCA CGGGGATTTC CAAGTCTCCA CCCCATTGAC GTCAATGGGA
 481 GTTTGTTTTG GCACCAAAAT CAACGGGACT TTCCAAAATG TCGTAACAAC TCCGCCCCAT
 541 TGACGCAAAT GGGCGGTAGG CGTGTACGGT GGGAGGTCTA TATAAGCAGA GCTCTCTGGC
 601 TAACTAGAGa tggctgcgtg agacacacgt agcctaccag tttcttactg ctctactctg
 661 caaagcaaga gattaataac ccatcatgga ttctgtgtac gtggacatag acgctgacag
 721 cgcctttttg aaggccctgc aacgtgcgta ccccatgttt gaggtggaac ctaggcaggt
 781 cacatcgaat gaccatgcta atgctagagc gttctcgcat ctagccataa aactaataga
 841 gcaggaaatt gatcccgact caaccatcct ggatataggt agtgcgccag caaggaggat
 901 gatgtcggac aggaagtacc actgcgtttg cccgatgcgc agcgcagaag atcccgagag
 961 actcgctaat tatgcgagaa agctcgcatc tgccgcagga aaagtcctgg acagaaacat
1021 ttctggaaag atcggggact tacaagcggt gatggccgtg ccagacacgg agacgccaac
1081 attttgctta cacacagatg tctcatgtag acagagagca gacgtcgcga tataccaaga
1141 cgtctatgct gtacacgcac ccacgtcgct ataccaccag gcgattaaag gagtccgagt
1201 ggcgtactgg gtagggttcg acacaacccc gttcatgtac aacgctatgg cgggtgccta
1261 cccctcatac tcgacaaatt gggcggatga gcaggtactg aaggctaaga acataggatt
1321 atgttcaaca gacctgacgg aaggtagacg aggcaaattg tctatcatga gagggaaaaa
1381 gctaaaaccg tgcgaccgtg tgctgttctc agtagggtca acgctttacc cggaaagccg
1441 cacgctactt aagagctggc acctaccatc ggtgttccat ctaaagggca agcttagctt
1501 cacatgccgc tgtgacacag tggtttcgtg tgagggctac gtcgttaaga gaataacgat
1561 gagcccaggc ctttatggaa aaaccatagg gtatgcggta acccaccacg cagacggatt
1621 cttgatgtgc aagactaccg acacggttga cggcgaaaga gtgtcattct cggtgtgcac
1681 gtacgtgccg gcgaccattt gtgatcaaat gaccggcatc cttgctacag aagtcacgcc
1741 ggaggatgca cagaagctgt tggtggggct gaaccagagg atagtggtta acggcagaac
1801 gcaacggaac acgaacacca tgaagaacta cctacttccc gtggtcgccc aggccttcag
1861 taagtgggca aaggagtgcc ggaaggacat ggaagatgag aagcttctgg gggtcagaga
1921 aagaacacta acctgctgct gtctatgggc atttaagaag cagaaaacac acacggtcta
1981 caagaggcct gatacccagt caatccagaa ggttcaggcc gaatttgaca gctttgtagt
2041 accgggcctg tggtcgtccg ggttgtcaat cccgttgagg actagaatca agtggttgtt
2101 acgcaaggtg ccgaaaacag acctgatccc atacagcggg aatgcccaag aagcccagga
2161 tgcagaaaaa gaagcagagg aagaacgaga agcagaactg actcatgagg ctctaccacc
2221 cctacaggca gcacaggaag atgtccaggt cgaaatcgac gtggaacagc ttgaggatag
2281 agctggtgct ggaataatag agactccgag aggcgctatc aaagttactg cccaactaac
2341 agaccacgtc gtgggggagt acctggtact ttcccgcag accgtactac gcagccagaa
2401 gctcagcctg atccacgctt tagcggagca agtgaagacg tgtacgcaca gcggacgagc
```

Figure 9B 2461 agggaggtat gcggtcgaag cgtacgatgg ccgagtccta gtgccctcag gctatgcaat
2521 ttcgcctgaa gacttccaga gtctaagcga aagcgcaacg atggtgtaca acgaaagaga
2581 gttcgtaaac agaaagttac accacattgc gatgcacgga ccagccctga acactgacga
2641 agagtcgtat gagctggtga gggcagagag gacagaacac gagtacgtct acgacgtgga
2701 ccagagaaga tgctgtaaga aggaagaagc tgcaggactg gtactggtgg gcgacttgac
2761 taatccgccc taccacgaat tcgcatacga agggctaaaa attcgccccg cctgcccata
2821 caaaattgca gtcataggag tcttcggggt accaggatct ggcaagtcag ccattatcaa
2881 gaacctagtt accaggcaag acctggtgac tagcggaaag aaagaaaact gccaagaaat
2941 cagcaccgac gtgatgagac agagaggtct agagatatct gcacgtacgg tagattcgct
3001 gctcttgaat ggatgcaaca gaccagtcga cgtgttgtac gtagacgagg cgtttgcgtg
3061 ccactctgga acgttacttg ctttgatcgc cttggtgaga ccaagacaga aagttgtact
3121 ttgtggtgac ccgaagcagt gcggcttctt caatatgatg cagatgaaag tcaactacaa
3181 tcataacatc tgcacccaag tgtaccacaa aagtatctcc aggcggtgta cactgcctgt
3241 gactgccatt gtgtcatcgt tgcattacga aggcaaaatg cgcactacga atgagtacaa
3301 catgccgatt gtagtggaca ctacaggctc aacgaaacct gaccctggag acctcgtgtt
3361 aacgtgcttc agagggtggg ttaaacaact gcaaattgac tatcgtggac acgaggtcat
3421 gacagcagcc gcatcccaag ggttaactag aaaaggagtt tacgcagtta ggcaaaaagt
3481 taacgaaaac ccactctatg catcaacatc agagcacgtc aacgtactcc taacgcgtac
3541 ggaaggtaaa ctggtatgga agacactctc tggtgacccg tggataaaga cgctgcagaa
3601 cccaccgaaa ggaaacttca aagcaactat taaggagtgg gaggtggagc acgcatcgat
3661 aatggcgggc atctgcagtc accaagtgac ctttgacaca ttccaaaaca aagccaacgt
3721 ttgctgggct aagagcttgg tccctatcct cgaaacagcg ggataaaac taaatgatag
3781 gcagtggtcc cagataattc aagccttcaa agaagacaaa gcatactcac ccgaagtagc
3841 cctgaatgaa atatgcacgc gcatgtatgg ggtggatcta gacagtgggc tattctctaa
3901 accgttggta tctgtgtatt acgcggataa ccattgggat aataggccgg gaggaaagat
3961 gttcggattc aaccctgagg cagcgtccat tctagaaaga aagtacccat ttacaaaagg
4021 aaagtggaac atcaacaagc agatctgcgt gactaccagg aggatagaag acttcaaccc
4081 taccaccaac attataccgg tcaacaggag actaccacac tcattagtgg ccgaacaccg
4141 cccagtaaaa ggggaaagaa tggaatggct ggttaacaag ataaacggac accacgtact
4201 cctggttagc ggctataacc ttgcactgcc tactaagaga gtcacctggg tagcgccact
4261 aggtgtccgc ggagcggact atacatacaa cctagagctg ggtctaccag caacrcttgg
4321 taggtatgac ctagtggtca taaacatcca cacacctttt cgcatacacc attaccaaca
4381 gtgcgtagat cacgcaatga aactgcaaat gctagggggt gactcactga gactgctcaa
4441 accgggtggc tctctattga tcagagcata cggttacgca gatagaacca gtgaacgagt
4501 catctgcgta ctgggacgca agtttagatc gtctagagca ttgaaaccac catgtgtcac
4561 cagtaatact gagatgtttt tcctatttag caattttgac aatggcagaa ggaatttac
4621 aacgcatgtc atgaacaatc aactgaatgc agcctttgta ggacaggcca cccgagcagg
4681 atgtgcacca tcgtaccggg taaaacgcat ggacatcgcg aagaacgatg aagagtgcgt
4741 ggttaacgcc gccaaccctc gcgggttacc aggtgacggt gtttgcaagg cagtatataa
4801 aaagtggccg gagtccttta aaaacagtgc aacaccagta ggaaccgcaa aaacagttat
4861 gtgcggtacg tatccagtaa tccacgccgt aggaccaaac ttctcaaatt attcggagtc
4921 tgaaggggac cgggaattgg cggctgccta tcgagaagtc gcaaaggaag taactagact
4981 gggagtaaat agcgtagcta tacctctcct ctccacaggt gtatactcag gagggaaaga
5041 caggctaacc cagtcactga accacctctt tacagccatg gactcgacgg atgcagacgt
5101 ggtcatctac tgccgagaca aggaatggga gaagaaaata tctgaggcca tacagatgcg

Figure 9C

```
5161 gacccaagtg gagctgctgg atgagcacat ctccatagac tgcgatgtca ttcgcgtgca
5221 ccctgacagt agcttggcag gcagaaaagg atacagcacc acggaaggcg cactgtattc
5281 atatctagaa gggacacgtt ttcaccagac ggcagtggat atggcagaga tatacactat
5341 gtggccaaag caaacagagg ccaatgagca agtctgccta tatgccctgg gggaaagtat
5401 tgaatcaatc aggcagaaat gcccggtgga tgatgcagac gcatcatctc cccgaaaac
5461 tgtcccgtgt ctttgccggt atgccatgac tcctgaacgc gtcacccgac ttcgcatgaa
5521 ccatgtcaca aatataattg tgtgttcttc atttcccctt ccaaagtaca agatagaagg
5581 agtgcaaaaa gtcaaatgct ccaaggtaat gttattcgat cacaatgtgc catcgcgcgt
5641 aagtccaagg gaatacagat cttcccagga gtctgtacag gaagtgagta cgacaacgtc
5701 attgacgcat agccagtttg atctaagcgc cgatggcgag acactgcctg tcccgtcaga
5761 cctggatgct gacgccccag ccctagaacc ggccctagac gacggggcgg tacatacatt
5821 accaaccata atcggaaacc ttgcggccgt gtctgactgg gtaatgagca ccgtacctgt
5881 cgcgccgcct agaagaagga gagggagaaa cctgactgtg acatgtgacg agagagaagg
5941 gaatataaca cccatggcta gcgtccgatt ctttagagca gagctgtgtc cggccgtaca
6001 agaaacagcg gagacgcgtg acacagctat ttcccttcag gcaccgccaa gtaccaccat
6061 ggaactgagc catccaccga tctccttcgg agcaccaagc gagacgttcc ccatcacatt
6121 tggggacttc gacgaaggag aaatcgaaag cttgtcttct gagctactaa ctttcggaga
6181 cttcctaccc ggtgaagtgg atgatctgac agatagcgac tggtccacgt gcccagacac
6241 ggacgacgag ttatgactag acagggcagg tgggtatata ttctcgtcgg acactggtcc
6301 aggccattta caacagaagt cggtacgcca gtcagtgctg ccggtaaaca ccctggagga
6361 agtccacgag gagaagtgtt acccacctaa gctggatgaa ttaaaggagc aactactact
6421 taagaaactc caggagagtg cgtccatggc caatagaagc aggtatcagt cacgcaaagt
6481 ggaaaatatg aaagcaacaa tcatccagag actaaagaga ggctgtaaac tgtatttaat
6541 ggcagagacc ccgaaagtcc cgacttatcg gaccatatac ccggcgcctg tgtactcgcc
6601 tccgatcaat gtccgattgt ccaaccccga gtccgcagtg gcagcatgta atgagttctt
6661 agctagaaac tacccaactg tttcatcata ccaaatcacc gacgagtatg atgcatatct
6721 agacatggtg gacgggtcgg agagttgctt ggaccgagcg acattcaatc cgtcaaaact
6781 taggagctac ccgaaacaac atgcttatca cgcgccttct atcagaagcg ctgtaccttc
6841 cccattccag aacacactac agaatgtact ggcagcagcc acgaaaagga actgcaacgt
6901 cacacagatg agggaattac ccactttgga ctcagcagta ttcaacgtgg agtgttttaa
6961 aaaattcgca tgtaaccgag aatactggga agaatttgca gccagcccta tcaggataac
7021 aactgagaat ctaacaacct atgtcactaa actaaagggg ccaaaagcag cagcgctgtt
7081 tgcaaaaacc cataatctgc tgccactgca ggatgtacca atggataggt tcacagtaga
7141 tatgaaaagg gatgtgaagg taactcctgg tacaaagcat acagaggaaa gacctaaggt
7201 gcaggttata caggcggctg aacccttggc aacagcgtac ctatgtggaa ttcacagaga
7261 actggttagg agattgaacg ccgtcctcct acccaatgtg catacactat ttgacatgtc
7321 tgccgaggac ttcgatgcca ttatagccgc acacttcaag ccaggagacg ctgttttaga
7381 aacggacata gcctcctttg ataagagcca agatgattca cttgcgctta ccgccttaat
7441 gctgttagaa gatttgggag tggatcactc cctgttggac ttgatagagg ctgctttcgg
7501 agagatttcc agctgtcatc tgccgacagg tacgcgcttc aagttcggcg ctatgatgaa
7561 atccggtatg ttcctaactc tgttcgtcaa cacgttgtta aatatcacca tcgctagccg
7621 ggtgttggaa gatcgtctga caaaatccgc atgcgcggcc ttcatcggcg acgacaacat
7681 aatacatggt gtcgtctccg atgaattgat ggcagccaga tgcgctactt ggatgaacat
7741 ggaagtgaag atcatagatg cagttgtatc ccagaaagct ccttactttt gtggagggtt
7801 tatactgcat gatactgtga caggaacagc ttgcagagtg gcggacccgc taaaaaggtt
```

Figure 9D

```
7861 atttaaattg ggcaaaccgt tagcggcagg tgacgaacaa gatgaagaca gaagacgggc
7921 gctggctgat gaagtaatca gatggcaacg aacagggcta atagatgagc tggagaaagc
7981 ggtgtactct aggtacgaag tgcagggtat atcagttgcg gtaatgtcca tggccacctt
8041 tgcaagctcc agatccaact tcgagaagct cagaggaccc gtcataactt tgtacggcgg
8101 tcctaaatag gtacgcacta cagctaccta ttttgcagaa gccgacagca ggtacctaaa
8161 taccaatcag ccataatgtt cccgttccag ccaatgtatc cgatgcagcc aatgccctat
8221 cgcaacccgt tcgcggcccc gcgcaggccc tggttcccca gaaccgaccc ttttctggcg
8281 atgcaggtgc aggaattaac ccgctcgatg gctaacctga cgttcaagca acgccgggac
8341 gcgccacctg aggggccatc cgctaagaaa ccgaagaagg aggcctcgca aaaacagaaa
8401 gggggaggcc aagggaagaa gaagaagaac caagggaaga agaaggctaa gacagggccg
8461 cctaatccga aggcacagaa tggaaacaag aagaagacca acaagaaacc aggcaagaga
8521 cagcgcatgg tcatgaaatt ggaatctgac aagacgttcc caatcatgtt ggaagggaag
8581 ataaacggct acgcttgtgt ggtcggaggg aagttattca ggccgatgca tgtggaaggc
8641 aagatcgaca acgacgttct ggccgcgctt aagacgaaga aagcatccaa atacgatctt
8701 gagtatgcag atgtgccaca gaacatgcgg gccgatacat tcaaatacac ccatgagaaa
8761 ccccaaggct attacagctg gcatcatgga gcagtccaat atgaaaatgg gcgtttcacg
8821 gtgccgaaag gagttggggc caagggagac agcggacgac ccattctgga taaccaggga
8881 cgggtggtcg ctattgtgct gggaggtgtg aatgaaggat ctaggacagc cctttcagtc
8941 gtcatgtgga acgagaaggg agttaccgtg aagtatactc cggagaactg cgagcaatgg
9001 tcactagtga ccaccatgtg tctgctcgcc aatgtgacgt tcccatgtgc tcaaccacca
9061 atttgctacg acagaaaacc agcagagact ttggccatgc tcagcgttaa cgttgacaac
9121 ccgggctacg atgagctgct ggaagcagct gttaagtgcc ccggaaggaa aaggagatcc
9181 accgaggagc tgtttaatga gtataagcta acgcgccctt acatggccag atgcatcaga
9241 tgtgcagttg ggagctgcca tagtccaata gcaatcgagg cagtaaagag cgacgggcac
9301 gacggttatg ttagacttca gacttcctcg cagtatggcc tggattcctc cggcaactta
9361 aagggcagga ccatgcggta tgacatgcac gggaccatta aagagatacc actacatcaa
9421 gtgtcactct atacatctcg cccgtgtcac attgtggatg ggcacggtta tttcctgctt
9481 gccaggtgcc cggcagggga ctccatcacc atggaattta agaaagattc cgtcagacac
9541 tcctgctcgg tgccgtatga agtgaaattt aatcctgtag gcagagaact ctatactcat
9601 cccccagaac acggagtaga gcaagcgtgc caagtctacg cacatgatgc acagaacaga
9661 ggagcttatg tcgagatgca cctcccgggc tcagaagtgg acagcagttt ggtttccttg
9721 agcggcagtt cagtcaccgt gacacctcct gatgggacta gcgccctggt ggaatgcgag
9781 tgtggcggca caaagatctc cgagaccatc aacaagacaa aacagttcag ccagtgcaca
9841 aagaaggagc agtgcagagc atatcggctg cagaacgata agtgggtgta taattctgac
9901 aaactgccca aagcagcggg agccacctta aaaggaaaac tgcatgtccc attcttgctg
9961 gcagacggca aatgcaccgt gcctctagca ccagaaccta tgataacctt cggtttcaga
10021 tcagtgtcac tgaaactgca ccctaagaat cccacatatc taatcacccg ccaacttgct
10081 gatgagcctc actacacgca cgagctcata tctgaaccag ctgttaggaa ttttaccgtc
10141 accgaaaaag ggtgggagtt tgtatgggga aaccacccgc cgaaaaggtt ttgggcacag
10201 gaaacagcac ccggaaatcc acatgggcta ccgcacgagg tgataactca ttattaccac
10261 agatacccta tgtccaccat cctgggtttg tcaatttgtg ccgccattgc aaccgtttcc
10321 gttgcagcgt ctacctggct gttttgcaga tctagagttg cgtgcctaac tccttaccgg
10381 ctaacaccta acgctaggat accatttgt ctggctgtgc tttgctgcgc ccgcactgcc
10441 cgggccgaga ccacctggga gtccttggat cacctatgga acaataacca acagatgttc
10501 tggattcaat tgctgatccc tctggccgcc ttgatcgtag tgactcgcct gctcaggtgc
```

Figure 9E

*10561 gtgtgctgtg tcgtgccttt tttagtcatg gccggcgccg caggcgccgg cgcctacgag*
*10621 cacgcgacca cgatgccgag ccaagcggga atctcgtata acactatagt caacagagca*
*10681 ggctacgcac cactccctat cagcataaca ccaacaaaga tcaagctgat acctacagtg*
*10741 aacttggagt acgtcacctg ccactacaaa acaggaatgg attcaccagc catcaaatgc*
*10801 tgcggatctc aggaatgcac tccaacttac aggcctgatg aacagtgcaa agtcttcaca*
*10861 ggggtttacc cgttcatgtg ggtggtgca tattgctttt gcgacactga gaacacccaa*
*10921 gtcagcaagg cctacgtaat gaaatctgac gactgccttg cggatcatgc tgaagcatat*
*10981 aaagcgcaca cagcctcagt gcaggcgttc ctcaacatca cagtgggaga acactctatt*
*11041 gtgactaccg tgtatgtgaa tggagaaact cctgtgaatt tcaatggggt caaaataact*
*11101 gcaggtccgc tttccacagc ttggacaccc tttgatcgca aaatcgtgca gtatgccggg*
*11161 gagatctata attatgattt tcctgagtat ggggcaggac aaccaggagc atttggagat*
*11221 atacaatcca gaacagtctc aagctctgat ctgtatgcca ataccaacct agtgctgcag*
*11281 agacccaaag caggagcgat ccacgtgcca tacactcagg caccttcggg ttttgagcaa*
*11341 tggaagaaag ataaagctcc atcattgaaa tttaccgccc ctttcggatg cgaaatatat*
*11401 acaaacccca ttcgcgccga aaactgtgct gtagggtcaa ttccattagc ctttgacatt*
*11461 cccgacgcct tgttcaccag ggtgtcagaa acaccgacac tttcagcggc cgaatgcact*
*11521 cttaacgagt gcgtgtattc ttccgacttt ggtgggatcg ccacggtcaa gtactcggcc*
*11581 agcaagtcag gcaagtgcgc agtccatgtg ccatcaggga ctgctaccct aaaagaagca*
*11641 gcagtcgagc taaccgagca agggtcggcg actatccatt tctcgaccgc aaatatccac*
*11701 ccggagttca ggctccaaat atgcacatca tatgttacgt gcaaaggtga ttgtcacccc*
*11761 ccgaaagacc atattgtgac acaccctcag tatcacgccc aaacatttac agccgcggtg*
*11821 tcaaaaaccg cgtggacgtg gttaacatcc ctgctgggag gatcagccgt aattattata*
*11881 attggcttgg tgctggctac tattgtggcc atgtacgtgc tgaccaacca gaaacataat*
*11941 tga*cttgaca actaggtacg aaggtatatg tgtcccctaa gagacacacc acatatagct
12001 aagaatcaat agataagtat agatcaaagg gctgaacaac ccctgaatag taacaaaata
12061 taaaaatcaa caaaaatcat aaaatagaaa accagaaaca gaagtaggta agaaggtata
12121 tgtgtcccct aagagacaca ccatatatag ctaagaatca atagataagt atagatcaaa
12181 gggctgaata accccctgaat aataacaaaa tataaaaatc aataaaaatc ataaaataga
12241 aaaccataaa cagaagtagt tcaaagggct ataaaacccc tgaatagtaa caaaacataa
12301 aactaataaa aatcaaatga ataccataat tggcaatcgg aagagatgta ggtacttaag
12361 cttcctaaaa gcagccgaac tcgctttgag atgtaggcgt agcacaccga actcttccat
12421 aattctccga acccacaggg acgtaggaga tgttcaaagt ggctataaaa ccctgaacag
12481 taataaaaca taaaattaat aaggatcaaa tgagtaccat aattggcaaa cggaagagat
12541 gtaggtactt aagcttccta aaagcagccg aactcacttt gagatgtagg catagcatac
12601 cgaactcttc cacaattctc cgtacccata gggacgtagg agatgttatt ttgtttttaa
12661 tatttcAAAA AAAAAAAAAA AAAAAAAGGG TACGCGGCCG CCACTGTGCT GGATATCTGC
12721 AGAATTCCAC CACACTGGAC TAGTGGATCA GCTTAAGTTT AAACCGCTGA TCAGCCTCGA
12781 CTGTGCCTTC TAGTTGCCAG CCATCTGTTG TTTGCCCCTC CCCCGTGCCT TCCTTGACCC
12841 TGGAAGGTGC CACTCCCACT GTCCTTTCCT AATAAAATGA GGAAATTGCA TCGCATTGTC
12901 TGAGTAGGTG TCATTCTATT CTGGGGGGTG GGGTGGGGCA GGAC CHIKV i-DNA™

Negaitve Control

CHIKV i-DNA™ linearized
using NotI (high magnification)

Virus Derived from CHIKV i-DNA™

IND Vaccine 181/25

Figure 12

IND Vaccine 181/25*: Sequence Heterogeneity
with Reversions to Virulent Virus

```
Clone
              301          314
3.5_23        TGYAVTHHADGFLMCKTTDTVDGERVSFSVCTYVPATICDQMTGILATEVTPEDAQKLLV 126
3.5_53        TGYAVTHHADGFLMCKTTDTVDGERVSFSVCTYVPATICDQMTGILATEVTPEDAQKLLV 127
GB_3412-78    TGYAVTHHADGFLMCKTTDTVDGERVSFSVCTYVPATICDQMTGILATEVTPEDAQKLLV 360
3.5_33        TGYAVTHHADGFLLCKTTDTVDGERVSFSVCTYVPATICDQMTGILATEVTPEDAQKLLV 125
3.5_54        TGYAVTHHADGFLLCKTTDTVDGERVSFSVCTYVPATICDQMTGILATEVTPEDAQKLLV 126
3.5_10        TGYAVTHHADGFLLCKTTDTVDGERVSFSVCTYVPATICDQMTGILATEVTPEDAQKLLV 319
GB VR1 **     TGYAVTHHADGFLLCKTTDTVDGERVSFSVCTYVPATICDQMTGILATEVTPEDAQKLLV 360
4.1_23        TGYAVTHHADGFLLCKTTDTVDGERVSFSVCTYVPATICDQMTGILATEVTPEDAQKLLV 360
GB TH35       TGYAVTHHADGFLMSKTTDTVDGERVSFSVCTYVPATICDQMTGILATEVTPEDAQKLLV 360
GB AF15561    TGYAVTHHADGFLMCKTTDTVDGERVSFSVCTYVPATICDQMTGILATEVTPEDAQKLLV 360
GB_181/25     IGYAVTHHADGFLMCKTTDTVDGERVSFSVCTYVPATICDQMTGILATEVTPEDAQKLLV 360
3.5_40        IGYAVTHHADGFLMCKTTDTVDGERVSFSVCTYVPATICDQMTGILATEVTPEDAQKLLV 319
              *************:.**********************************************
```

* Edelman et al. PHASE II SAFETY AND IMMUNOGENICITY STUDY OF LIVE CHIKUNGUNYA VIRUS VACCINE TSI-GSD-218. Am. J. Trop. Med. Hyg., 62(6), 2000, pp. 681–685

** Virulent isolate from viremic patent vaccinated with 181/25, EF452494

SEQUENCE LISTING

```
<160> NUMBER OF SEQ ID NOS: 18

<210> SEQ ID NO 1
<211> LENGTH: 13251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

ggcgcgcctg acattgatta ttgactagtt attaatagta atcaattacg gggtcattag      60

ttcatagccc atatatggag ttccgcgtta cataacttac ggtaaatggc ccgcctggct     120

gaccgcccaa cgacccccgc ccattgacgt caataatgac gtatgttccc atagtaacgc     180

caatagggac tttccattga cgtcaatggg tggagtattt acggtaaact gcccacttgg     240

cagtacatca agtgtatcat atgccaagta cgccccctat tgacgtcaat gacggtaaat     300

ggcccgcctg gcattatgcc cagtacatga ccttatggga ctttcctact tggcagtaca     360

tctacgtatt agtcatcgct attaccatgg tgatgcggtt ttggcagtac atcaatgggc     420

gtggatagcg gtttgactca cggggatttc caagtctcca ccccattgac gtcaatggga     480

gtttgttttg gcaccaaaat caacgggact ttccaaaatg tcgtaacaac tccgccccat     540

tgacgcaaat gggcggtagg cgtgtacggt gggaggtcta tataagcaga gctctctggc     600

taactagaga tggctgcgtg agacacacgt agcctaccag tttcttactg ctctactctg     660
```

-continued

```
caaagcaaga gattaataac ccatcatgga ttctgtgtac gtggacatag acgctgacag    720
cgccttttg aaggccctgc aacgtgcgta ccccatgttt gaggtggaac ctaggcaggt    780
cacatcgaat gaccatgcta atgctagagc gttctcgcat ctagccataa aactaataga    840
gcaggaaatt gatcccgact caaccatcct ggatataggt agtgcgccag caaggaggat    900
gatgtcggac aggaagtacc actgcgtttg cccgatgcgc agcgcagaag atcccgagag    960
actcgctaat tatgcgagaa agctcgcatc tgccgcagga aaagtcctgg acagaaacat   1020
ttctggaaag atcggggact tacaagcggt gatggccgtg ccagacacgg agacgccaac   1080
attttgctta cacacagatg tctcatgtag acagagagca gacgtcgcga tataccaaga   1140
cgtctatgct gtacacgcac ccacgtcgct ataccaccag gcgattaaag gagtccgagt   1200
ggcgtactgg gtagggttcg acacaacccc gttcatgtac aacgctatgg cgggtgccta   1260
cccctcatac tcgacaaatt gggcggatga gcaggtactg aaggctaaga acataggatt   1320
atgttcaaca gacctgacgg aaggtagacg aggcaaattg tctatcatga gagggaaaaa   1380
gctaaaaccg tgcgaccgtg tgctgttctc agtagggtca acgctttacc cggaaagccg   1440
cacgctactt aagagctggc acctaccatc ggtgttccat ctaaagggca agcttagctt   1500
cacatgccgc tgtgacacag tggtttcgtg tgagggctac gtcgttaaga gaataacgat   1560
gagcccaggc ctttatggaa aaaccatagg gtatgcggta acccaccacg cagacggatt   1620
cttgatgtgc aagactaccg acacggttga cggcgaaaga gtgtcattct cggtgtgcac   1680
gtacgtgccg gcgaccattt gtgatcaaat gaccggcatc cttgctacag aagtcacgcc   1740
ggaggatgca cagaagctgt tggtggggct gaaccagagg atagtggtta acggcagaac   1800
gcaacggaac acgaacacca tgaagaacta cctacttccc gtggtcgccc aggccttcag   1860
taagtgggca aaggagtgcc ggaaggacat ggaagatgag aagcttctgg gggtcagaga   1920
aagaacacta acctgctgct gtctatgggc atttaagaag cagaaaacac acacggtcta   1980
caagaggcct gatacccagt caatccagaa ggttcaggcc gaatttgaca gctttgtagt   2040
accgggcctg tggtcgtccg ggttgtcaat cccgttgagg actagaatca agtggttgtt   2100
acgcaaggtg ccgaaaacag acctgatccc atacagcggg aatgcccaag aagcccagga   2160
tgcagaaaaa gaagcagagg aagaacgaga agcagaactg actcatgagg ctctaccacc   2220
cctacaggca gcacaggaag atgtccaggt cgaaatcgac gtggaacagc ttgaggatag   2280
agctggtgct ggaataatag agactccgag aggcgctatc aaagttactg cccaactaac   2340
agaccacgtc gtgggggagt acctggtact ttccccgcag accgtactac gcagccagaa   2400
gctcagcctg atccacgctt tagcggagca agtgaagacg tgtacgcaca gcggacgagc   2460
agggaggtat gcggtcgaag cgtacgatgg ccgagtccta gtgccctcag gctatgcaat   2520
ttcgcctgaa gacttccaga gtctaagcga aagcgcaacg atggtgtaca acgaaagaga   2580
gttcgtaaac agaaagttac accacattgc gatgcacgga ccagccctga acactgacga   2640
agagtcgtat gagctggtga gggcagagag gacagaacac gagtacgtct acgacgtgga   2700
ccagagaaga tgctgtaaga aggaagaagc tgcaggactg gtactggtgg gcgacttgac   2760
taatccgccc taccacgaat tcgcatacga agggctaaaa attcgccccg cctgcccata   2820
caaaattgca gtcataggag tcttcggggt accaggatct ggcaagtcag ccattatcaa   2880
gaacctagtt accaggcaag acctggtgac tagcggaaag aaagaaaact gccaagaaat   2940
cagcaccgac gtgatgagac agagaggtct agagatatct gcacgtacgg tagattcgct   3000
gctcttgaat ggatgcaaca gaccagtcga cgtgttgtac gtagacgagg cgtttgcgtg   3060
```

-continued

```
ccactctgga acgttacttg ctttgatcgc cttggtgaga ccaagacaga aagttgtact   3120
ttgtggtgac ccgaagcagt gcggcttctt caatatgatg cagatgaaag tcaactacaa   3180
tcataacatc tgcacccaag tgtaccacaa aagtatctcc aggcggtgta cactgcctgt   3240
gactgccatt gtgtcatcgt tgcattacga aggcaaaatg cgcactacga atgagtacaa   3300
catgccgatt gtagtggaca ctacaggctc aacgaaacct gaccctggag acctcgtgtt   3360
aacgtgcttc agagggtggg ttaaacaact gcaaattgac tatcgtggac acgaggtcat   3420
gacagcagcc gcatcccaag ggttaactag aaaaggagtt tacgcagtta ggcaaaaagt   3480
taacgaaaac ccactctatg catcaacatc agagcacgtc aacgtactcc taacgcgtac   3540
ggaaggtaaa ctggtatgga agacactctc tggtgacccg tggataaaga cgctgcagaa   3600
cccaccgaaa ggaaacttca aagcaactat taaggagtgg gaggtggagc acgcatcgat   3660
aatggcgggc atctgcagtc accaagtgac ctttgacaca ttccaaaaca aagccaacgt   3720
ttgctgggct aagagcttgg tccctatcct cgaaacagcg ggataaaac taaatgatag   3780
gcagtggtcc cagataattc aagccttcaa agaagacaaa gcatactcac ccgaagtagc   3840
cctgaatgaa atatgcacgc gcatgtatgg ggtggatcta gacagtgggc tattctctaa   3900
accgttggta tctgtgtatt acgcggataa ccattgggat aataggccgg gaggaaagat   3960
gttcggattc aaccctgagg cagcgtccat tctagaaaga aagtacccat ttacaaaagg   4020
aaagtggaac atcaacaagc agatctgcgt gactaccagg aggatagaag acttcaaccc   4080
taccaccaac attataccgg tcaacaggag actaccacac tcattagtgg ccgaacaccg   4140
cccagtaaaa ggggaaagaa tggaatggct ggttaacaag ataaacggac accacgtact   4200
cctggttagc ggctataacc ttgcactgcc tactaagaga gtcacctggg tagcgccact   4260
aggtgtccgc ggagcggact atacatacaa cctagagctg ggtctaccag caacrcttgg   4320
taggtatgac ctagtggtca taaacatcca cacacctttt cgcatacacc attaccaaca   4380
gtgcgtagat cacgcaatga aactgcaaat gctagggggt gactcactga gactgctcaa   4440
accgggtggc tctctattga tcagagcata cggttacgca gatagaacca gtgaacgagt   4500
catctgcgta ctgggacgca agtttagatc gtctagagca ttgaaaccac catgtgtcac   4560
cagtaatact gagatgtttt tcctatttag caattttgac aatggcagaa ggaattttac   4620
aacgcatgtc atgaacaatc aactgaatgc agcctttgta ggacaggcca cccgagcagg   4680
atgtgcacca tcgtaccggg taaaacgcat ggacatcgcg aagaacgatg aagagtgcgt   4740
ggttaacgcc gccaaccctc gcgggttacc aggtgacggt gtttgcaagg cagtatataa   4800
aaagtggccg gagtccttta aaaacagtgc aacaccagta ggaaccgcaa aaacagttat   4860
gtgcggtacg tatccagtaa tccacgccgt aggaccaaac ttctcaaatt attcggagtc   4920
tgaaggggac cgggaattgg cggctgccta tcgagaagtc gcaaaggaag taactagact   4980
gggagtaaat agcgtagcta tacctctcct ctccacaggt gtatactcag gagggaaaga   5040
caggctaacc cagtcactga accacctctt tacagccatg gactcgacgg atgcagacgt   5100
ggtcatctac tgccgagaca aggaatggga gaagaaaata tctgaggcca tacagatgcg   5160
gacccaagtg gagctgctgg atgagcacat ctccatagac tgcgatgtca ttcgcgtgca   5220
ccctgacagt agcttggcag gcagaaaagg atacagcacc acggaaggcg cactgtattc   5280
atatctagaa gggacacgtt ttcaccagac ggcagtggat atggcagaga tatacactat   5340
gtggccaaag caaacagagg ccaatgagca agtctgccta tatgccctgg gggaaagtat   5400
```

-continued

```
tgaatcaatc aggcagaaat gcccggtgga tgatgcagac gcatcatctc ccccgaaaac   5460
tgtcccgtgt ctttgccggt atgccatgac tcctgaacgc gtcacccgac ttcgcatgaa   5520
ccatgtcaca aatataattg tgtgttcttc atttcccctt ccaaagtaca agatagaagg   5580
agtgcaaaaa gtcaaatgct ccaaggtaat gttattcgat cacaatgtgc catcgcgcgt   5640
aagtccaagg gaatacagat cttcccagga gtctgtacag gaagtgagta cgacaacgtc   5700
attgacgcat agccagtttg atctaagcgc cgatggcgag acactgcctg tcccgtcaga   5760
cctggatgct gacgccccag ccctagaacc ggccctagac gacggggcgg tacatacatt   5820
accaaccata atcggaaacc ttgcggccgt gtctgactgg gtaatgagca ccgtacctgt   5880
cgcgccgcct agaagaagga gagggagaaa cctgactgtg acatgtgacg agagagaagg   5940
gaatataaca cccatggcta gcgtccgatt ctttagagca gagctgtgtc cggccgtaca   6000
agaaacagcg gagacgcgtg acacagctat ttcccttcag gcaccgccaa gtaccaccat   6060
ggaactgagc catccaccga tctccttcgg agcaccaagc gagacgttcc ccatcacatt   6120
tggggacttc gacgaaggag aaatcgaaag cttgtcttct gagctactaa ctttcggaga   6180
cttcctaccc ggtgaagtgg atgatctgac agatagcgac tggtccacgt gcccagacac   6240
ggacgacgag ttatgactag acagggcagg tgggtatata ttctcgtcgg acactggtcc   6300
aggccattta caacagaagt cggtacgcca gtcagtgctg ccggtaaaca ccctggagga   6360
agtccacgag gagaagtgtt acccacctaa gctggatgaa ttaaaggagc aactactact   6420
taagaaactc caggagagtg cgtccatggc caatagaagc aggtatcagt cacgcaaagt   6480
ggaaaatatg aaagcaacaa tcatccagag actaaagaga ggctgtaaac tgtatttaat   6540
ggcagagacc ccgaaagtcc cgacttatcg gaccatatac ccggcgcctg tgtactcgcc   6600
tccgatcaat gtccgattgt ccaaccccga gtccgcagtg gcagcatgta atgagttctt   6660
agctagaaac tacccaactg tttcatcata ccaaatcacc gacgagtatg atgcatatct   6720
agacatggtg gacgggtcgg agagttgctt ggaccgagcg acattcaatc cgtcaaaact   6780
taggagctac ccgaaacaac atgcttatca cgcgccttct atcagaagcg ctgtaccttc   6840
cccattccag aacacactac agaatgtact ggcagcagcc acgaaaagga actgcaacgt   6900
cacacagatg agggaattac ccactttgga ctcagcagta ttcaacgtgg agtgttttaa   6960
aaaattcgca tgtaaccgag aatactggga agaatttgca gccagcccta tcaggataac   7020
aactgagaat ctaacaacct atgtcactaa actaaagggg ccaaaagcag cagcgctgtt   7080
tgcaaaaacc cataatctgc tgccactgca ggatgtacca atggataggt tcacagtaga   7140
tatgaaaagg gatgtgaagg taactcctgg tacaaagcat acagaggaaa gacctaaggt   7200
gcaggttata caggcggctg aacccttggc aacagcgtac ctatgtggaa ttcacagaga   7260
actggttagg agattgaacg ccgtcctcct acccaatgtg catacactat ttgacatgtc   7320
tgccgaggac ttcgatgcca ttatagccgc acacttcaag ccaggagacg ctgttttaga   7380
aacggacata gcctcctttg ataagagcca agatgattca cttgcgctta ccgccttaat   7440
gctgttagaa gatttgggag tggatcactc cctgttggac ttgatagagg ctgctttcgg   7500
agagatttcc agctgtcatc tgccgacagg tacgcgcttc aagttcggcg ctatgatgaa   7560
atccggtatg ttcctaactc tgttcgtcaa cacgttgtta aatatcacca tcgctagccg   7620
ggtgttggaa gatcgtctga caaaatccgc atgcgcggcc ttcatcggcg acgacaacat   7680
aatacatggt gtcgtctccg atgaattgat ggcagccaga tgcgctactt ggatgaacat   7740
ggaagtgaag atcatagatg cagttgtatc ccagaaagct ccttactttt gtggagggtt   7800
```

-continued

```
tatactgcat gatactgtga caggaacagc ttgcagagtg gcggacccgc taaaaaggtt   7860
atttaaattg ggcaaaccgt tagcggcagg tgacgaacaa gatgaagaca gaagacgggc   7920
gctggctgat gaagtaatca gatggcaacg aacagggcta atagatgagc tggagaaagc   7980
ggtgtactct aggtacgaag tgcagggtat atcagttgcg gtaatgtcca tggccacctt   8040
tgcaagctcc agatccaact tcgagaagct cagaggaccc gtcataactt tgtacggcgg   8100
tcctaaatag gtacgcacta cagctaccta ttttgcagaa gccgacagca ggtacctaaa   8160
taccaatcag ccataatgga gtttatccca acccaaactt tctacaatag gaggtaccag   8220
cctcgacctt ggactccgcg ccctactatc caagttatca gacccagacc gcgtccgcaa   8280
aggaaagccg ggcaacttgc ccagctgatc tcagcagtta ataaactgac aatgcgcgcg   8340
gtacctcaac agaagccgcg caagaatcgg aagaataaga agcaaaagca aaagcagcag   8400
gcgccacgaa acaacatgaa tcaaaagaag cagcccccta aaaagaaacc ggctcaaaag   8460
aaaaagaagc cgggccgtag agagagaatg tgcatgaaaa tcgaaaatga ttgcatcttc   8520
gaagtcaagc atgaaggtaa ggtaacaggt tacgcgtgct tggtagggga caaagtaatg   8580
aagccagcac acgtaaaggg gaccatcgat aatgcggacc tggccaaatt ggccttcaag   8640
cggtcatcta agtacgacct tgaatgcgcg cagatacccg tgcacatgaa gtccgacgct   8700
tcgaagttca cccatgagaa accggagggg tactacaact ggcaccacgg agcagtacag   8760
tactcaggag gccggttcac catccctaca ggtgcgggca aaccagggga cagcggtaga   8820
ccgatcttcg acaacaaggg gcgcgtggtg gccatagttt taggaggagc taatgaagga   8880
gcccgtacag ccctctcggt ggtgacctgg aacaaagaca tcgtcacgaa aatcacccct   8940
gagggggccg aagagtggag tcttgccatt ccagttatgt gcctgctggc aaataccacg   9000
ttcccctgct cccagccccc ttgcacaccc tgctgctacg aaaaagagcc ggagaaaacc   9060
ctgcgcatgc tagaagacaa cgtcatgagc cccgggtact atcagctgct acaagcatcc   9120
ttaacatgtt ctccccgccg ccagcgacgc agtattaagg acaacttcaa tgtctataaa   9180
gccataagac cgtacctagc tcactgtccc gactgtggag aagggcactc gtgccatagt   9240
cccgtagcgc tagaacgcat cagaaacgaa gcgacagacg ggacgctgaa aatccaggtt   9300
tccttgcaaa tcggaataaa gacggatgat agccatgatt ggaccaagct gcgttacatg   9360
gacaatcata tgccagcaga cgcagagagg gccaggctat ttgtaagaac gtcagcaccg   9420
tgcacgatta ctggaacaat gggacacttc atcctggccc gatgtccgaa aggagaaact   9480
ctgacggtgg gattcactga cggtaggaag atcagtcact catgtacgca cccatttcac   9540
cacgaccctc ctgtgatagg ccgggaaaaa tttcattccc gaccgcagca cggtagagaa   9600
ctaccttgca gcacgtacgc gcagagcacc gctgcaactg ccgaggagat agaggtacat   9660
atgcccccag acaccccaga tcgcacattg atgtcacaac agtccggtaa tgtaaagatc   9720
acagtcaata gtcagacggt gcggtacaag tgtaattgcg gtgactcaaa tgaaggacta   9780
accactacag acaaagtgat taataactgc aaggttgatc aatgccatgc cgcggtcacc   9840
aatcacaaaa aatggcagta taattcccct ctggtcccgc gtaatgctga actcggggac   9900
cgaaaaggaa aagttcacat tccgtttcct ctggcaaatg tgacatgcag ggtgcctaag   9960
gcaaggaacc ccaccgtgac gtacggaaaa aaccaagtca tcatgctgct gtatcctgac  10020
cacccaacgc tcctgtccta ccggaatatg ggagaagaac caaactatca agaagagtgg  10080
gtgacgcata agaaggagat caggttaacc gtgccgactg aagggctcga ggtcacgtgg  10140
```

-continued

```
ggcaacaacg agccgtacaa gtattggccg cagttatcca caaacggtac agcccacggc  10200
cacccgcatg agataatttt gtattattat gagctgtacc ctactatgac tgtggtagtt  10260
gtgtcagtgg cctcgttcgt actcctgtcg atggtgggtg tggcagtggg gatgtgcatg  10320
tgtgcacgac gcagatgcat tacaccgtac gaactgacac caggagctac cgtccctttc  10380
ctgcttagcc taatatgctg cattagaaca gctaaagcgg ccacatacca agaggctgcg  10440
gtatacctgt ggaacgagca gcagcctttg ttttggctgc aagcccttat tccgctggca  10500
gccctgattg tcctatgcaa ctgtctgaga ctcttaccat gcttttgtaa aacgttgact  10560
tttttagccg taatgagcgt cggtgcccac actgtgagcg cgtacgaaca cgtaacagtg  10620
atcccgaaca cggtgggagt accgtataag actctagtca acagaccggg ctacagcccc  10680
atggtactgg agatggagct tctgtcagtc actttggagc caacgctatc gcttgattac  10740
atcacgtgcg agtataaaac cgtcatcccg tctccgtacg tgaaatgctg cggtacagca  10800
gagtgcaagg acaagagcct acctgattac agctgtaagg tcttcaccgg cgtctaccca  10860
ttcatgtggg gcggcgccta ctgcttctgc gacactgaaa atacgcaatt gagcgaagca  10920
catgtggaga agtccgaatc atgcaaaaca gaatttgcat cagcatatag ggctcatacc  10980
gcatccgcat cagctaagct ccgcgtcctt taccaaggaa ataatgttac tgtatctgct  11040
tatgcaaacg gcgatcatgc cgtcacagtt aaggacgcta aattcattgt ggggccaatg  11100
tcttcagcct ggacaccttt tgacaataaa atcgtggtgt acaaaggcga cgtctacaac  11160
atggactacc cgcccttcgg cgcaggaaga ccaggacaat ttggcgacat ccaaagtcgc  11220
acgcctgaga gcgaagacgt ctatgctaac acacaactgg tactgcagag accgtccgcg  11280
ggtacggtgc acgtgccgta ctctcaggca ccatctggct tcaagtattg gctaaaagaa  11340
cgaggggcgt cgctgcagca cacagcacca tttggctgtc aaatagcaac aaacccggta  11400
agagcgatga actgcgccgt agggaacatg cctatctcca tcgacatacc ggacgcggcc  11460
ttcactaggg tcgtcgacgc gccatcttta acggacatgt cgtgtgaggt accagcctgc  11520
acccactcct cagactttgg gggcgtagcc atcattaaat atgcagccag caagaaaggc  11580
aagtgtgcgg tgcattcgat gactaacgcc gtcactattc gggaagctga aatagaagta  11640
gaagggaact ctcagttgca aatctctttt tcgacggccc tagccagcgc cgaattccgc  11700
gtacaagtct gttctacaca agtacactgt gcagccgagt gccatccacc gaaagaccat  11760
atagtcaatt acccggcgtc acacaccacc ctcggggtcc aagacatttc cgttacggcg  11820
atgtcatggg tgcagaagat cacgggaggt gtgggactgg ttgtcgctgt tgcagcactg  11880
atcctaatcg tggtgctatg cgtgtcgttt agcaggcact aacttgacaa ctaggtacga  11940
aggtatatgt gtcccctaag agacacacca catatagcta agaatcaata gataagtata  12000
gatcaaaggg ctgaacaacc cctgaatagt aacaaaatat aaaaatcaac aaaaatcata  12060
aaatagaaaa ccagaaacag aagtaggtaa gaaggtatat gtgtccccta agagacacac  12120
catatatagc taagaatcaa tagataagta tagatcaaag ggctgaataa cccctgaata  12180
ataacaaaat ataaaaatca ataaaaatca taaaatagaa aaccataaac agaagtagtt  12240
caaagggcta taaaacccct gaatagtaac aaaacataaa actaataaaa atcaaatgaa  12300
taccataatt ggcaatcgga agagatgtag gtacttaagc ttcctaaaag cagccgaact  12360
cgctttgaga tgtaggcgta gcacaccgaa ctcttccata attctccgaa cccacaggga  12420
cgtaggagat gttcaaagtg gctataaaac cctgaacagt aataaaacat aaaattaata  12480
aggatcaaat gagtaccata attggcaaac ggaagagatg taggtactta agcttcctaa  12540
```

aagcagccga actcactttg agatgtaggc atagcatacc gaactcttcc acaattctcc 12600
gtacccatag ggacgtagga gatgttattt tgtttttaat atttcaaaaa aaaaaaaaaa 12660
aaaaaaaagg gtactgggtc ggcatggcat ctccacctcc tcgcggtccg acctgggcat 12720
ccgaaggagg acgcacgtcc actcggatgg ctaagggaga gccacgagct cctcgacaga 12780
tcataatcag ccataccaca tttgtagagg ttttacttgc tttaaaaaac ctcccacacc 12840
tccccctgaa cctgaaacat aaaatgaatg caattgttgt tgttaacttg tttattgcag 12900
cttataatgg ttacaaataa agcaatagca tcacaaattt cacaaataaa gcattttttt 12960
cactgcattc tagttgtggt ttgtccaaac tcatcaagat gcggccgcca ctgtgctgga 13020
tatctgcaga attccaccac actggactag tggatcagct taagtttaaa ccgctgatca 13080
gcctcgactg tgccttctag ttgccagcca tctgttgttt gcccctcccc cgtgccttcc 13140
ttgaccctgg aaggtgccac tcccactgtc ctttcctaat aaaatgagga aattgcatcg 13200
cattgtctga gtaggtgtca ttctattctg gggggtgggg tggggcagga c 13251

<210> SEQ ID NO 2
<211> LENGTH: 12923
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
ggcgcgcctg acattgatta ttgactagtt attaatagta atcaattacg gggtcattag 60
ttcatagccc atatatggag ttccgcgtta cataacttac ggtaaatggc ccgcctggct 120
gaccgcccaa cgacccccgc ccattgacgt caataatgac gtatgttccc atagtaacgc 180
caatagggac tttccattga cgtcaatggg tggagtattt acggtaaact gcccacttgg 240
cagtacatca agtgtatcat atgccaagta cgccccctat tgacgtcaat gacggtaaat 300
ggcccgcctg gcattatgcc cagtacatga ccttatggga ctttcctact tggcagtaca 360
tctacgtatt agtcatcgct attaccatgg tgatgcggtt ttggcagtac atcaatgggc 420
gtggatagcg gtttgactca cggggatttc caagtctcca ccccattgac gtcaatggga 480
gtttgttttg gcaccaaaat caacgggact ttccaaaatg tcgtaacaac tccgccccat 540
tgacgcaaat gggcggtagg cgtgtacggt gggaggtcta tataagcaga gctctctggc 600
taactagaga tggctgcgtg agacacacgt agcctaccag tttcttactg ctctactctg 660
caaagcaaga gattaataac ccatcatgga ttctgtgtac gtggacatag acgctgacag 720
cgcctttttg aaggccctgc aacgtgcgta ccccatgttt gaggtggaac ctaggcaggt 780
cacatcgaat gaccatgcta atgctagagc gttctcgcat ctagccataa aactaataga 840
gcaggaaatt gatcccgact caaccatcct ggatataggt agtgcgccag caaggaggat 900
gatgtcggac aggaagtacc actgcgtttg cccgatgcgc agcgcagaag atcccgagag 960
actcgctaat tatgcgagaa agctcgcatc tgccgcagga aaagtcctgg acagaaacat 1020
ttctggaaag atcggggact tacaagcggt gatggccgtg ccagacacgg agacgccaac 1080
attttgctta cacacagatg tctcatgtag acagagagca gacgtcgcga tataccaaga 1140
cgtctatgct gtacacgcac ccacgtcgct ataccaccag gcgattaaag gagtccgagt 1200
ggcgtactgg gtagggttcg acacaacccc gttcatgtac aacgctatgg cgggtgccta 1260
cccctcatac tcgacaaatt gggcggatga gcaggtactg aaggctaaga acataggatt 1320

-continued

```
atgttcaaca gacctgacgg aaggtagacg aggcaaattg tctatcatga gagggaaaaa   1380
gctaaaaccg tgcgaccgtg tgctgttctc agtagggtca acgctttacc cggaaagccg   1440
cacgctactt aagagctggc acctaccatc ggtgttccat ctaaagggca agcttagctt   1500
cacatgccgc tgtgacacag tggtttcgtg tgagggctac gtcgttaaga gaataacgat   1560
gagcccaggc ctttatggaa aaaccatagg gtatgcggta acccaccacg cagacggatt   1620
cttgatgtgc aagactaccg acacggttga cggcgaaaga gtgtcattct cggtgtgcac   1680
gtacgtgccg gcgaccattt gtgatcaaat gaccggcatc cttgctacag aagtcacgcc   1740
ggaggatgca cagaagctgt tggtggggct gaaccagagg atagtggtta acggcagaac   1800
gcaacggaac acgaacacca tgaagaacta cctacttccc gtggtcgccc aggccttcag   1860
taagtgggca aaggagtgcc ggaaggacat ggaagatgag aagcttctgg gggtcagaga   1920
aagaacacta acctgctgct gtctatgggc atttaagaag cagaaaacac acacggtcta   1980
caagaggcct gatacccagt caatccagaa ggttcaggcc gaatttgaca gctttgtagt   2040
accgggcctg tggtcgtccg ggttgtcaat cccgttgagg actagaatca agtggttgtt   2100
acgcaaggtg ccgaaaacag acctgatccc atacagcggg aatgcccaag aagcccagga   2160
tgcagaaaaa gaagcagagg aagaacgaga agcagaactg actcatgagg ctctaccacc   2220
cctacaggca gcacaggaag atgtccaggt cgaaatcgac gtggaacagc ttgaggatag   2280
agctggtgct ggaataatag agactccgag aggcgctatc aaagttactg cccaactaac   2340
agaccacgtc gtgggggagt acctggtact ttccccgcag accgtactac gcagccagaa   2400
gctcagcctg atccacgctt tagcggagca agtgaagacg tgtacgcaca gcggacgagc   2460
agggaggtat gcggtcgaag cgtacgatgg ccgagtccta gtgccctcag gctatgcaat   2520
ttcgcctgaa gacttccaga gtctaagcga aagcgcaacg atggtgtaca acgaaagaga   2580
gttcgtaaac agaaagttac accacattgc gatgcacgga ccagccctga acactgacga   2640
agagtcgtat gagctggtga gggcagagag gacagaacac gagtacgtct acgacgtgga   2700
ccagagaaga tgctgtaaga aggaagaagc tgcaggactg gtactggtgg gcgacttgac   2760
taatccgccc taccacgaat tcgcatacga agggctaaaa attcgccccg cctgcccata   2820
caaaattgca gtcataggag tcttcggggt accaggatct ggcaagtcag ccattatcaa   2880
gaacctagtt accaggcaag acctggtgac tagcggaaag aaagaaaact gccaagaaat   2940
cagcaccgac gtgatgagac agagaggtct agagatatct gcacgtacgg tagattcgct   3000
gctcttgaat ggatgcaaca gaccagtcga cgtgttgtac gtagacgagg cgtttgcgtg   3060
ccactctgga acgttacttg ctttgatcgc cttggtgaga ccaagacaga aagttgtact   3120
ttgtggtgac ccgaagcagt gcggcttctt caatatgatg cagatgaaag tcaactacaa   3180
tcataacatc tgcacccaag tgtaccacaa aagtatctcc aggcggtgta cactgcctgt   3240
gactgccatt gtgtcatcgt tgcattacga aggcaaaatg cgcactacga atgagtacaa   3300
catgccgatt gtagtggaca ctacaggctc aacgaaacct gaccctggag acctcgtgtt   3360
aacgtgcttc agagggtggg ttaaacaact gcaaattgac tatcgtggac acgaggtcat   3420
gacagcagcc gcatcccaag ggttaactag aaaaggagtt tacgcagtta ggcaaaaagt   3480
taacgaaaac ccactctatg catcaacatc agagcacgtc aacgtactcc taacgcgtac   3540
ggaaggtaaa ctggtatgga agacactctc tggtgacccg tggataaaga cgctgcagaa   3600
cccaccgaaa ggaaacttca aagcaactat taaggagtgg gaggtggagc acgcatcgat   3660
```

-continued

```
aatggcgggc atctgcagtc accaagtgac ctttgacaca ttccaaaaca aagccaacgt   3720
ttgctgggct aagagcttgg tccctatcct cgaaacagcg gggataaaac taaatgatag   3780
gcagtggtcc cagataattc aagccttcaa agaagacaaa gcatactcac ccgaagtagc   3840
cctgaatgaa atatgcacgc gcatgtatgg ggtggatcta gacagtgggc tattctctaa   3900
accgttggta tctgtgtatt acgcggataa ccattgggat aataggccgg gaggaaagat   3960
gttcggattc aaccctgagg cagcgtccat tctagaaaga aagtacccat ttacaaaagg   4020
aaagtggaac atcaacaagc agatctgcgt gactaccagg aggatagaag acttcaaccc   4080
taccaccaac attataccgg tcaacaggag actaccacac tcattagtgg ccgaacaccg   4140
cccagtaaaa ggggaaagaa tggaatggct ggttaacaag ataaacggac accacgtact   4200
cctggttagc ggctataacc ttgcactgcc tactaagaga gtcacctggg tagcgccact   4260
aggtgtccgc ggagcggact atacatacaa cctagagctg ggtctaccag caacrcttgg   4320
taggtatgac ctagtggtca taaacatcca cacacctttt cgcatacacc attaccaaca   4380
gtgcgtagat cacgcaatga aactgcaaat gctagggggt gactcactga gactgctcaa   4440
accgggtggc tctctattga tcagagcata cggttacgca gatagaacca gtgaacgagt   4500
catctgcgta ctgggacgca agtttagatc gtctagagca ttgaaaccac catgtgtcac   4560
cagtaatact gagatgtttt tcctatttag caattttgac aatggcagaa ggaattttac   4620
aacgcatgtc atgaacaatc aactgaatgc agcctttgta ggacaggcca cccgagcagg   4680
atgtgcacca tcgtaccggg taaaacgcat ggacatcgcg aagaacgatg aagagtgcgt   4740
ggttaacgcc gccaaccctc gcgggttacc aggtgacggt gtttgcaagg cagtatataa   4800
aaagtggccg gagtccttta aaaacagtgc aacaccagta ggaaccgcaa aaacagttat   4860
gtgcggtacg tatccagtaa tccacgccgt aggaccaaac ttctcaaatt attcggagtc   4920
tgaaggggac cgggaattgg cggctgccta tcgagaagtc gcaaaggaag taactagact   4980
gggagtaaat agcgtagcta tacctctcct ctccacaggt gtatactcag gagggaaaga   5040
caggctaacc cagtcactga accacctctt tacagccatg gactcgacgg atgcagacgt   5100
ggtcatctac tgccgagaca aggaatggga gaagaaaata tctgaggcca tacagatgcg   5160
gacccaagtg gagctgctgg atgagcacat ctccatagac tgcgatgtca ttcgcgtgca   5220
ccctgacagt agcttggcag gcagaaaagg atacagcacc acggaaggcg cactgtattc   5280
atatctagaa gggacacgtt ttcaccagac ggcagtggat atggcagaga tatacactat   5340
gtggccaaag caaacagagg ccaatgagca agtctgccta tatgccctgg gggaaagtat   5400
tgaatcaatc aggcagaaat gcccggtgga tgatgcagac gcatcatctc ccccgaaaac   5460
tgtcccgtgt ctttgccggt atgccatgac tcctgaacgc gtcacccgac ttcgcatgaa   5520
ccatgtcaca aatataattg tgtgttcttc atttcccctt ccaaagtaca agatagaagg   5580
agtgcaaaaa gtcaaatgct ccaaggtaat gttattcgat cacaatgtgc catcgcgcgt   5640
aagtccaagg gaatacagat cttcccagga gtctgtacag gaagtgagta cgacaacgtc   5700
attgacgcat agccagtttg atctaagcgc cgatggcgag acactgcctg tcccgtcaga   5760
cctggatgct gacgccccag ccctagaacc ggccctagac gacggggcgg tacatacatt   5820
accaaccata atcggaaacc ttgcggccgt gtctgactgg gtaatgagca ccgtacctgt   5880
cgcgccgcct agaagaagga gagggagaaa cctgactgtg acatgtgacg agagagaagg   5940
gaatataaca cccatggcta gcgtccgatt ctttagagca gagctgtgtc cggccgtaca   6000
agaaacagcg gagacgcgtg acacagctat ttcccttcag gcaccgccaa gtaccaccat   6060
```

-continued

```
ggaactgagc catccaccga tctccttcgg agcaccaagc gagacgttcc ccatcacatt   6120
tggggacttc gacgaaggag aaatcgaaag cttgtcttct gagctactaa ctttcggaga   6180
cttcctaccc ggtgaagtgg atgatctgac agatagcgac tggtccacgt gcccagacac   6240
ggacgacgag ttatgactag acagggcagg tgggtatata ttctcgtcgg acactggtcc   6300
aggccattta caacagaagt cggtacgcca gtcagtgctg ccggtaaaca ccctggagga   6360
agtccacgag gagaagtgtt acccacctaa gctggatgaa ttaaaggagc aactactact   6420
taagaaactc caggagagtg cgtccatggc caatagaagc aggtatcagt cacgcaaagt   6480
ggaaaatatg aaagcaacaa tcatccagag actaaagaga ggctgtaaac tgtatttaat   6540
ggcagagacc ccgaaagtcc cgacttatcg gaccatatac ccggcgcctg tgtactcgcc   6600
tccgatcaat gtccgattgt ccaaccccga gtccgcagtg gcagcatgta atgagttctt   6660
agctagaaac tacccaactg tttcatcata ccaaatcacc gacgagtatg atgcatatct   6720
agacatggtg gacgggtcgg agagttgctt ggaccgagcg acattcaatc cgtcaaaact   6780
taggagctac ccgaaacaac atgcttatca cgcgccttct atcagaagcg ctgtaccttc   6840
cccattccag aacacactac agaatgtact ggcagcagcc acgaaaagga actgcaacgt   6900
cacacagatg agggaattac ccactttgga ctcagcagta ttcaacgtgg agtgttttaa   6960
aaaattcgca tgtaaccgag aatactggga agaatttgca gccagcccta tcaggataac   7020
aactgagaat ctaacaacct atgtcactaa actaaagggg ccaaaagcag cagcgctgtt   7080
tgcaaaaacc cataatctgc tgccactgca ggatgtacca atggataggt tcacagtaga   7140
tatgaaaagg gatgtgaagg taactcctgg tacaaagcat acagaggaaa gacctaaggt   7200
gcaggttata caggcggctg aacccttggc aacagcgtac ctatgtggaa ttcacagaga   7260
actggttagg agattgaacg ccgtcctcct acccaatgtg catacactat ttgacatgtc   7320
tgccgaggac ttcgatgcca ttatagccgc acacttcaag ccaggagacg ctgttttaga   7380
aacggacata gcctcctttg ataagagcca agatgattca cttgcgctta ccgccttaat   7440
gctgttagaa gatttgggag tggatcactc cctgttggac ttgatagagg ctgctttcgg   7500
agagatttcc agctgtcatc tgccgacagg tacgcgcttc aagttcggcg ctatgatgaa   7560
atccggtatg ttcctaactc tgttcgtcaa cacgttgtta aatatcacca tcgctagccg   7620
ggtgttggaa gatcgtctga caaaatccgc atgcgcggcc ttcatcggcg acgacaacat   7680
aatacatggt gtcgtctccg atgaattgat ggcagccaga tgcgctactt ggatgaacat   7740
ggaagtgaag atcatagatg cagttgtatc ccagaaagct ccttactttt gtggagggtt   7800
tatactgcat gatactgtga caggaacagc ttgcagagtg gcggacccgc taaaaaggtt   7860
atttaaattg ggcaaaccgt tagcggcagg tgacgaacaa gatgaagaca gaagacgggc   7920
gctggctgat gaagtaatca gatggcaacg aacagggcta atagatgagc tggagaaagc   7980
ggtgtactct aggtacgaag tgcagggtat atcagttgcg gtaatgtcca tggccacctt   8040
tgcaagctcc agatccaact tcgagaagct cagaggaccc gtcataactt tgtacggcgg   8100
tcctaaatag gtacgcacta cagctaccta ttttgcagaa gccgacagca ggtacctaaa   8160
taccaatcag ccataatgga gtttatccca acccaaactt tctacaatag gaggtaccag   8220
cctcgacctt ggactccgcg ccctactatc caagttatca gacccagacc gcgtccgcaa   8280
aggaaagccg ggcaacttgc ccagctgatc tcagcagtta ataaactgac aatgcgcgcg   8340
gtacctcaac agaagccgcg caagaatcgg aagaataaga agcaaaagca aaagcagcag   8400
```

-continued

```
gcgccacgaa acaacatgaa tcaaaagaag cagcccccta aaaagaaacc ggctcaaaag   8460
aaaaagaagc cgggccgtag agagagaatg tgcatgaaaa tcgaaaatga ttgcatcttc   8520
gaagtcaagc atgaaggtaa ggtaacaggt tacgcgtgct tggtagggga caaagtaatg   8580
aagccagcac acgtaaaggg gaccatcgat aatgcggacc tggccaaatt ggccttcaag   8640
cggtcatcta agtacgacct tgaatgcgcg cagatacccg tgcacatgaa gtccgacgct   8700
tcgaagttca cccatgagaa accggagggg tactacaact ggcaccacgg agcagtacag   8760
tactcaggag gccggttcac catccctaca ggtgcgggca aaccagggga cagcggtaga   8820
ccgatcttcg acaacaaggg gcgcgtggtg gccatagttt taggaggagc taatgaagga   8880
gcccgtacag ccctctcggt ggtgacctgg aacaaagaca tcgtcacgaa aatcacccct   8940
gagggggccg aagagtggag tcttgccatt ccagttatgt gcctgctggc aaataccacg   9000
ttcccctgct cccagccccc ttgcacaccc tgctgctacg aaaaagagcc ggagaaaacc   9060
ctgcgcatgc tagaagacaa cgtcatgagc cccgggtact atcagctgct acaagcatcc   9120
ttaacatgtt ctcccgccg ccagcgacgc agtattaagg acaacttcaa tgtctataaa   9180
gccataagac cgtacctagc tcactgtccc gactgtggag aagggcactc gtgccatagt   9240
cccgtagcgc tagaacgcat cagaaacgaa gcgacagacg ggacgctgaa aatccaggtt   9300
tccttgcaaa tcggaataaa gacggatgat agccatgatt ggaccaagct gcgttacatg   9360
gacaatcata tgccagcaga cgcagagagg gccaggctat ttgtaagaac gtcagcaccg   9420
tgcacgatta ctggaacaat gggacacttc atcctggccc gatgtccgaa aggagaaact   9480
ctgacggtgg gattcactga cggtaggaag atcagtcact catgtacgca cccatttcac   9540
cacgaccctc ctgtgatagg ccgggaaaaa tttcattccc gaccgcagca cggtagagaa   9600
ctaccttgca gcacgtacgc gcagagcacc gctgcaactg ccgaggagat agaggtacat   9660
atgcccccag acaccccaga tcgcacattg atgtcacaac agtccggtaa tgtaaagatc   9720
acagtcaata gtcagacggt gcggtacaag tgtaattgcg gtgactcaaa tgaaggacta   9780
accactacag acaaagtgat taataactgc aaggttgatc aatgccatgc cgcggtcacc   9840
aatcacaaaa aatggcagta taattcccct ctggtcccgc gtaatgctga actcggggac   9900
cgaaaaggaa aagttcacat tccgtttcct ctggcaaatg tgacatgcag ggtgcctaag   9960
gcaaggaacc ccaccgtgac gtacggaaaa aaccaagtca tcatgctgct gtatcctgac  10020
cacccaacgc tcctgtccta ccggaatatg ggagaagaac caaactatca agaagagtgg  10080
gtgacgcata agaaggagat caggttaacc gtgccgactg aagggctcga ggtcacgtgg  10140
ggcaacaacg agccgtacaa gtattggccg cagttatcca caaacggtac agcccacggc  10200
cacccgcatg agataatttt gtattattat gagctgtacc ctactatgac tgtggtagtt  10260
gtgtcagtgg cctcgttcgt actcctgtcg atggtgggtg tggcagtggg gatgtgcatg  10320
tgtgcacgac gcagatgcat tacaccgtac gaactgacac caggagctac cgtccctttc  10380
ctgcttagcc taatatgctg cattagaaca gctaaagcgg ccacatacca agaggctgcg  10440
gtatacctgt ggaacgagca gcagcctttg ttttggctgc aagcccttat tccgctggca  10500
gccctgattg tcctatgcaa ctgtctgaga ctcttaccat gcttttgtaa aacgttgact  10560
tttttagccg taatgagcgt cggtgcccac actgtgagcg cgtacgaaca cgtaacagtg  10620
atcccgaaca cggtgggagt accgtataag actctagtca acagaccggg ctacagcccc  10680
atggtactgg agatggagct tctgtcagtc actttggagc caacgctatc gcttgattac  10740
atcacgtgcg agtataaaac cgtcatcccg tctccgtacg tgaaatgctg cggtacagca  10800
```

-continued

```
gagtgcaagg acaagagcct acctgattac agctgtaagg tcttcaccgg cgtctaccca  10860
ttcatgtggg gcggcgccta ctgcttctgc gacactgaaa atacgcaatt gagcgaagca  10920
catgtggaga agtccgaatc atgcaaaaca gaatttgcat cagcatatag ggctcatacc  10980
gcatccgcat cagctaagct ccgcgtcctt taccaaggaa ataatgttac tgtatctgct  11040
tatgcaaacg gcgatcatgc cgtcacagtt aaggacgcta aattcattgt ggggccaatg  11100
tcttcagcct ggacaccttt tgacaataaa atcgtggtgt acaaaggcga cgtctacaac  11160
atggactacc cgcccttcgg cgcaggaaga ccaggacaat ttggcgacat ccaaagtcgc  11220
acgcctgaga gcgaagacgt ctatgctaac acacaactgg tactgcagag accgtccgcg  11280
ggtacggtgc acgtgccgta ctctcaggca ccatctggct tcaagtattg gctaaaagaa  11340
cgaggggcgt cgctgcagca cacagcacca tttggctgtc aaatagcaac aaacccggta  11400
agagcgatga actgcgccgt agggaacatg cctatctcca tcgacatacc ggacgcggcc  11460
ttcactaggg tcgtcgacgc gccatcttta acggacatgt cgtgtgaggt accagcctgc  11520
acccactcct cagactttgg gggcgtagcc atcattaaat atgcagccag caagaaaggc  11580
aagtgtgcgg tgcattcgat gactaacgcc gtcactattc gggaagctga aatagaagta  11640
gaagggaact ctcagttgca aatctctttt tcgacggccc tagccagcgc cgaattccgc  11700
gtacaagtct gttctacaca agtacactgt gcagccgagt gccatccacc gaaagaccat  11760
atagtcaatt acccggcgtc acacaccacc ctcggggtcc aagacatttc cgttacggcg  11820
atgtcatggg tgcagaagat cacgggaggt gtgggactgg ttgtcgctgt tgcagcactg  11880
atcctaatcg tggtgctatg cgtgtcgttt agcaggcact aacttgacaa ctaggtacga  11940
aggtatatgt gtcccctaag agacacacca catatagcta agaatcaata gataagtata  12000
gatcaaaggg ctgaacaacc cctgaatagt aacaaaatat aaaaatcaac aaaaatcata  12060
aaatagaaaa ccagaaacag aagtaggtaa gaaggtatat gtgtccccta agagacacac  12120
catatatagc taagaatcaa tagataagta tagatcaaag ggctgaataa cccctgaata  12180
ataacaaaat ataaaaatca ataaaaatca taaaatagaa aaccataaac agaagtagtt  12240
caaagggcta taaaacccct gaatagtaac aaaacataaa actaataaaa atcaaatgaa  12300
taccataatt ggcaatcgga agagatgtag gtacttaagc ttcctaaaag cagccgaact  12360
cgctttgaga tgtaggcgta gcacaccgaa ctcttccata attctccgaa cccacaggga  12420
cgtaggagat gttcaaagtg gctataaaac cctgaacagt aataaaacat aaaattaata  12480
aggatcaaat gagtaccata attggcaaac ggaagagatg taggtactta agcttcctaa  12540
aagcagccga actcactttg agatgtaggc atagcatacc gaactcttcc acaattctcc  12600
gtacccatag ggacgtagga gatgttattt tgtttttaat atttcaaaaa aaaaaaaaaa  12660
aaaaaagggt acgcggccgc cactgtgctg gatatctgca gaattccacc acactggact  12720
agtggatcag cttaagttta aaccgctgat cagcctcgac tgtgccttct agttgccagc  12780
catctgttgt ttgcccctcc cccgtgcctt ccttgaccct ggaaggtgcc actcccactg  12840
tcctttccta ataaaatgag gaaattgcat cgcattgtct gagtaggtgt cattctattc  12900
tggggggtgg ggtggggcag gac                                           12923
```

<210> SEQ ID NO 3
<211> LENGTH: 13031
<212> TYPE: DNA
<213> ORGANISM: Artificial Sequence
<220> FEATURE:

-continued

<223> OTHER INFORMATION: Description of Artificial Sequence: Synthetic polynucleotide

<400> SEQUENCE: 3

```
ggcgcgcctg acattgatta ttgactagtt attaatagta atcaattacg gggtcattag     60
ttcatagccc atatatggag ttccgcgtta cataacttac ggtaaatggc ccgcctggct    120
gaccgcccaa cgacccccgc ccattgacgt caataatgac gtatgttccc atagtaacgc    180
caatagggac tttccattga cgtcaatggg tggagtattt acggtaaact gcccacttgg    240
cagtacatca agtgtatcat atgccaagta cgccccctat tgacgtcaat gacggtaaat    300
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta tataagcaga gctctctggc    600
taactagaga tggctgcgtg agacacacgt agcctaccag tttcttactg ctctactctg    660
caaagcaaga gattaataac ccatcatgga ttctgtgtac gtggacatag acgctgacag    720
cgcctttttg aaggccctgc aacgtgcgta ccccatgttt gaggtggaac ctaggcaggt    780
cacatcgaat gaccatgcta atgctagagc gttctcgcat ctagccataa aactaataga    840
gcaggaaatt gatcccgact caaccatcct ggatataggt agtgcgccag caaggaggat    900
gatgtcggac aggaagtacc actgcgtttg cccgatgcgc agcgcagaag atcccgagag    960
actcgctaat tatgcgagaa agctcgcatc tgccgcagga aaagtcctgg acagaaacat   1020
ttctggaaag atcggggact tacaagcggt gatggccgtg ccagacacgg agacgccaac   1080
attttgctta cacacagatg tctcatgtag acagagagca gacgtcgcga tataccaaga   1140
cgtctatgct gtacacgcac ccacgtcgct ataccaccag gcgattaaag gagtccgagt   1200
ggcgtactgg gtagggttcg acacaacccc gttcatgtac aacgctatgg cgggtgccta   1260
cccctcatac tcgacaaatt gggcggatga gcaggtactg aaggctaaga acataggatt   1320
atgttcaaca gacctgacgg aaggtagacg aggcaaattg tctatcatga gagggaaaaa   1380
gctaaaaccg tgcgaccgtg tgctgttctc agtagggtca acgctttacc cggaaagccg   1440
cacgctactt aagagctggc acctaccatc ggtgttccat ctaaagggca agcttagctt   1500
cacatgccgc tgtgacacag tggtttcgtg tgagggctac gtcgttaaga gaataacgat   1560
gagcccaggc ctttatggaa aaaccatagg gtatgcggta acccaccacg cagacggatt   1620
cttgatgtgc aagactaccg acacggttga cggcgaaaga gtgtcattct cggtgtgcac   1680
gtacgtgccg gcgaccattt gtgatcaaat gaccggcatc cttgctacag aagtcacgcc   1740
ggaggatgca cagaagctgt tggtggggct gaaccagagg atagtggtta acggcagaac   1800
gcaacggaac acgaacacca tgaagaacta cctacttccc gtggtcgccc aggccttcag   1860
taagtgggca aaggagtgcc ggaaggacat ggaagatgag aagcttctgg gggtcagaga   1920
aagaacacta acctgctgct gtctatgggc atttaagaag cagaaaacac acacggtcta   1980
caagaggcct gatacccagt caatccagaa ggttcaggcc gaatttgaca gctttgtagt   2040
accgggcctg tggtcgtccg ggttgtcaat cccgttgagg actagaatca agtggttgtt   2100
acgcaaggtg ccgaaaacag acctgatccc atacagcggg aatgcccaag aagcccagga   2160
tgcagaaaaa gaagcagagg aagaacgaga agcagaactg actcatgagg ctctaccacc   2220
```

-continued

```
cctacaggca gcacaggaag atgtccaggt cgaaatcgac gtggaacagc ttgaggatag   2280
agctggtgct ggaataatag agactccgag aggcgctatc aaagttactg cccaactaac   2340
agaccacgtc gtgggggagt acctggtact ttccccgcag accgtactac gcagccagaa   2400
gctcagcctg atccacgctt tagcggagca agtgaagacg tgtacgcaca gcggacgagc   2460
agggaggtat gcggtcgaag cgtacgatgg ccgagtccta gtgccctcag gctatgcaat   2520
ttcgcctgaa gacttccaga gtctaagcga aagcgcaacg atggtgtaca acgaaagaga   2580
gttcgtaaac agaaagttac accacattgc gatgcacgga ccagccctga acactgacga   2640
agagtcgtat gagctggtga gggcagagag gacagaacac gagtacgtct acgacgtgga   2700
ccagagaaga tgctgtaaga aggaagaagc tgcaggactg gtactggtgg gcgacttgac   2760
taatccgccc taccacgaat tcgcatacga agggctaaaa attcgccccg cctgcccata   2820
caaaattgca gtcataggag tcttcggggt accaggatct ggcaagtcag ccattatcaa   2880
gaacctagtt accaggcaag acctggtgac tagcggaaag aaagaaaact gccaagaaat   2940
cagcaccgac gtgatgagac agagaggtct agagatatct gcacgtacgg tagattcgct   3000
gctcttgaat ggatgcaaca gaccagtcga cgtgttgtac gtagacgagg cgtttgcgtg   3060
ccactctgga acgttacttg ctttgatcgc cttggtgaga ccaagacaga aagttgtact   3120
ttgtggtgac ccgaagcagt gcggcttctt caatatgatg cagatgaaag tcaactacaa   3180
tcataacatc tgcacccaag tgtaccacaa aagtatctcc aggcggtgta cactgcctgt   3240
gactgccatt gtgtcatcgt tgcattacga aggcaaaatg cgcactacga atgagtacaa   3300
catgccgatt gtagtggaca ctacaggctc aacgaaacct gaccctggag acctcgtgtt   3360
aacgtgcttc agagggtggg ttaaacaact gcaaattgac tatcgtggac acgaggtcat   3420
gacagcagcc gcatcccaag ggttaactag aaaaggagtt tacgcagtta ggcaaaaagt   3480
taacgaaaac ccactctatg catcaacatc agagcacgtc aacgtactcc taacgcgtac   3540
ggaaggtaaa ctggtatgga agacactctc tggtgacccg tggataaaga cgctgcagaa   3600
cccaccgaaa ggaaacttca aagcaactat taaggagtgg gaggtggagc acgcatcgat   3660
aatggcgggc atctgcagtc accaagtgac ctttgacaca ttccaaaaca aagccaacgt   3720
ttgctgggct aagagcttgg tccctatcct cgaaacagcg gggataaaac taaatgatag   3780
gcagtggtcc cagataattc aagccttcaa agaagacaaa gcatactcac ccgaagtagc   3840
cctgaatgaa atatgcacgc gcatgtatgg ggtggatcta gacagtgggc tattctctaa   3900
accgttggta tctgtgtatt acgcggataa ccattgggat aataggccgg gaggaaagat   3960
gttcggattc aaccctgagg cagcgtccat tctagaaaga aagtacccat ttacaaaagg   4020
aaagtggaac atcaacaagc agatctgcgt gactaccagg aggatagaag acttcaaccc   4080
taccaccaac attataccgg tcaacaggag actaccacac tcattagtgg ccgaacaccg   4140
cccagtaaaa ggggaaagaa tggaatggct ggttaacaag ataaacggac accacgtact   4200
cctggttagc ggctataacc ttgcactgcc tactaagaga gtcacctggg tagcgccact   4260
aggtgtccgc ggagcggact atacatacaa cctagagctg ggtctaccag caacrcttgg   4320
taggtatgac ctagtggtca taaacatcca cacacctttt cgcatacacc attaccaaca   4380
gtgcgtagat cacgcaatga aactgcaaat gctagggggt gactcactga gactgctcaa   4440
accgggtggc tctctattga tcagagcata cggttacgca gatagaacca gtgaacgagt   4500
catctgcgta ctgggacgca agtttagatc gtctagagca ttgaaaccac catgtgtcac   4560
cagtaatact gagatgtttt tcctatttag caattttgac aatggcagaa ggaattttac   4620
```

-continued

```
aacgcatgtc atgaacaatc aactgaatgc agcctttgta ggacaggcca cccgagcagg   4680
atgtgcacca tcgtaccggg taaaacgcat ggacatcgcg aagaacgatg aagagtgcgt   4740
ggttaacgcc gccaaccctc gcgggttacc aggtgacggt gtttgcaagg cagtatataa   4800
aaagtggccg gagtccttta aaaacagtgc aacaccagta ggaaccgcaa aaacagttat   4860
gtgcggtacg tatccagtaa tccacgccgt aggaccaaac ttctcaaatt attcggagtc   4920
tgaaggggac cgggaattgg cggctgccta tcgagaagtc gcaaaggaag taactagact   4980
gggagtaaat agcgtagcta tacctctcct ctccacaggt gtatactcag gagggaaaga   5040
caggctaacc cagtcactga accacctctt tacagccatg gactcgacgg atgcagacgt   5100
ggtcatctac tgccgagaca aggaatggga gaagaaaata tctgaggcca tacagatgcg   5160
gacccaagtg gagctgctgg atgagcacat ctccatagac tgcgatgtca ttcgcgtgca   5220
ccctgacagt agcttggcag gcagaaaagg atacagcacc acggaaggcg cactgtattc   5280
atatctagaa gggacacgtt ttcaccagac ggcagtggat atggcagaga tatacactat   5340
gtggccaaag caaacagagg ccaatgagca agtctgccta tatgccctgg gggaaagtat   5400
tgaatcaatc aggcagaaat gcccggtgga tgatgcagac gcatcatctc ccccgaaaac   5460
tgtcccgtgt ctttgccggt atgccatgac tcctgaacgc gtcacccgac ttcgcatgaa   5520
ccatgtcaca aatataattg tgtgttcttc atttcccctt ccaaagtaca agatagaagg   5580
agtgcaaaaa gtcaaatgct ccaaggtaat gttattcgat cacaatgtgc catcgcgcgt   5640
aagtccaagg gaatacagat cttcccagga gtctgtacag gaagtgagta cgacaacgtc   5700
attgacgcat agccagtttg atctaagcgc cgatggcgag acactgcctg tcccgtcaga   5760
cctggatgct gacgccccag ccctagaacc ggccctagac gacggggcgg tacatacatt   5820
accaaccata atcggaaacc ttgcggccgt gtctgactgg gtaatgagca ccgtacctgt   5880
cgcgccgcct agaagaagga gagggagaaa cctgactgtg acatgtgacg agagagaagg   5940
gaatataaca cccatggcta gcgtccgatt ctttagagca gagctgtgtc cggccgtaca   6000
agaaacagcg gagacgcgtg acacagctat ttcccttcag gcaccgccaa gtaccaccat   6060
ggaactgagc catccaccga tctccttcgg agcaccaagc gagacgttcc ccatcacatt   6120
tggggacttc gacgaaggag aaatcgaaag cttgtcttct gagctactaa ctttcggaga   6180
cttcctaccc ggtgaagtgg atgatctgac agatagcgac tggtccacgt gcccagacac   6240
ggacgacgag ttatgactag acagggcagg tgggtatata ttctcgtcgg acactggtcc   6300
aggccattta caacagaagt cggtacgcca gtcagtgctg ccggtaaaca ccctggagga   6360
agtccacgag gagaagtgtt acccacctaa gctggatgaa ttaaaggagc aactactact   6420
taagaaactc caggagagtg cgtccatggc caatagaagc aggtatcagt cacgcaaagt   6480
ggaaaatatg aaagcaacaa tcatccagag actaaagaga ggctgtaaac tgtatttaat   6540
ggcagagacc ccgaaagtcc cgacttatcg gaccatatac ccggcgcctg tgtactcgcc   6600
tccgatcaat gtccgattgt ccaaccccga gtccgcagtg gcagcatgta atgagttctt   6660
agctagaaac tacccaactg tttcatcata ccaaatcacc gacgagtatg atgcatatct   6720
agacatggtg gacgggtcgg agagttgctt ggaccgagcg acattcaatc cgtcaaaact   6780
taggagctac ccgaaacaac atgcttatca cgcgccttct atcagaagcg ctgtaccttc   6840
cccattccag aacacactac agaatgtact ggcagcagcc acgaaaagga actgcaacgt   6900
cacacagatg agggaattac ccactttgga ctcagcagta ttcaacgtgg agtgttttaa   6960
```

-continued aaaattcgca tgtaaccgag aatactggga agaatttgca gccagcccta tcaggataac 7020
aactgagaat ctaacaacct atgtcactaa actaaagggg ccaaaagcag cagcgctgtt 7080
tgcaaaaacc cataatctgc tgccactgca ggatgtacca atggataggt tcacagtaga 7140
tatgaaaagg gatgtgaagg taactcctgg tacaaagcat acagaggaaa gacctaaggt 7200
gcaggttata caggcggctg aacccttggc aacagcgtac ctatgtggaa ttcacagaga 7260
actggttagg agattgaacg ccgtcctcct acccaatgtg catacactat ttgacatgtc 7320
tgccgaggac ttcgatgcca ttatagccgc acacttcaag ccaggagacg ctgttttaga 7380
aacggacata gcctcctttg ataagagcca agatgattca cttgcgctta ccgccttaat 7440
gctgttagaa gatttgggag tggatcactc cctgttggac ttgatagagg ctgctttcgg 7500
agagatttcc agctgtcatc tgccgacagg tacgcgcttc aagttcggcg ctatgatgaa 7560
atccggtatg ttcctaactc tgttcgtcaa cacgttgtta aatatcacca tcgctagccg 7620
ggtgttggaa gatcgtctga caaaatccgc atgcgcggcc ttcatcggcg acgacaacat 7680
aatacatggt gtcgtctccg atgaattgat ggcagccaga tgcgctactt ggatgaacat 7740
ggaagtgaag atcatagatg cagttgtatc ccagaaagct ccttactttt gtggagggtt 7800
tatactgcat gatactgtga caggaacagc ttgcagagtg gcggacccgc taaaaaggtt 7860
atttaaattg ggcaaaccgt tagcggcagg tgacgaacaa gatgaagaca gaagacgggc 7920
gctggctgat gaagtaatca gatggcaacg aacagggcta atagatgagc tggagaaagc 7980
ggtgtactct aggtacgaag tgcagggtat atcagttgcg gtaatgtcca tggccacctt 8040
tgcaagctcc agatccaact tcgagaagct cagaggaccc gtcataactt tgtacggcgg 8100
tcctaaatag gtacgcacta cagctaccta ttttgcagaa gccgacagca ggtacctaaa 8160
taccaatcag ccataatgga gtttatccca acccaaactt tctacaatag gaggtaccag 8220
cctcgacctt ggactccgcg ccctactatc caagttatca gacccagacc gcgtccgcaa 8280
aggaaagccg ggcaacttgc ccagctgatc tcagcagtta ataaactgac aatgcgcgcg 8340
gtacctcaac agaagccgcg caagaatcgg aagaataaga agcaaaagca aaagcagcag 8400
gcgccacgaa acaacatgaa tcaaaagaag cagcccccta aaaagaaacc ggctcaaaag 8460
aaaaagaagc cgggccgtag agagagaatg tgcatgaaaa tcgaaaatga ttgcatcttc 8520
gaagtcaagc atgaaggtaa ggtaacaggt tacgcgtgct tggtagggga caaagtaatg 8580
aagccagcac acgtaaaggg gaccatcgat aatgcggacc tggccaaatt ggccttcaag 8640
cggtcatcta agtacgacct tgaatgcgcg cagatacccg tgcacatgaa gtccgacgct 8700
tcgaagttca cccatgagaa accggagggg tactacaact ggcaccacgg agcagtacag 8760
tactcaggag gccggttcac catccctaca ggtgcgggca aaccagggga cagcggtaga 8820
ccgatcttcg acaacaaggg gcgcgtggtg gccatagttt taggaggagc taatgaagga 8880
gcccgtacag ccctctcggt ggtgacctgg aacaaagaca tcgtcacgaa aatcacccct 8940
gagggggccg aagagtggag tcttgcctag aggacccgtc ataactttgt acggcggtcc 9000
taaataggta cgcactacag ctacctattt tgcagaagcc gacagcaggt acctaaatac 9060
caatcagcca taatgattcc agttatgtgc ctgctggcaa ataccacgtt cccctgctcc 9120
cagcccccctt gcacaccctg ctgctacgaa aaagagccgg agaaaaccct gcgcatgcta 9180
gaagacaacg tcatgagccc cgggtactat cagctgctac aagcatcctt aacatgttct 9240
ccccgccgcc agcgacgcag tattaaggac aacttcaatg tctataaagc cataagaccg 9300
tacctagctc actgtcccga ctgtggagaa gggcactcgt gccatagtcc cgtagcgcta 9360

-continued

```
gaacgcatca gaaacgaagc gacagacggg acgctgaaaa tccaggtttc cttgcaaatc   9420
ggaataaaga cggatgatag ccatgattgg accaagctgc gttacatgga caatcatatg   9480
ccagcagacg cagagagggc caggctattt gtaagaacgt cagcaccgtg cacgattact   9540
ggaacaatgg gacacttcat cctggcccga tgtccgaaag gagaaactct gacggtggga   9600
ttcactgacg gtaggaagat cagtcactca tgtacgcacc catttcacca cgaccctcct   9660
gtgataggcc gggaaaaatt tcattcccga ccgcagcacg gtagagaact accttgcagc   9720
acgtacgcgc agagcaccgc tgcaactgcc gaggagatag aggtacatat gcccccagac   9780
accccagatc gcacattgat gtcacaacag tccggtaatg taaagatcac agtcaatagt   9840
cagacggtgc ggtacaagtg taattgcggt gactcaaatg aaggactaac cactacagac   9900
aaagtgatta ataactgcaa ggttgatcaa tgccatgccg cggtcaccaa tcacaaaaaa   9960
tggcagtata attcccctct ggtcccgcgt aatgctgaac tcggggaccg aaaaggaaaa  10020
gttcacattc cgtttcctct ggcaaatgtg acatgcaggg tgcctaaggc aaggaacccc  10080
accgtgacgt acggaaaaaa ccaagtcatc atgctgctgt atcctgacca cccaacgctc  10140
ctgtcctacc ggaatatggg agaagaacca aactatcaag aagagtgggt gacgcataag  10200
aaggagatca ggttaaccgt gccgactgaa gggctcgagg tcacgtgggg caacaacgag  10260
ccgtacaagt attggccgca gttatccaca aacggtacag cccacggcca cccgcatgag  10320
ataattttgt attattatga gctgtaccct actatgactg tggtagttgt gtcagtggcc  10380
tcgttcgtac tcctgtcgat ggtgggtgtg gcagtgggga tgtgcatgtg tgcacgacgc  10440
agatgcatta caccgtacga actgacacca ggagctaccg tccctttcct gcttagccta  10500
atatgctgca ttagaacagc taaagcggcc acataccaag aggctgcggt atacctgtgg  10560
aacgagcagc agcctttgtt ttggctgcaa gcccttattc cgctggcagc cctgattgtc  10620
ctatgcaact gtctgagact cttaccatgc ttttgtaaaa cgttgacttt tttagccgta  10680
atgagcgtcg gtgcccacac tgtgagcgcg tacgaacacg taacagtgat cccgaacacg  10740
gtgggagtac cgtataagac tctagtcaac agaccgggct acagccccat ggtactggag  10800
atggagcttc tgtcagtcac tttggagcca acgctatcgc ttgattacat cacgtgcgag  10860
tataaaaccg tcatcccgtc tccgtacgtg aaatgctgcg gtacagcaga gtgcaaggac  10920
aagagcctac ctgattacag ctgtaaggtc ttcaccggcg tctacccatt catgtggggc  10980
ggcgcctact gcttctgcga cactgaaaat acgcaattga gcgaagcaca tgtggagaag  11040
tccgaatcat gcaaaacaga atttgcatca gcatataggg ctcataccgc atccgcatca  11100
gctaagctcc gcgtccttta ccaaggaaat aatgttactg tatctgctta tgcaaacggc  11160
gatcatgccg tcacagttaa ggacgctaaa ttcattgtgg ggccaatgtc ttcagcctgg  11220
acaccttttg acaataaaat cgtggtgtac aaaggcgacg tctacaacat ggactacccg  11280
cccttcggcg caggaagacc aggacaattt ggcgacatcc aaagtcgcac gcctgagagc  11340
gaagacgtct atgctaacac acaactggta ctgcagagac cgtccgcggg tacggtgcac  11400
gtgccgtact ctcaggcacc atctggcttc aagtattggc taaaagaacg aggggcgtcg  11460
ctgcagcaca cagcaccatt tggctgtcaa atagcaacaa acccggtaag agcgatgaac  11520
tgcgccgtag ggaacatgcc tatctccatc gacataccgg acgcggcctt cactagggtc  11580
gtcgacgcgc catctttaac ggacatgtcg tgtgaggtac cagcctgcac ccactcctca  11640
gactttgggg gcgtagccat cattaaatat gcagccagca agaaaggcaa gtgtgcggtg  11700
```

cattcgatga ctaacgccgt cactattcgg gaagctgaaa tagaagtaga agggaactct 11760
cagttgcaaa tctcttttc gacggcccta gccagcgccg aattccgcgt acaagtctgt 11820
tctacacaag tacactgtgc agccgagtgc catccaccga aagaccatat agtcaattac 11880
ccggcgtcac acaccaccct cggggtccaa gacatttccg ttacggcgat gtcatgggtg 11940
cagaagatca cgggaggtgt gggactggtt gtcgctgttg cagcactgat cctaatcgtg 12000
gtgctatgcg tgtcgtttag caggcactaa cttgacaact aggtacgaag gtatatgtgt 12060
cccctaagag acacaccaca tatagctaag aatcaataga taagtataga tcaaagggct 12120
gaacaacccc tgaatagtaa caaaatataa aaatcaacaa aaatcataaa atagaaaacc 12180
agaaacagaa gtaggtaaga aggtatatgt gtcccctaag agacacacca tatatagcta 12240
agaatcaata gataagtata gatcaaaggg ctgaataacc cctgaataat aacaaaatat 12300
aaaaatcaat aaaaatcata aaatagaaaa ccataaacag aagtagttca aagggctata 12360 aaaccccctga atagtaacaa aacataaaac taataaaaat caaatgaata ccataattgg 12420
caatcggaag agatgtaggt acttaagctt cctaaaagca gccgaactcg ctttgagatg 12480
taggcgtagc acaccgaact cttccataat tctccgaacc cacagggacg taggagatgt 12540
tcaaagtggc tataaaaccc tgaacagtaa taaaacataa aattaataag gatcaaatga 12600
gtaccataat tggcaaacgg aagagatgta ggtacttaag cttcctaaaa gcagccgaac 12660
tcactttgag atgtaggcat agcataccga actcttccac aattctccgt acccataggg 12720
acgtaggaga tgttattttg tttttaatat ttcaaaaaaa aaaaaaaaaa aaaagggtac 12780
gcggccgcca ctgtgctgga tatctgcaga attccaccac actggactag tggatcagct 12840
taagtttaaa ccgctgatca gcctcgactg tgccttctag ttgccagcca tctgttgttt 12900
gcccctcccc cgtgccttcc ttgaccctgg aaggtgccac tcccactgtc ctttcctaat 12960
aaaatgagga aattgcatcg cattgtctga gtaggtgtca ttctattctg gggggtgggg 13020
tggggcagga c 13031

<210> SEQ ID NO 4
<211> LENGTH: 13163
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
ggcgcgcctg acattgatta ttgactagtt attaatagta atcaattacg gggtcattag 60
ttcatagccc atatatggag ttccgcgtta cataacttac ggtaaatggc ccgcctggct 120
gaccgcccaa cgacccccgc ccattgacgt caataatgac gtatgttccc atagtaacgc 180
caatagggac tttccattga cgtcaatggg tggagtattt acggtaaact gcccacttgg 240
cagtacatca agtgtatcat atgccaagta cgccccctat tgacgtcaat gacggtaaat 300
ggcccgcctg gcattatgcc cagtacatga ccttatggga ctttcctact tggcagtaca 360
tctacgtatt agtcatcgct attaccatgg tgatgcggtt ttggcagtac atcaatgggc 420
gtggatagcg gtttgactca cggggatttc caagtctcca ccccattgac gtcaatggga 480
gtttgttttg gcaccaaaat caacgggact ttccaaaatg tcgtaacaac tccgccccat 540
tgacgcaaat gggcggtagg cgtgtacggt gggaggtcta tataagcaga gctctctggc 600
taactagaga tggctgcgtg agacacacgt agcctaccag tttcttactg ctctactctg 660

```
caaagcaaga gattaataac ccatcatgga ttctgtgtac gtggacatag acgctgacag    720
cgccttttg aaggccctgc aacgtgcgta ccccatgttt gaggtggaac ctaggcaggt    780
cacatcgaat gaccatgcta atgctagagc gttctcgcat ctagccataa aactaataga    840
gcaggaaatt gatcccgact caaccatcct ggatataggt agtgcgccag caaggaggat    900
gatgtcggac aggaagtacc actgcgtttg cccgatgcgc agcgcagaag atcccgagag    960
actcgctaat tatgcgagaa agctcgcatc tgccgcagga aaagtcctgg acagaaacat   1020
ttctggaaag atcggggact tacaagcggt gatggccgtg ccagacacgg agacgccaac   1080
attttgctta cacacagatg tctcatgtag acagagagca gacgtcgcga tataccaaga   1140
cgtctatgct gtacacgcac ccacgtcgct ataccaccag gcgattaaag gagtccgagt   1200
ggcgtactgg gtagggttcg acacaacccc gttcatgtac aacgctatgg cgggtgccta   1260
cccctcatac tcgacaaatt gggcggatga gcaggtactg aaggctaaga acataggatt   1320
atgttcaaca gacctgacgg aaggtagacg aggcaaattg tctatcatga gagggaaaaa   1380
gctaaaaccg tgcgaccgtg tgctgttctc agtagggtca acgctttacc cggaaagccg   1440
cacgctactt aagagctggc acctaccatc ggtgttccat ctaaagggca agcttagctt   1500
cacatgccgc tgtgacacag tggtttcgtg tgagggctac gtcgttaaga gaataacgat   1560
gagcccaggc ctttatggaa aaaccatagg gtatgcggta acccaccacg cagacggatt   1620
cttgatgtgc aagactaccg acacggttga cggcgaaaga gtgtcattct cggtgtgcac   1680
gtacgtgccg gcgaccattt gtgatcaaat gaccggcatc cttgctacag aagtcacgcc   1740
ggaggatgca cagaagctgt tggtggggct gaaccagagg atagtggtta acggcagaac   1800
gcaacggaac acgaacacca tgaagaacta cctacttccc gtggtcgccc aggccttcag   1860
taagtgggca aaggagtgcc ggaaggacat ggaagatgag aagcttctgg gggtcagaga   1920
aagaacacta acctgctgct gtctatgggc atttaagaag cagaaaacac acacggtcta   1980
caagaggcct gatacccagt caatccagaa ggttcaggcc gaatttgaca gctttgtagt   2040
accgggcctg tggtcgtccg ggttgtcaat cccgttgagg actagaatca agtggttgtt   2100
acgcaaggtg ccgaaaacag acctgatccc atacagcggg aatgcccaag aagcccagga   2160
tgcagaaaaa gaagcagagg aagaacgaga agcagaactg actcatgagg ctctaccacc   2220
cctacaggca gcacaggaag atgtccaggt cgaaatcgac gtggaacagc ttgaggatag   2280
agctggtgct ggaataatag agactccgag aggcgctatc aaagttactg cccaactaac   2340
agaccacgtc gtgggggagt acctggtact ttccccgcag accgtactac gcagccagaa   2400
gctcagcctg atccacgctt tagcggagca agtgaagacg tgtacgcaca gcggacgagc   2460
agggaggtat gcggtcgaag cgtacgatgg ccgagtccta gtgccctcag gctatgcaat   2520
ttcgcctgaa gacttccaga gtctaagcga aagcgcaacg atggtgtaca acgaaagaga   2580
gttcgtaaac agaaagttac accacattgc gatgcacgga ccagccctga acactgacga   2640
agagtcgtat gagctggtga gggcagagag gacagaacac gagtacgtct acgacgtgga   2700
ccagagaaga tgctgtaaga aggaagaagc tgcaggactg gtactggtgg gcgacttgac   2760
taatccgccc taccacgaat tcgcatacga agggctaaaa attcgccccg cctgcccata   2820
caaaattgca gtcataggag tcttcggggt accaggatct ggcaagtcag ccattatcaa   2880
gaacctagtt accaggcaag acctggtgac tagcggaaag aaagaaaact gccaagaaat   2940
cagcaccgac gtgatgagac agagaggtct agagatatct gcacgtacgg tagattcgct   3000
gctcttgaat ggatgcaaca gaccagtcga cgtgttgtac gtagacgagg cgtttgcgtg   3060
```

```
ccactctgga acgttacttg ctttgatcgc cttggtgaga ccaagacaga aagttgtact   3120
ttgtggtgac ccgaagcagt gcggcttctt caatatgatg cagatgaaag tcaactacaa   3180
tcataacatc tgcacccaag tgtaccacaa aagtatctcc aggcggtgta cactgcctgt   3240
gactgccatt gtgtcatcgt tgcattacga aggcaaaatg cgcactacga atgagtacaa   3300
catgccgatt gtagtggaca ctacaggctc aacgaaacct gaccctggag acctcgtgtt   3360
aacgtgcttc agagggtggg ttaaacaact gcaaattgac tatcgtggac acgaggtcat   3420
gacagcagcc gcatcccaag ggttaactag aaaaggagtt tacgcagtta ggcaaaaagt   3480
taacgaaaac ccactctatg catcaacatc agagcacgtc aacgtactcc taacgcgtac   3540
ggaaggtaaa ctggtatgga agacactctc tggtgacccg tggataaaga cgctgcagaa   3600
cccaccgaaa ggaaacttca aagcaactat taaggagtgg gaggtggagc acgcatcgat   3660
aatggcgggc atctgcagtc accaagtgac ctttgacaca ttccaaaaca aagccaacgt   3720
ttgctgggct aagagcttgg tccctatcct cgaaacagcg gggataaaac taaatgatag   3780
gcagtggtcc cagataattc aagccttcaa agaagacaaa gcatactcac ccgaagtagc   3840
cctgaatgaa atatgcacgc gcatgtatgg ggtggatcta gacagtgggc tattctctaa   3900
accgttggta tctgtgtatt acgcggataa ccattgggat aataggccgg gaggaaagat   3960
gttcggattc aaccctgagg cagcgtccat tctagaaaga aagtacccat ttacaaaagg   4020
aaagtggaac atcaacaagc agatctgcgt gactaccagg aggatagaag acttcaaccc   4080
taccaccaac attataccgg tcaacaggag actaccacac tcattagtgg ccgaacaccg   4140
cccagtaaaa ggggaaagaa tggaatggct ggttaacaag ataaacggac accacgtact   4200
cctggttagc ggctataacc ttgcactgcc tactaagaga gtcacctggg tagcgccact   4260
aggtgtccgc ggagcggact atacatacaa cctagagctg ggtctaccag caacrcttgg   4320
taggtatgac ctagtggtca taaacatcca cacacctttt cgcatacacc attaccaaca   4380
gtgcgtagat cacgcaatga aactgcaaat gctagggggt gactcactga gactgctcaa   4440
accgggtggc tctctattga tcagagcata cggttacgca gatagaacca gtgaacgagt   4500
catctgcgta ctgggacgca agtttagatc gtctagagca ttgaaaccac catgtgtcac   4560
cagtaatact gagatgtttt tcctatttag caattttgac aatggcagaa ggaattttac   4620
aacgcatgtc atgaacaatc aactgaatgc agcctttgta ggacaggcca cccgagcagg   4680
atgtgcacca tcgtaccggg taaaacgcat ggacatcgcg aagaacgatg aagagtgcgt   4740
ggttaacgcc gccaaccctc gcgggttacc aggtgacggt gtttgcaagg cagtatataa   4800
aaagtggccg gagtccttta aaaacagtgc aacaccagta ggaaccgcaa aaacagttat   4860
gtgcggtacg tatccagtaa tccacgccgt aggaccaaac ttctcaaatt attcggagtc   4920
tgaaggggac cgggaattgg cggctgccta tcgagaagtc gcaaaggaag taactagact   4980
gggagtaaat agcgtagcta tacctctcct ctccacaggt gtatactcag gagggaaaga   5040
caggctaacc cagtcactga accacctctt tacagccatg gactcgacgg atgcagacgt   5100
ggtcatctac tgccgagaca aggaatggga gaagaaaata tctgaggcca tacagatgcg   5160
gacccaagtg gagctgctgg atgagcacat ctccatagac tgcgatgtca ttcgcgtgca   5220
ccctgacagt agcttggcag gcagaaaagg atacagcacc acggaaggcg cactgtattc   5280
atatctagaa gggacacgtt ttcaccagac ggcagtggat atggcagaga tatacactat   5340
gtggccaaag caaacagagg ccaatgagca agtctgccta tatgccctgg gggaaagtat   5400
```

-continued

```
tgaatcaatc aggcagaaat gcccggtgga tgatgcagac gcatcatctc ccccgaaaac   5460
tgtcccgtgt ctttgccggt atgccatgac tcctgaacgc gtcacccgac ttcgcatgaa   5520
ccatgtcaca aatataattg tgtgttcttc atttcccctt ccaaagtaca agatagaagg   5580
agtgcaaaaa gtcaaatgct ccaaggtaat gttattcgat cacaatgtgc catcgcgcgt   5640
aagtccaagg gaatacagat cttcccagga gtctgtacag gaagtgagta cgacaacgtc   5700
attgacgcat agccagtttg atctaagcgc cgatggcgag acactgcctg tcccgtcaga   5760
cctggatgct gacgccccag ccctagaacc ggccctagac gacggggcgg tacatacatt   5820
accaaccata atcggaaacc ttgcggccgt gtctgactgg gtaatgagca ccgtacctgt   5880
cgcgccgcct agaagaagga gagggagaaa cctgactgtg acatgtgacg agagagaagg   5940
gaatataaca cccatggcta gcgtccgatt ctttagagca gagctgtgtc cggccgtaca   6000
agaaacagcg gagacgcgtg acacagctat ttcccttcag gcaccgccaa gtaccaccat   6060
ggaactgagc catccaccga tctccttcgg agcaccaagc gagacgttcc ccatcacatt   6120
tggggacttc gacgaaggag aaatcgaaag cttgtcttct gagctactaa ctttcggaga   6180
cttcctaccc ggtgaagtgg atgatctgac agatagcgac tggtccacgt gcccagacac   6240
ggacgacgag ttatgactag acagggcagg tgggtatata ttctcgtcgg acactggtcc   6300
aggccattta caacagaagt cggtacgcca gtcagtgctg ccggtaaaca ccctggagga   6360
agtccacgag gagaagtgtt acccacctaa gctggatgaa ttaaaggagc aactactact   6420
taagaaactc caggagagtg cgtccatggc caatagaagc aggtatcagt cacgcaaagt   6480
ggaaaatatg aaagcaacaa tcatccagag actaaagaga ggctgtaaac tgtatttaat   6540
ggcagagacc ccgaaagtcc cgacttatcg gaccatatac ccggcgcctg tgtactcgcc   6600
tccgatcaat gtccgattgt ccaaccccga gtccgcagtg gcagcatgta atgagttctt   6660
agctagaaac tacccaactg tttcatcata ccaaatcacc gacgagtatg atgcatatct   6720
agacatggtg gacgggtcgg agagttgctt ggaccgagcg acattcaatc cgtcaaaact   6780
taggagctac ccgaaacaac atgcttatca cgcgccttct atcagaagcg ctgtaccttc   6840
cccattccag aacacactac agaatgtact ggcagcagcc acgaaaagga actgcaacgt   6900
cacacagatg agggaattac ccactttgga ctcagcagta ttcaacgtgg agtgttttaa   6960
aaaattcgca tgtaaccgag aatactggga agaatttgca gccagcccta tcaggataac   7020
aactgagaat ctaacaacct atgtcactaa actaaagggg ccaaaagcag cagcgctgtt   7080
tgcaaaaacc cataatctgc tgccactgca ggatgtacca atggataggt tcacagtaga   7140
tatgaaaagg gatgtgaagg taactcctgg tacaaagcat acagaggaaa gacctaaggt   7200
gcaggttata caggcggctg aacccttggc aacagcgtac ctatgtggaa ttcacagaga   7260
actggttagg agattgaacg ccgtcctcct acccaatgtg catacactat ttgacatgtc   7320
tgccgaggac ttcgatgcca ttatagccgc acacttcaag ccaggagacg ctgttttaga   7380
aacggacata gcctcctttg ataagagcca agatgattca cttgcgctta ccgccttaat   7440
gctgttagaa gatttgggag tggatcactc cctgttggac ttgatagagg ctgctttcgg   7500
agagatttcc agctgtcatc tgccgacagg tacgcgcttc aagttcggcg ctatgatgaa   7560
atccggtatg ttcctaactc tgttcgtcaa cacgttgtta aatatcacca tcgctagccg   7620
ggtgttggaa gatcgtctga caaaatccgc atgcgcggcc ttcatcggcg acgacaacat   7680
aatacatggt gtcgtctccg atgaattgat ggcagccaga tgcgctactt ggatgaacat   7740
ggaagtgaag atcatagatg cagttgtatc ccagaaagct ccttactttt gtggagggtt   7800
```

-continued

```
tatactgcat gatactgtga caggaacagc ttgcagagtg gcggacccgc taaaaaggtt   7860
atttaaattg ggcaaaccgt tagcggcagg tgacgaacaa gatgaagaca gaagacgggc   7920
gctggctgat gaagtaatca gatggcaacg aacagggcta atagatgagc tggagaaagc   7980
ggtgtactct aggtacgaag tgcagggtat atcagttgcg gtaatgtcca tggccacctt   8040
tgcaagctcc agatccaact tcgagaagct cagaggaccc gtcataactt tgtacggcgg   8100
tcctaaatag gtacgcacta cagctaccta ttttgcagaa gccgacagca ggtacctaaa   8160
taccaatcag ccataatgga gtttatccca acccaaactt tctacaatag gaggtaccag   8220
cctcgacctt ggactccgcg ccctactatc caagttatca gacccagacc gcgtccgcaa   8280
aggaaagccg ggcaacttgc ccagctgatc tcagcagtta ataaactgac aatgcgcgcg   8340
gtacctcaac agaagccgcg caagaatcgg aagaataaga agcaaaagca aaagcagcag   8400
gcgccacgaa acaacatgaa tcaaaagaag cagcccccta aaaagaaacc ggctcaaaag   8460
aaaaagaagc cgggccgtag agagagaatg tgcatgaaaa tcgaaaatga ttgcatcttc   8520
gaagtcaagc atgaaggtaa ggtaacaggt tacgcgtgct tggtagggga caaagtaatg   8580
aagccagcac acgtaaaggg gaccatcgat aatgcggacc tggccaaatt ggccttcaag   8640
cggtcatcta agtacgacct tgaatgcgcg cagataccog tgcacatgaa gtccgacgct   8700
tcgaagttca cccatgagaa accggagggg tactacaact ggcaccacgg agcagtacag   8760
tactcaggag gccggttcac catccctaca ggtgcgggca aaccagggga cagcggtaga   8820
ccgatcttcg acaacaaggg gcgcgtggtg gccatagttt taggaggagc taatgaagga   8880
gcccgtacag ccctctcggt ggtgacctgg aacaaagaca tcgtcacgaa aatcacccct   8940
gagggggccg aagagtggag tcttgccatt ccagttatgt gcctgctggc aaataccacg   9000
ttcccctgct cccagccccc ttgcacaccc tgctgctacg aaaaagagcc ggagaaaacc   9060
ctgcgcatgc tagaagacaa cgtcatgagc ccccgggtact atcagctgct acaagcatcc   9120
ttaacatgtt ctccccgccg ccagcgacgc agtattaagg acaacttcaa tgtctataaa   9180
gccataagac cgtacctagc tcactgtccc gactgtggag aagggcactc gtgccatagt   9240
cccgtagcgc tagaacgcat cagaaacgaa gcgacagacg ggacgctgaa aatccaggtt   9300
tccttgcaaa tcggaataaa gacggatgat agccatgatt ggaccaagct gcgttacatg   9360
gacaatcata tgccagcaga cgcagagagg gccaggctat ttgtaagaac gtcagcaccg   9420
tgcacgatta ctggaacaat gggacacttc atcctggccc gatgtccgaa aggagaaact   9480
ctgacggtgg gattcactga cggtaggaag atcagtcact catgtacgca cccatttcac   9540
cacgaccctc ctgtgatagg ccgggaaaaa tttcattccc gaccgcagca cggtagagaa   9600
ctaccttgca gcacgtacgc gcagagcacc gctgcaactg ccgaggagat agaggtacat   9660
atgcccccag acaccccaga tcgcacattg atgtcacaac agtccggtaa tgtaaagatc   9720
acagtcaata gtcagacggt gcggtacaag tgtaattgcg gtgactcaaa tgaaggacta   9780
accactacag acaaagtgat taataactgc aaggttgatc aatgccatgc cgcggtcacc   9840
aatcacaaaa aatggcagta taattcccct ctggtcccgc gtaatgctga actcggggac   9900
cgaaaaggaa aagttcacat tccgtttcct ctggcaaatg tgacatgcag ggtgcctaag   9960
gcaaggaacc ccaccgtgac gtacggaaaa aaccaagtca tcatgctgct gtatcctgac  10020
cacccaacgc tcctgtccta ccggaatatg ggagaagaac caaactatca agaagagtgg  10080
gtgacgcata agaaggagat caggttaacc gtgccgactg aagggctcga ggtcacgtgg  10140
```

-continued

```
ggcaacaacg agccgtacaa gtattggccg cagttatcca caaacggtac agcccacggc  10200
cacccgcatg agataatttt gtattattat gagctgtacc ctactatgac tgtggtagtt  10260
gtgtcagtgg cctcgttcgt actcctgtcg atggtgggtg tggcagtggg gatgtgcatg  10320
tgtgcacgac gcagatgcat tacaccgtac gaactgacac caggagctac cgtccctttc  10380
ctgcttagcc taatatgctg cattagaaca gctaaagcgg ccacatacca agaggctgcg  10440
gtatacctgt ggaacgagca gcagcctttg ttttggctgc aagcccttat tccgctggca  10500
gccctgattg tcctatgcaa ctgtctgaga ctcttaccat gcttttgtaa aacgttgact  10560
tttttagccg taatgagcgt cggtgcccac actgtgagcg cgtacgaaca cgtaacagtg  10620
atcccgaaca cggtgggagt accgtataag actctagtca acagaccggg ctacagcccc  10680
atggtactgg agatggagct tctgtcagtc actttggagc caacgctatc gcttgattac  10740
atcacgtgcg agtataaaac cgtcatcccg tctccgtacg tgaaatgctg cggtacagca  10800
gagtgcaagg acaagagcct acctgattac agctgtaagg tcttcaccgg cgtctaccca  10860
ttcatgtggg gcggcgccta ctgcttctgc gacactgaaa atacgcaatt gagcgaagca  10920
catgtggaga agtccgaatc atgcaaaaca gaatttgcat cagcatatag ggctcatacc  10980
gcatccgcat cagctaagct ccgcgtcctt taccaaggaa ataatgttac tgtatctgct  11040
tatgcaaacg gcgatcatgc cgtcacagtt aaggacgcta aattcattgt ggggccaatg  11100
tcttcagcct ggacaccttt tgacaataaa atcgtggtgt acaaaggcga cgtctacaac  11160
atggactacc cgcccttcgg cgcaggaaga ccaggacaat ttggcgacat ccaaagtcgc  11220
acgcctgaga gcgaagacgt ctatgctaac acacaactgg tactgcagag accgtccgcg  11280
ggtacggtgc acgtgccgta ctctcaggca ccatctggct tcaagtattg gctaaaagaa  11340
cgaggggcgt cgctgcagca cacagcacca tttggctgtc aaatagcaac aaacccggta  11400
agagcgatga actgcgccgt agggaacatg cctatctcca tcgacatacc ggacgcggcc  11460
ttcactaggg tcgtcgacgc gccatcttta acggacatgt cgtgtgaggt accagcctgc  11520
acccactcct cagactttgg gggcgtagcc atcattaaat atgcagccag caagaaaggc  11580
aagtgtgcgg tgcattcgat gactaacgcc gtcactattc gggaagctga aatagaagta  11640
gaagggaact ctcagttgca aatctctttt tcgacggccc tagccagcgc cgaattccgc  11700
gtacaagtct gttctacaca agtacactgt gcagccgagt gccatccacc gaaagaccat  11760
atagtcaatt acccggcgtc acacaccacc ctcggggtcc aagacatttc cgttacggcg  11820
atgtcatggg tgcagaagat cacgggaggt gtgggactgg ttgtcgctgt tgcagcactg  11880
atcctaatcg tggtgctatg cgtgtcgttt agcaggcact aacttgacaa ctaggtacga  11940
aggtatatgt gtcccctaag agacacacca catatagcta agaatcaata gataagtata  12000
gatcaaaggg ctgaacaacc cctgaatagt aacaaaatat aaaaatcaac aaaaatcata  12060
aaatagaaaa ccagaaacag aagtaggtaa gaaggtatat gtgtccccta agagacacac  12120
catatatagc taagaatcaa tagataagta tagatcaaag ggctgaataa cccctgaata  12180
ataacaaaat ataaaaatca ataaaaatca taaaatagaa aaccataaac agaagtagtt  12240
caaagggcta taaaacccct gaatagtaac aaaacataaa actaataaaa atcaaatgaa  12300
taccataatt ggcaatcgga agagatgtag gtacttaagc ttcctaaaag cagccgaact  12360
cgctttgaga tgtaggcgta gcacaccgaa ctcttccata attctccgaa cccacaggga  12420
cgtaggagat gttcaaagtg gctataaaac cctgaacagt aataaaacat aaaattaata  12480
aggatcaaat gagtaccata attggcaaac ggaagagatg taggtactta agcttcctaa  12540
```

-continued

```
aagcagccga actcactttg agatgtaggc atagcatacc gaactcttcc acaattctcc  12600

gtacccatag ggacgtagga gatgttattt tgtttttaat atttcgagag agttgcaagg  12660

ctaagcactg caatggaaag gctctgcggc atatatgagc ctattctagg gagacatgtc  12720

atctttcatg aaggttcagt gtcctagttc ccttccccca ggcaaaacga cacgggagca  12780

ggtcagggtt gctctgggta aaagcctgta agcctaagag ctaatcctgt acatggctcc  12840

tttacctaca cactggggat ttgacctcta tctccactct cattaaaaaa aaaaaaaaaa  12900

aaaaaagggt acgcggccgc cactgtgctg gatatctgca gaattccacc acactggact  12960

agtggatcag cttaagttta aaccgctgat cagcctcgac tgtgccttct agttgccagc  13020

catctgttgt ttgcccctcc cccgtgcctt ccttgaccct ggaaggtgcc actcccactg  13080

tcctttccta ataaaatgag gaaattgcat cgcattgtct gagtaggtgt cattctattc  13140

tggggggtgg ggtggggcag gac                                          13163
```

```
<210> SEQ ID NO 5
<211> LENGTH: 12173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

```
ggcgcgcctg acattgatta ttgactagtt attaatagta atcaattacg gggtcattag     60

ttcatagccc atatatggag ttccgcgtta cataacttac ggtaaatggc ccgcctggct    120

gaccgcccaa cgacccccgc ccattgacgt caataatgac gtatgttccc atagtaacgc    180

caatagggac tttccattga cgtcaatggg tggagtattt acggtaaact gcccacttgg    240

cagtacatca agtgtatcat atgccaagta cgccccctat tgacgtcaat gacggtaaat    300

ggcccgcctg gcattatgcc cagtacatga ccttatggga ctttcctact tggcagtaca    360

tctacgtatt agtcatcgct attaccatgg tgatgcggtt ttggcagtac atcaatgggc    420

gtggatagcg gtttgactca cggggatttc caagtctcca ccccattgac gtcaatggga    480

gtttgttttg gcaccaaaat caacgggact ttccaaaatg tcgtaacaac tccgccccat    540

tgacgcaaat gggcggtagg cgtgtacggt gggaggtcta tataagcaga gctctctggc    600

taactagaga taggcggcgc atgagagaag cccagaccaa ttacctaccc aaaatggaga    660

aagttcacgt tgacatcgag gaagacagcc cattcctcag agctttgcag cggagcttcc    720

cgcagtttga ggtagaagcc aagcaggtca ctgataatga ccatgctaat gccagagcgt    780

tttcgcatct ggcttcaaaa ctgatcgaaa cggaggtgga cccatccgac acgatccttg    840

acattggaag tgcgcccgcc cgcagaatgt attctaagca caagtatcat tgtatctgtc    900

cgatgagatg tgcggaagat ccggacagat tgtataagta tgcaactaag ctgaagaaaa    960

actgtaagga aataactgat aaggaattgg acaagaaaat gaaggagctc gccgccgtca   1020

tgagcgaccc tgacctggaa actgagacta tgtgcctcca cgacgacgag tcgtgtcgct   1080

acgaagggca agtcgctgtt taccaggatg tatacgcggt tgacggaccg acaagtctct   1140

atcaccaagc caataaggga gttagagtcg cctactggat aggctttgac accacccctt   1200

ttatgtttaa gaacttggct ggagcatatc catcatactc taccaactgg gccgacgaaa   1260

ccgtgttaac ggctcgtaac ataggcctat gcagctctga cgttatggag cggtcacgta   1320

gagggatgtc cattcttaga aagaagtatt tgaaaccatc caacaatgtt ctattctctg   1380
```

ttggctcgac catctaccac gagaagaggg acttactgag gagctggcac ctgccgtctg 1440
tatttcactt acgtggcaag caaaattaca catgtcggtg tgagactata gttagttgcg 1500
acgggtacgt cgttaaaaga atagctatca gtccaggcct gtatgggaag ccttcaggct 1560
atgctgctac gatgcaccgc gagggattct tgtgctgcaa agtgacagac acattgaacg 1620
gggagagggt ctcttttccc gtgtgcacgt atgtgccagc tacattgtgt gaccaaatga 1680
ctggcatact ggcaacagat gtcagtgcgg acgacgcgca aaaactgctg gttgggctca 1740
accagcgtat agtcgtcaac ggtcgcaccc agagaaacac caataccatg aaaaattacc 1800
ttttgcccgt agtggcccag gcatttgcta ggtgggcaaa ggaatataag gaagatcaag 1860
aagatgaaag gccactagga ctacgagata gacagttagt catggggtgt tgttgggctt 1920
ttagaaggca caagataaca tctatttata agcgcccgga tacccaaacc atcatcaaag 1980
tgaacagcga tttccactca ttcgtgctgc ccaggatagg cagtaacaca ttggagatcg 2040
ggctgagaac aagaatcagg aaaatgttag aggagcacaa ggagccgtca cctctcatta 2100
ccgccgagga cgtacaagaa gctaagtgcg cagccgatga ggctaaggag gtgcgtgaag 2160
ccgaggagtt gcgcgcagct ctaccacctt tggcagctga tgttgaggag cccactctgg 2220
aagccgatgt cgacttgatg ttacaagagg ctggggccgg ctcagtggag acacctcgtg 2280
gcttgataaa ggttaccagc tacgctggcg aggacaagat cggctcttac gctgtgcttt 2340
ctccgcaggc tgtactcaag agtgaaaaat tatcttgcat ccaccctctc gctgaacaag 2400
tcatagtgat aacacactct ggccgaaaag ggcgttatgc cgtggaacca taccatggta 2460
aagtagtggt gccagaggga catgcaatac ccgtccagga ctttcaagct ctgagtgaaa 2520
gtgccaccat tgtgtacaac gaacgtgagt tcgtaaacag gtacctgcac catattgcca 2580
cacatggagg agcgctgaac actgatgaag aatattacaa aactgtcaag cccagcgagc 2640
acgacggcga atacctgtac gacatcgaca ggaaacagtg cgtcaagaaa gaactagtca 2700
ctgggctagg gctcacaggc gagctggtgg atcctccctt ccatgaattc gcctacgaga 2760
gtctgagaac acgaccagcc gctccttacc aagtaccaac cataggggtg tatggcgtgc 2820
caggatcagg caagtctggc atcattaaaa gcgcagtcac caaaaaagat ctagtggtga 2880
gcgccaagaa agaaaactgt gcagaaatta taagggacgt caagaaaatg aaagggctgg 2940
acgtcaatgc cagaactgtg gactcagtgc tcttgaatgg atgcaaacac cccgtagaga 3000
ccctgtatat tgacgaagct tttgcttgtc atgcaggtac tctcagagcg ctcatagcca 3060
ttataagacc taaaaaggca gtgctctgcg gggatcccaa acagtgcggt ttttttaaca 3120
tgatgtgcct gaaagtgcat tttaaccacg agatttgcac acaagtcttc cacaaaagca 3180
tctctcgccg ttgcactaaa tctgtgactt cggtcgtctc aaccttgttt tacgacaaaa 3240
aaatgagaac gacgaatccg aaagagacta agattgtgat tgacactacc ggcagtacca 3300
aacctaagca ggacgatctc attctcactt gtttcagagg gtgggtgaag cagttgcaaa 3360
tagattacaa aggcaacgaa ataatgacgg cagctgcctc tcaagggctg acccgtaaag 3420
gtgtgtatgc cgttcggtac aaggtgaatg aaaatcctct gtacgcaccc acctcagaac 3480
atgtgaacgt cctactgacc cgcacggagg accgcatcgt gtggaaaaca ctagccggcg 3540
acccatggat aaaaacactg actgccaagt accctgggaa tttcactgcc acgatagagg 3600
agtggcaagc agagcatgat gccatcatga ggcacatctt ggagagaccg gaccctaccg 3660
acgtcttcca gaataaggca aacgtgtgtt gggccaaggc tttagtgccg gtgctgaaga 3720

-continued

```
ccgctggcat agacatgacc actgaacaat ggaacactgt ggattatttt gaaacggaca   3780
aagctcactc agcagagata gtattgaacc aactatgcgt gaggttcttt ggactcgatc   3840
tggactccgg tctattttct gcacccactg ttccgttatc cattaggaat aatcactggg   3900
ataactcccc gtcgcctaac atgtacgggc tgaataaaga agtggtccgt cagctctctc   3960
gcaggtaccc acaactgcct cgggcagttg ccactggaag agtctatgac atgaacactg   4020
gtacactgcg caattatgat ccgcgcataa acctagtacc tgtaaacaga agactgcctc   4080
atgctttagt cctccaccat aatgaacacc cacagagtga cttttcttca ttcgtcagca   4140
aattgaaggg cagaactgtc ctggtggtcg gggaaaagtt gtccgtccca ggcaaaatgg   4200
ttgactggtt gtcagaccgg cctgaggcta ccttcagagc tcggctggat ttaggcatcc   4260
caggtgatgt gcccaaatat gacataatat ttgttaatgt gaggacccca tataaatacc   4320
atcactatca gcagtgtgaa gaccatgcca ttaagcttag catgttgacc aagaaagctt   4380
gtctgcatct gaatcccggc ggaacctgtg tcagcatagg ttatggttac gctgacaggg   4440
ccagcgaaag catcattggt gctatagcgc ggcagttcaa gttttcccgg gtatgcaaac   4500
cgaaatcctc acttgaagag acggaagttc tgtttgtatt cattgggtac gatcgcaagg   4560
cccgtacgca caatccttac aagctttcat caaccttgac caacatttat acaggttcca   4620
gactccacga agccggatgt gcaccctcat atcatgtggt gcgaggggat attgccacgg   4680
ccaccgaagg agtgattata aatgctgcta acagcaaagg acaacctggc ggaggggtgt   4740
gcggagcgct gtataagaag ttcccggaaa gcttcgattt acagccgatc gaagtaggaa   4800
aagcgcgact ggtcaaaggt gcagctaaac atatcattca tgccgtagga ccaaacttca   4860
acaaagtttc ggaggttgaa ggtgacaaac agttggcaga ggcttatgag tccatcgcta   4920
agattgtcaa cgataacaat tacaagtcag tagcgattcc actgttgtcc accggcatct   4980
tttccgggaa caaagatcga ctaacccaat cattgaacca tttgctgaca gctttagaca   5040
ccactgatgc agatgtagcc atatactgca gggacaagaa atgggaaatg actctcaagg   5100
aagcagtggc taggagagaa gcagtggagg agatatgcat atccgacgac tcttcagtga   5160
cagaacctga tgcagagctg gtgagggtgc atccgaagag ttctttggct ggaaggaagg   5220
gctacagcac aagcgatggc aaaactttct catatttgga agggaccaag tttcaccagg   5280
cggccaagga tatagcagaa attaatgcca tgtggcccgt tgcaacggag gccaatgagc   5340
aggtatgcat gtatatcctc ggagaaagca tgagcagtat taggtcgaaa tgccccgtcg   5400
aagagtcgga agcctccaca ccacctagca cgctgccttg cttgtgcatc catgccatga   5460
ctccagaaag agtacagcgc ctaaaagcct cacgtccaga acaaattact gtgtgctcat   5520
cctttccatt gccgaagtat agaatcactg gtgtgcagaa gatccaatgc tcccagccta   5580
tattgttctc accgaaagtg cctgcgtata ttcatccaag gaagtatctc gtggaaacac   5640
caccggtaga cgagactccg gagccatcgg cagagaacca atccacagag gggacacctg   5700
aacaaccacc acttataacc gaggatgaga ccaggactag aacgcctgag ccgatcatca   5760
tcgaagagga agaagaggat agcataagtt tgctgtcaga tggcccgacc caccaggtgc   5820
tgcaagtcga ggcagacatt cacgggccgc cctctgtatc tagctcatcc tggtccattc   5880
ctcatgcatc cgactttgat gtggacagtt tatccatact tgacaccctg gagggagcta   5940
gcgtgaccag cggggcaacg tcagccgaga ctaactctta cttcgcaaag agtatggagt   6000
ttctggcgcg accggtgcct gcgcctcgaa cagtattcag gaaccctcca catcccgctc   6060
cgcgcacaag aacaccgtca cttgcaccca gcagggcctg ctcgagaacc agcctagttt   6120
```

```
ccaccccgcc aggcgtgaat agggtgatca ctagagagga gctcgaggcg cttaccccgt   6180
cacgcactcc tagcaggtcg gtctcgagaa ccagcctggt ctccaacccg ccaggcgtaa   6240
atagggtgat tacaagagag gagtttgagg cgttcgtagc acaacaacaa tgacggtttg   6300
atgcgggtgc atacatcttt tcctccgaca ccggtcaagg gcatttacaa caaaaatcag   6360
taaggcaaac ggtgctatcc gaagtggtgt tggagaggac cgaattggag atttcgtatg   6420
ccccgcgcct cgaccaagaa aaagaagaat tactacgcaa gaaattacag ttaaatccca   6480
cacctgctaa cagaagcaga taccagtcca ggaaggtgga gaacatgaaa gccataacag   6540
ctagacgtat tctgcaaggc ctagggcatt atttgaaggc agaaggaaaa gtggagtgct   6600
accgaaccct gcatcctgtt cctttgtatt catctagtgt gaaccgtgcc ttctcaagcc   6660
ccaaggtcgc agtggaagcc tgtaacgcca tgttgaaaga gaactttccg actgtggctt   6720
cttactgtat tattccagag tacgatgcct atttggacat ggttgacgga gcttcatgct   6780
gcttagacac tgccagtttt tgccctgcaa agctgcgcag ctttccaaag aaacactcct   6840
atttggaacc cacaatacga tcggcagtgc cttcagcgat ccagaacacg ctccagaacg   6900
tcctggcagc tgccacaaaa agaaattgca atgtcacgca aatgagagaa ttgcccgtat   6960
tggattcggc ggcctttaat gtggaatgct tcaagaaata tgcgtgtaat aatgaatatt   7020
gggaaacgtt taaagaaaac cccatcaggc ttactgaaga aaacgtggta aattacatta   7080
ccaaattaaa aggaccaaaa gctgctgctc tttttgcgaa gacacataat ttgaatatgt   7140
tgcaggacat accaatggac aggtttgtaa tggacttaaa gagagacgtg aaagtgactc   7200
caggaacaaa acatactgaa gaacggccca aggtacaggt gatccaggct gccgatccgc   7260
tagcaacagc gtatctgtgc ggaatccacc gagagctggt taggagatta aatgcggtcc   7320
tgcttccgaa cattcataca ctgtttgata tgtcggctga agactttgac gctattatag   7380
ccgagcactt ccagcctggg gattgtgttc tggaaactga catcgcgtcg tttgataaaa   7440
gtgaggacga cgccatggct ctgaccgcgt taatgattct ggaagactta ggtgtggacg   7500
cagagctgtt gacgctgatt gaggcggctt tcggcgaaat ttcatcaata catttgccca   7560
ctaaaactaa atttaaattc ggagccatga tgaaatctgg aatgttcctc acactgtttg   7620
tgaacacagt cattaacatt gtaatcgcaa gcagagtgtt gagagaacgg ctaaccggat   7680
caccatgtgc agcattcatt ggagatgaca atatcgtgaa aggagtcaaa tcggacaaat   7740
taatggcaga caggtgcgcc acctggttga atatggaagt caagattata gatgctgtgg   7800
tgggcgagaa agcgccctat ttctgtggag ggtttatttt gtgtgactcc gtgaccggca   7860
cagcgtgccg tgtggcagac cccctaaaaa ggctgtttaa gcttggcaaa cctctggcag   7920
cagacgatga acatgatgat gacaggagaa gggcattgca tgaagagtca acacgctgga   7980
accgagtggg tattctttca gagctgtgca aggcagtaga atcaaggtat gaaaccgtag   8040
gaacttccat catagttatg gccatgacta ctctagctag cagtgttaaa tcattcagct   8100
acctgagagg ggcccctata actctctacg gctaacctga atggactacg acatagtcta   8160
gtccgccaag atggagttta tcccaaccca aactttctac aataggaggt accagcctcg   8220
accttggact ccgcgcccta ctatccaagt tatcagaccc agaccgcgtc cgcaaaggaa   8280
agccgggcaa cttgcccagc tgatctcagc agttaataaa ctgacaatgc gcgcggtacc   8340
tcaacagaag ccgcgcaaga atcggaagaa taagaagcaa aagcaaaagc agcaggcgcc   8400
acgaaacaac atgaatcaaa agaagcagcc ccctaaaaag aaaccggctc aaaagaaaaa   8460
```

-continued

```
gaagccgggc cgtagagaga gaatgtgcat gaaaatcgaa aatgattgca tcttcgaagt   8520
caagcatgaa ggtaaggtaa caggttacgc gtgcttggta ggggacaaag taatgaagcc   8580
agcacacgta aaggggacca tcgataatgc ggacctggcc aaattggcct tcaagcggtc   8640
atctaagtac gaccttgaat gcgcgcagat acccgtgcac atgaagtccg acgcttcgaa   8700
gttcacccat gagaaaccgg aggggtacta caactggcac cacggagcag tacagtactc   8760
aggaggccgg ttcaccatcc ctacaggtgc gggcaaacca ggggacagcg gtagaccgat   8820
cttcgacaac aaggggcgcg tggtggccat agttttagga ggagctaatg aaggagcccg   8880
tacagccctc tcggtggtga cctggaacaa agacatcgtc acgaaaatca cccctgaggg   8940
ggccgaagag tggagtcttg ccattccagt tatgtgcctg ctggcaaata ccacgttccc   9000
ctgctcccag cccccttgca caccctgctg ctacgaaaaa gagccggaga aaaccctgcg   9060
catgctagaa gacaacgtca tgagccccgg gtactatcag ctgctacaag catccttaac   9120
atgttctccc cgccgccagc gacgcagtat taaggacaac ttcaatgtct ataaagccat   9180
aagaccgtac ctagctcact gtcccgactg tggagaaggg cactcgtgcc atagtcccgt   9240
agcgctagaa cgcatcagaa acgaagcgac agacgggacg ctgaaaatcc aggtttcctt   9300
gcaaatcgga ataaagacgg atgatagcca tgattggacc aagctgcgtt acatggacaa   9360
tcatatgcca gcagacgcag agagggccag gctatttgta agaacgtcag caccgtgcac   9420
gattactgga acaatgggac acttcatcct ggcccgatgt ccgaaaggag aaactctgac   9480
ggtgggattc actgacggta ggaagatcag tcactcatgt acgcacccat ttcaccacga   9540
ccctcctgtg ataggccggg aaaaatttca ttcccgaccg cagcacggta gagaactacc   9600
ttgcagcacg tacgcgcaga gcaccgctgc aactgccgag gagatagagg tacatatgcc   9660
cccagacacc ccagatcgca cattgatgtc acaacagtcc ggtaatgtaa agatcacagt   9720
caatagtcag acggtgcggt acaagtgtaa ttgcggtgac tcaaatgaag gactaaccac   9780
tacagacaaa gtgattaata actgcaaggt tgatcaatgc catgccgcgg tcaccaatca   9840
caaaaaatgg cagtataatt cccctctggt cccgcgtaat gctgaactcg ggaccgaaa   9900
aggaaaagtt cacattccgt ttcctctggc aaatgtgaca tgcagggtgc ctaaggcaag   9960
gaaccccacc gtgacgtacg gaaaaaacca agtcatcatg ctgctgtatc ctgaccaccc   10020
aacgctcctg tcctaccgga atatgggaga agaaccaaac tatcaagaag agtgggtgac   10080
gcataagaag gagatcaggt taaccgtgcc gactgaaggg ctcgaggtca cgtggggcaa   10140
caacgagccg tacaagtatt ggccgcagtt atccacaaac ggtacagccc acggccaccc   10200
gcatgagata attttgtatt attatgagct gtaccctact atgactgtgg tagttgtgtc   10260
agtggcctcg ttcgtactcc tgtcgatggt gggtgtggca gtggggatgt gcatgtgtgc   10320
acgacgcaga tgcattacac cgtacgaact gacaccagga gctaccgtcc ctttcctgct   10380
tagcctaata tgctgcatta gaacagctaa agcggccaca taccaagagg ctgcggtata   10440
cctgtggaac gagcagcagc ctttgttttg gctgcaagcc cttattccgc tggcagccct   10500
gattgtccta tgcaactgtc tgagactctt accatgcttt tgtaaaacgt tgactttttt   10560
agccgtaatg agcgtcggtg cccacactgt gagcgcgtac gaacacgtaa cagtgatccc   10620
gaacacggtg ggagtaccgt ataagactct agtcaacaga ccgggctaca gccccatggt   10680
actggagatg gagcttctgt cagtcacttt ggagccaacg ctatcgcttg attacatcac   10740
gtgcgagtat aaaaccgtca tcccgtctcc gtacgtgaaa tgctgcggta cagcagagtg   10800
caaggacaag agcctacctg attacagctg taaggtcttc accggcgtct acccattcat   10860
```

```
gtggggcggc gcctactgct tctgcgacac tgaaaatacg caattgagcg aagcacatgt  10920

ggagaagtcc gaatcatgca aaacagaatt tgcatcagca tatagggctc ataccgcatc  10980

cgcatcagct aagctccgcg tcctttacca aggaaataat gttactgtat ctgcttatgc  11040

aaacggcgat catgccgtca cagttaagga cgctaaattc attgtggggc caatgtcttc  11100

agcctggaca ccttttgaca ataaaatcgt ggtgtacaaa ggcgacgtct acaacatgga  11160

ctacccgccc ttcggcgcag gaagaccagg acaatttggc gacatccaaa gtcgcacgcc  11220

tgagagcgaa gacgtctatg ctaacacaca actggtactg cagagaccgt ccgcgggtac  11280

ggtgcacgtg ccgtactctc aggcaccatc tggcttcaag tattggctaa aagaacgagg  11340

ggcgtcgctg cagcacacag caccatttgg ctgtcaaata gcaacaaacc cggtaagagc  11400

gatgaactgc gccgtaggga acatgcctat ctccatcgac ataccggacg cggccttcac  11460

tagggtcgtc gacgcgccat ctttaacgga catgtcgtgt gaggtaccag cctgcaccca  11520

ctcctcagac tttgggggcg tagccatcat taaatatgca gccagcaaga aaggcaagtg  11580

tgcggtgcat tcgatgacta acgccgtcac tattcgggaa gctgaaatag aagtagaagg  11640

gaactctcag ttgcaaatct ctttttcgac ggccctagcc agcgccgaat tccgcgtaca  11700

agtctgttct acacaagtac actgtgcagc cgagtgccat ccaccgaaag accatatagt  11760

caattacccg gcgtcacaca ccaccctcgg ggtccaagac atttccgtta cggcgatgtc  11820

atgggtgcag aagatcacgg gaggtgtggg actggttgtc gctgttgcag cactgatcct  11880

aatcgtggtg ctatgcgtgt cgtttagcag gcactgaata cagcagcaat tggcaagctg  11940

cttacataga actcgcggcg attggcatgc cgccttaaaa tttttatttt atttttttctt  12000

ttcttttccg aatcggattt tgtttttaat atttcaaaaa aaaaaaaaaa aaaaaagggt  12060

acgcggccgc cactgtgctg gatatctgca gaattccacc acactggact agtggatcag  12120

cttaagttta aaccgctgat cagcctcgac tgtgccttct agttgccagc cat         12173
```

<210> SEQ ID NO 6
<211> LENGTH: 12944
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ggcgcgcctg acattgatta ttgactagtt attaatagta atcaattacg gggtcattag     60

ttcatagccc atatatggag ttccgcgtta cataacttac ggtaaatggc ccgcctggct    120

gaccgcccaa cgacccccgc ccattgacgt caataatgac gtatgttccc atagtaacgc    180

caatagggac tttccattga cgtcaatggg tggagtattt acggtaaact gcccacttgg    240

cagtacatca agtgtatcat atgccaagta cgccccctat tgacgtcaat gacggtaaat    300

ggcccgcctg gcattatgcc cagtacatga ccttatggga ctttcctact tggcagtaca    360

tctacgtatt agtcatcgct attaccatgg tgatgcggtt ttggcagtac atcaatgggc    420

gtggatagcg gtttgactca cggggatttc caagtctcca ccccattgac gtcaatggga    480

gtttgttttg gcaccaaaat caacgggact ttccaaaatg tcgtaacaac tccgccccat    540

tgacgcaaat gggcggtagg cgtgtacggt gggaggtcta tataagcaga gctctctggc    600

taactagaga tggctgcgtg agacacacgt agcctaccag tttcttactg ctctactctg    660

caaagcaaga gattaataac ccatcatgga ttctgtgtac gtggacatag acgctgacag    720
```

-continued

```
cgccttttttg aaggccctgc aacgtgcgta ccccatgttt gaggtggaac ctaggcaggt    780
cacatcgaat gaccatgcta atgctagagc gttctcgcat ctagccataa aactaataga    840
gcaggaaatt gatcccgact caaccatcct ggatataggt agtgcgccag caaggaggat    900
gatgtcggac aggaagtacc actgcgtttg cccgatgcgc agcgcagaag atcccgagag    960
actcgctaat tatgcgagaa agctcgcatc tgccgcagga aaagtcctgg acagaaacat   1020
ttctggaaag atcggggact tacaagcggt gatggccgtg ccagacacgg agacgccaac   1080
attttgctta cacacagatg tctcatgtag acagagagca gacgtcgcga tataccaaga   1140
cgtctatgct gtacacgcac ccacgtcgct ataccaccag gcgattaaag gagtccgagt   1200
ggcgtactgg gtagggttcg acacaacccc gttcatgtac aacgctatgg cgggtgccta   1260
cccctcatac tcgacaaatt gggcggatga gcaggtactg aaggctaaga acataggatt   1320
atgttcaaca gacctgacgg aaggtagacg aggcaaattg tctatcatga gagggaaaaa   1380
gctaaaaccg tgcgaccgtg tgctgttctc agtagggtca acgctttacc cggaaagccg   1440
cacgctactt aagagctggc acctaccatc ggtgttccat ctaaagggca agcttagctt   1500
cacatgccgc tgtgacacag tggtttcgtg tgagggctac gtcgttaaga gaataacgat   1560
gagcccaggc ctttatggaa aaaccatagg gtatgcggta acccaccacg cagacggatt   1620
cttgatgtgc aagactaccg acacggttga cggcgaaaga gtgtcattct cggtgtgcac   1680
gtacgtgccg gcgaccattt gtgatcaaat gaccggcatc cttgctacag aagtcacgcc   1740
ggaggatgca cagaagctgt tggtggggct gaaccagagg atagtggtta acggcagaac   1800
gcaacggaac acgaacacca tgaagaacta cctacttccc gtggtcgccc aggccttcag   1860
taagtgggca aaggagtgcc ggaaggacat ggaagatgag aagcttctgg gggtcagaga   1920
aagaacacta acctgctgct gtctatgggc atttaagaag cagaaaacac acacggtcta   1980
caagaggcct gatacccagt caatccagaa ggttcaggcc gaatttgaca gctttgtagt   2040
accgggcctg tggtcgtccg ggttgtcaat cccgttgagg actagaatca agtggttgtt   2100
acgcaaggtg ccgaaaacag acctgatccc atacagcggg aatgcccaag aagcccagga   2160
tgcagaaaaa gaagcagagg aagaacgaga agcagaactg actcatgagg ctctaccacc   2220
cctacaggca gcacaggaag atgtccaggt cgaaatcgac gtggaacagc ttgaggatag   2280
agctggtgct ggaataatag agactccgag aggcgctatc aaagttactg cccaactaac   2340
agaccacgtc gtgggggagt acctggtact ttccccgcag accgtactac gcagccagaa   2400
gctcagcctg atccacgctt tagcggagca agtgaagacg tgtacgcaca gcggacgagc   2460
agggaggtat gcggtcgaag cgtacgatgg ccgagtccta gtgccctcag gctatgcaat   2520
ttcgcctgaa gacttccaga gtctaagcga aagcgcaacg atggtgtaca acgaaagaga   2580
gttcgtaaac agaaagttac accacattgc gatgcacgga ccagccctga acactgacga   2640
agagtcgtat gagctggtga gggcagagag gacagaacac gagtacgtct acgacgtgga   2700
ccagagaaga tgctgtaaga aggaagaagc tgcaggactg gtactggtgg gcgacttgac   2760
taatccgccc taccacgaat tcgcatacga agggctaaaa attcgccccg cctgcccata   2820
caaaattgca gtcataggag tcttcggggt accaggatct ggcaagtcag ccattatcaa   2880
gaacctagtt accaggcaag acctggtgac tagcggaaag aaagaaaact gccaagaaat   2940
cagcaccgac gtgatgagac agagaggtct agagatatct gcacgtacgg tagattcgct   3000
gctcttgaat ggatgcaaca gaccagtcga cgtgttgtac gtagacgagg cgtttgcgtg   3060
```

-continued

```
ccactctgga acgttacttg ctttgatcgc cttggtgaga ccaagacaga aagttgtact   3120
ttgtggtgac ccgaagcagt gcggcttctt caatatgatg cagatgaaag tcaactacaa   3180
tcataacatc tgcacccaag tgtaccacaa aagtatctcc aggcggtgta cactgcctgt   3240
gactgccatt gtgtcatcgt tgcattacga aggcaaaatg cgcactacga atgagtacaa   3300
catgccgatt gtagtggaca ctacaggctc aacgaaacct gaccctggag acctcgtgtt   3360
aacgtgcttc agagggtggg ttaaacaact gcaaattgac tatcgtggac acgaggtcat   3420
gacagcagcc gcatcccaag ggttaactag aaaaggagtt tacgcagtta ggcaaaaagt   3480
taacgaaaac ccactctatg catcaacatc agagcacgtc aacgtactcc taacgcgtac   3540
ggaaggtaaa ctggtatgga agacactctc tggtgacccg tggataaaga cgctgcagaa   3600
cccaccgaaa ggaaacttca aagcaactat taaggagtgg gaggtggagc acgcatcgat   3660
aatggcgggc atctgcagtc accaagtgac ctttgacaca ttccaaaaca aagccaacgt   3720
ttgctgggct aagagcttgg tccctatcct cgaaacagcg gggataaaac taaatgatag   3780
gcagtggtcc cagataattc aagccttcaa agaagacaaa gcatactcac ccgaagtagc   3840
cctgaatgaa atatgcacgc gcatgtatgg ggtggatcta gacagtgggc tattctctaa   3900
accgttggta tctgtgtatt acgcggataa ccattgggat aataggccgg gaggaaagat   3960
gttcggattc aaccctgagg cagcgtccat tctagaaaga aagtacccat ttacaaaagg   4020
aaagtggaac atcaacaagc agatctgcgt gactaccagg aggatagaag acttcaaccc   4080
taccaccaac attataccgg tcaacaggag actaccacac tcattagtgg ccgaacaccg   4140
cccagtaaaa ggggaaagaa tggaatggct ggttaacaag ataaacggac accacgtact   4200
cctggttagc ggctataacc ttgcactgcc tactaagaga gtcacctggg tagcgccact   4260
aggtgtccgc ggagcggact atacatacaa cctagagctg ggtctaccag caacrcttgg   4320
taggtatgac ctagtggtca taaacatcca cacacctttt cgcatacacc attaccaaca   4380
gtgcgtagat cacgcaatga aactgcaaat gctagggggt gactcactga gactgctcaa   4440
accgggtggc tctctattga tcagagcata cggttacgca gatagaacca gtgaacgagt   4500
catctgcgta ctgggacgca agtttagatc gtctagagca ttgaaaccac catgtgtcac   4560
cagtaatact gagatgtttt tcctatttag caattttgac aatggcagaa ggaattttac   4620
aacgcatgtc atgaacaatc aactgaatgc agcctttgta ggacaggcca cccgagcagg   4680
atgtgcacca tcgtaccggg taaaacgcat ggacatcgcg aagaacgatg aagagtgcgt   4740
ggttaacgcc gccaaccctc gcgggttacc aggtgacggt gtttgcaagg cagtatataa   4800
aaagtggccg gagtccttta aaaacagtgc aacaccagta ggaaccgcaa aaacagttat   4860
gtgcggtacg tatccagtaa tccacgccgt aggaccaaac ttctcaaatt attcggagtc   4920
tgaaggggac cgggaattgg cggctgccta tcgagaagtc gcaaaggaag taactagact   4980
gggagtaaat agcgtagcta tacctctcct ctccacaggt gtatactcag gagggaaaga   5040
caggctaacc cagtcactga accacctctt tacagccatg gactcgacgg atgcagacgt   5100
ggtcatctac tgccgagaca aggaatggga gaagaaaata tctgaggcca tacagatgcg   5160
gacccaagtg gagctgctgg atgagcacat ctccatagac tgcgatgtca ttcgcgtgca   5220
ccctgacagt agcttggcag gcagaaaagg atacagcacc acggaaggcg cactgtattc   5280
atatctagaa gggacacgtt ttcaccagac ggcagtggat atggcagaga tatacactat   5340
gtggccaaag caaacagagg ccaatgagca agtctgccta tatgccctgg gggaaagtat   5400
tgaatcaatc aggcagaaat gcccggtgga tgatgcagac gcatcatctc cccgaaaac    5460
```

-continued

```
tgtcccgtgt ctttgccggt atgccatgac tcctgaacgc gtcacccgac ttcgcatgaa   5520
ccatgtcaca aatataattg tgtgttcttc atttcccctt ccaaagtaca agatagaagg   5580
agtgcaaaaa gtcaaatgct ccaaggtaat gttattcgat cacaatgtgc catcgcgcgt   5640
aagtccaagg gaatacagat cttcccagga gtctgtacag gaagtgagta cgacaacgtc   5700
attgacgcat agccagtttg atctaagcgc cgatggcgag acactgcctg tcccgtcaga   5760
cctggatgct gacgccccag ccctagaacc ggccctagac gacggggcgg tacatacatt   5820
accaaccata atcggaaacc ttgcggccgt gtctgactgg gtaatgagca ccgtacctgt   5880
cgcgccgcct agaagaagga gagggagaaa cctgactgtg acatgtgacg agagagaagg   5940
gaatataaca cccatggcta gcgtccgatt ctttagagca gagctgtgtc cggccgtaca   6000
agaaacagcg gagacgcgtg acacagctat ttcccttcag gcaccgccaa gtaccaccat   6060
ggaactgagc catccaccga tctccttcgg agcaccaagc gagacgttcc ccatcacatt   6120
tggggacttc gacgaaggag aaatcgaaag cttgtcttct gagctactaa ctttcggaga   6180
cttcctaccc ggtgaagtgg atgatctgac agatagcgac tggtccacgt gcccagacac   6240
ggacgacgag ttatgactag acagggcagg tgggtatata ttctcgtcgg acactggtcc   6300
aggccattta caacagaagt cggtacgcca gtcagtgctg ccggtaaaca ccctggagga   6360
agtccacgag gagaagtgtt acccacctaa gctggatgaa ttaaaggagc aactactact   6420
taagaaactc caggagagtg cgtccatggc caatagaagc aggtatcagt cacgcaaagt   6480
ggaaaatatg aaagcaacaa tcatccagag actaaagaga ggctgtaaac tgtatttaat   6540
ggcagagacc ccgaaagtcc cgacttatcg gaccatatac ccggcgcctg tgtactcgcc   6600
tccgatcaat gtccgattgt ccaaccccga gtccgcagtg gcagcatgta atgagttctt   6660
agctagaaac tacccaactg tttcatcata ccaaatcacc gacgagtatg atgcatatct   6720
agacatggtg gacgggtcgg agagttgctt ggaccgagcg acattcaatc cgtcaaaact   6780
taggagctac ccgaaacaac atgcttatca cgcgccttct atcagaagcg ctgtaccttc   6840
cccattccag aacacactac agaatgtact ggcagcagcc acgaaaagga actgcaacgt   6900
cacacagatg agggaattac ccactttgga ctcagcagta ttcaacgtgg agtgttttaa   6960
aaaattcgca tgtaaccgag aatactggga agaatttgca gccagcccta tcaggataac   7020
aactgagaat ctaacaacct atgtcactaa actaaagggg ccaaaagcag cagcgctgtt   7080
tgcaaaaacc cataatctgc tgccactgca ggatgtacca atggataggt tcacagtaga   7140
tatgaaaagg gatgtgaagg taactcctgg tacaaagcat acagaggaaa gacctaaggt   7200
gcaggttata caggcggctg aacccttggc aacagcgtac ctatgtggaa ttcacagaga   7260
actggttagg agattgaacg ccgtcctcct acccaatgtg catacactat ttgacatgtc   7320
tgccgaggac ttcgatgcca ttatagccgc acacttcaag ccaggagacg ctgttttaga   7380
aacggacata gcctcctttg ataagagcca agatgattca cttgcgctta ccgccttaat   7440
gctgttagaa gatttgggag tggatcactc cctgttggac ttgatagagg ctgctttcgg   7500
agagatttcc agctgtcatc tgccgacagg tacgcgcttc aagttcggcg ctatgatgaa   7560
atccggtatg ttcctaactc tgttcgtcaa cacgttgtta aatatcacca tcgctagccg   7620
ggtgttggaa gatcgtctga caaaatccgc atgcgcggcc ttcatcggcg acgacaacat   7680
aatacatggt gtcgtctccg atgaattgat ggcagccaga tgcgctactt ggatgaacat   7740
ggaagtgaag atcatagatg cagttgtatc ccagaaagct ccttactttt gtggagggtt   7800
```

-continued

```
tatactgcat gatactgtga caggaacagc ttgcagagtg gcggacccgc taaaaaggtt   7860
atttaaattg ggcaaaccgt tagcggcagg tgacgaacaa gatgaagaca gaagacgggc   7920
gctggctgat gaagtaatca gatggcaacg aacagggcta atagatgagc tggagaaagc   7980
ggtgtactct aggtacgaag tgcagggtat atcagttgcg gtaatgtcca tggccacctt   8040
tgcaagctcc agatccaact tcgagaagct cagaggaccc gtcataactt tgtacggcgg   8100
tcctaaatag gtacgcacta cagctaccta ttttgcagaa gccgacagca ggtacctaaa   8160
taccaatcag ccataatgtt cccgttccag ccaatgtatc cgatgcagcc aatgccctat   8220
cgcaacccgt tcgcggcccc gcgcaggccc tggttcccca gaaccgaccc ttttctggcg   8280
atgcaggtgc aggaattaac ccgctcgatg gctaacctga cgttcaagca acgccgggac   8340
gcgccacctg aggggccatc cgctaagaaa ccgaagaagg aggcctcgca aaaacagaaa   8400
gggggaggcc aagggaagaa gaagaagaac caagggaaga agaaggctaa gacagggccg   8460
cctaatccga aggcacagaa tggaaacaag aagaagacca acaagaaacc aggcaagaga   8520
cagcgcatgg tcatgaaatt ggaatctgac aagacgttcc caatcatgtt ggaagggaag   8580
ataaacggct acgcttgtgt ggtcggaggg aagttattca ggccgatgca tgtggaaggc   8640
aagatcgaca acgacgttct ggccgcgctt aagacgaaga aagcatccaa atacgatctt   8700
gagtatgcag atgtgccaca gaacatgcgg gccgatacat tcaaatacac ccatgagaaa   8760
ccccaaggct attacagctg gcatcatgga gcagtccaat atgaaaatgg gcgtttcacg   8820
gtgccgaaag gagttggggc caagggagac agcggacgac ccattctgga taaccaggga   8880
cgggtggtcg ctattgtgct gggaggtgtg aatgaaggat ctaggacagc cctttcagtc   8940
gtcatgtgga acgagaaggg agttaccgtg aagtatactc cggagaactg cgagcaatgg   9000
tcactagtga ccaccatgtg tctgctcgcc aatgtgacgt tcccatgtgc tcaaccacca   9060
atttgctacg acagaaaacc agcagagact ttggccatgc tcagcgttaa cgttgacaac   9120
ccgggctacg atgagctgct ggaagcagct gttaagtgcc ccggaaggaa aaggagatcc   9180
accgaggagc tgtttaatga gtataagcta acgcgccctt acatggccag atgcatcaga   9240
tgtgcagttg ggagctgcca tagtccaata gcaatcgagg cagtaaagag cgacgggcac   9300
gacggttatg ttagacttca gacttcctcg cagtatggcc tggattcctc cggcaactta   9360
aagggcagga ccatgcggta tgacatgcac gggaccatta aagagatacc actacatcaa   9420
gtgtcactct atacatctcg cccgtgtcac attgtggatg ggcacggtta tttcctgctt   9480
gccaggtgcc cggcagggga ctccatcacc atggaattta agaaagattc cgtcagacac   9540
tcctgctcgg tgccgtatga agtgaaattt aatcctgtag gcagagaact ctatactcat   9600
cccccagaac acggagtaga gcaagcgtgc caagtctacg cacatgatgc acagaacaga   9660
ggagcttatg tcgagatgca cctcccgggc tcagaagtgg acagcagttt ggtttccttg   9720
agcggcagtt cagtcaccgt gacacctcct gatgggacta gcgccctggt ggaatgcgag   9780
tgtggcggca caaagatctc cgagaccatc aacaagacaa aacagttcag ccagtgcaca   9840
aagaaggagc agtgcagagc atatcggctg cagaacgata agtgggtgta taattctgac   9900
aaactgccca aagcagcggg agccacctta aaaggaaaac tgcatgtccc attcttgctg   9960
gcagacggca aatgcaccgt gcctctagca ccagaaccta tgataacctt cggtttcaga  10020
tcagtgtcac tgaaactgca ccctaagaat cccacatatc taatcacccg ccaacttgct  10080
gatgagcctc actacacgca cgagctcata tctgaaccag ctgttaggaa ttttaccgtc  10140
accgaaaaag ggtgggagtt tgtatgggga aaccacccgc cgaaaaggtt ttgggcacag  10200
```

```
gaaacagcac ccggaaatcc acatgggcta ccgcacgagg tgataactca ttattaccac  10260
agatacccta tgtccaccat cctgggtttg tcaatttgtg ccgccattgc aaccgtttcc  10320
gttgcagcgt ctacctggct gttttgcaga tctagagttg cgtgcctaac tccttaccgg  10380
ctaacaccta acgctaggat accattttgt ctggctgtgc tttgctgcgc ccgcactgcc  10440
cgggccgaga ccacctggga gtccttggat cacctatgga acaataacca acagatgttc  10500
tggattcaat tgctgatccc tctggccgcc ttgatcgtag tgactcgcct gctcaggtgc  10560
gtgtgctgtg tcgtgccttt tttagtcatg gccggcgccg caggcgccgg cgcctacgag  10620
cacgcgacca cgatgccgag ccaagcggga atctcgtata acactatagt caacagagca  10680
ggctacgcac cactccctat cagcataaca ccaacaaaga tcaagctgat acctacagtg  10740
aacttggagt acgtcacctg ccactacaaa acaggaatgg attcaccagc catcaaatgc  10800
tgcggatctc aggaatgcac tccaacttac aggcctgatg aacagtgcaa agtcttcaca  10860
ggggtttacc cgttcatgtg ggtggtgca tattgcttt gcgacactga gaacacccaa  10920
gtcagcaagg cctacgtaat gaaatctgac gactgccttg cggatcatgc tgaagcatat  10980
aaagcgcaca cagcctcagt gcaggcgttc ctcaacatca cagtgggaga acactctatt  11040
gtgactaccg tgtatgtgaa tggagaaact cctgtgaatt tcaatggggt caaaataact  11100
gcaggtccgc tttccacagc ttggacaccc tttgatcgca aaatcgtgca gtatgccggg  11160
gagatctata attatgattt tcctgagtat ggggcaggac aaccaggagc atttggagat  11220
atacaatcca gaacagtctc aagctctgat ctgtatgcca ataccaacct agtgctgcag  11280
agacccaaag caggagcgat ccacgtgcca tacactcagg caccttcggg ttttgagcaa  11340
tggaagaaag ataaagctcc atcattgaaa tttaccgccc ctttcggatg cgaaatatat  11400
acaaacccca ttcgcgccga aaactgtgct gtagggtcaa ttccattagc ctttgacatt  11460
cccgacgcct tgttcaccag ggtgtcagaa acaccgacac tttcagcggc cgaatgcact  11520
cttaacgagt gcgtgtattc ttccgacttt ggtgggatcg ccacggtcaa gtactcggcc  11580
agcaagtcag gcaagtgcgc agtccatgtg ccatcaggga ctgctaccct aaaagaagca  11640
gcagtcgagc taaccgagca agggtcggcg actatccatt tctcgaccgc aaatatccac  11700
ccggagttca ggctccaaat atgcacatca tatgttacgt gcaaaggtga ttgtcacccc  11760
ccgaaagacc atattgtgac acaccctcag tatcacgccc aaacatttac agccgcggtg  11820
tcaaaaaccg cgtggacgtg gttaacatcc ctgctgggag gatcagccgt aattattata  11880
attggcttgg tgctggctac tattgtggcc atgtacgtgc tgaccaacca gaaacataat  11940
tgacttgaca actaggtacg aaggtatatg tgtcccctaa gagacacacc acatatagct  12000
aagaatcaat agataagtat agatcaaagg gctgaacaac ccctgaatag taacaaaata  12060
taaaaatcaa caaaaatcat aaaatagaaa accagaaaca gaagtaggta agaaggtata  12120
tgtgtcccct aagagacaca ccatatatag ctaagaatca atagataagt atagatcaaa  12180
gggctgaata acccctgaat aataacaaaa tataaaaatc aataaaaatc ataaaataga  12240
aaaccataaa cagaagtagt tcaaagggct ataaaacccc tgaatagtaa caaaacataa  12300
aactaataaa aatcaaatga ataccataat tggcaatcgg aagagatgta ggtacttaag  12360
cttcctaaaa gcagccgaac tcgctttgag atgtaggcgt agcacaccga actcttccat  12420
aattctccga acccacaggg acgtaggaga tgttcaaagt ggctataaaa ccctgaacag  12480
taataaaaca taaaattaat aaggatcaaa tgagtaccat aattggcaaa cggaagagat  12540
```

```
gtaggtactt aagcttccta aaagcagccg aactcacttt gagatgtagg catagcatac  12600

cgaactcttc cacaattctc cgtacccata gggacgtagg agatgttatt ttgtttttaa  12660

tatttcaaaa aaaaaaaaaa aaaaaaaggg tacgcggccg ccactgtgct ggatatctgc  12720

agaattccac cacactggac tagtggatca gcttaagttt aaaccgctga tcagcctcga  12780

ctgtgccttc tagttgccag ccatctgttg tttgcccctc ccccgtgcct tccttgaccc  12840

tggaaggtgc cactcccact gtcctttcct aataaaatga ggaaattgca tcgcattgtc  12900

tgagtaggtg tcattctatt ctggggggtg gggtggggca ggac                  12944
```

<210> SEQ ID NO 7
<211> LENGTH: 60
<212> TYPE: PRT
<213> ORGANISM: Chikungunya virus

<400> SEQUENCE: 7

```
Thr Gly Tyr Ala Val Thr His His Ala Asp Gly Phe Leu Met Cys Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

<210> SEQ ID NO 8
<211> LENGTH: 60
<212> TYPE: PRT
<213> ORGANISM: Chikungunya virus

<400> SEQUENCE: 8

```
Thr Gly Tyr Ala Val Thr His His Ala Asp Gly Phe Leu Met Cys Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

<210> SEQ ID NO 9
<211> LENGTH: 60
<212> TYPE: PRT
<213> ORGANISM: Chikungunya virus

<400> SEQUENCE: 9

```
Thr Gly Tyr Ala Val Thr His His Ala Asp Gly Phe Leu Met Cys Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

<210> SEQ ID NO 10
<211> LENGTH: 60
<212> TYPE: PRT
<213> ORGANISM: Chikungunya virus

<400> SEQUENCE: 10

Thr Gly Tyr Ala Val Thr His His Ala Asp Gly Phe Leu Leu Cys Lys
1 5 10 15

Thr Thr Asp Thr Val Asp Gly Glu Arg Val Ser Phe Ser Val Cys Thr
20 25 30

Tyr Val Pro Ala Thr Ile Cys Asp Gln Met Thr Gly Ile Leu Ala Thr
35 40 45

Glu Val Thr Pro Glu Asp Ala Gln Lys Leu Leu Val
50 55 60

<210> SEQ ID NO 11
<211> LENGTH: 60
<212> TYPE: PRT
<213> ORGANISM: Chikungunya virus

<400> SEQUENCE: 11

Thr Gly Tyr Ala Val Thr His His Ala Asp Gly Phe Leu Leu Cys Lys
1 5 10 15

Thr Thr Asp Thr Val Asp Gly Glu Arg Val Ser Phe Ser Val Cys Thr
20 25 30

Tyr Val Pro Ala Thr Ile Cys Asp Gln Met Thr Gly Ile Leu Ala Thr
35 40 45

Glu Val Thr Pro Glu Asp Ala Gln Lys Leu Leu Val
50 55 60

<210> SEQ ID NO 12
<211> LENGTH: 60
<212> TYPE: PRT
<213> ORGANISM: Chikungunya virus

<400> SEQUENCE: 12

Thr Gly Tyr Ala Val Thr His His Ala Asp Gly Phe Leu Leu Cys Lys
1 5 10 15

Thr Thr Asp Thr Val Asp Gly Glu Arg Val Ser Phe Ser Val Cys Thr
20 25 30

Tyr Val Pro Ala Thr Ile Cys Asp Gln Met Thr Gly Ile Leu Ala Thr
35 40 45

Glu Val Thr Pro Glu Asp Ala Gln Lys Leu Leu Val
50 55 60

<210> SEQ ID NO 13
<211> LENGTH: 60
<212> TYPE: PRT
<213> ORGANISM: Chikungunya virus

<400> SEQUENCE: 13

Thr Gly Tyr Ala Val Thr His His Ala Asp Gly Phe Leu Leu Cys Lys
1 5 10 15

Thr Thr Asp Thr Val Asp Gly Glu Arg Val Ser Phe Ser Val Cys Thr
20 25 30

Tyr Val Pro Ala Thr Ile Cys Asp Gln Met Thr Gly Ile Leu Ala Thr
35 40 45

Glu Val Thr Pro Glu Asp Ala Gln Lys Leu Leu Val
50 55 60

<210> SEQ ID NO 14
<211> LENGTH: 60
<212> TYPE: PRT
<213> ORGANISM: Chikungunya virus

<400> SEQUENCE: 14

```
Thr Gly Tyr Ala Val Thr His His Ala Asp Gly Phe Leu Leu Cys Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

<210> SEQ ID NO 15
<211> LENGTH: 60
<212> TYPE: PRT
<213> ORGANISM: Chikungunya virus

<400> SEQUENCE: 15

```
Thr Gly Tyr Ala Val Thr His His Ala Asp Gly Phe Leu Met Ser Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

<210> SEQ ID NO 16
<211> LENGTH: 60
<212> TYPE: PRT
<213> ORGANISM: Chikungunya virus

<400> SEQUENCE: 16

```
Thr Gly Tyr Ala Val Thr His His Ala Asp Gly Phe Leu Met Cys Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

<210> SEQ ID NO 17
<211> LENGTH: 60
<212> TYPE: PRT
<213> ORGANISM: Chikungunya virus

<400> SEQUENCE: 17

```
Ile Gly Tyr Ala Val Thr His His Ala Asp Gly Phe Leu Met Cys Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

<210> SEQ ID NO 18
<211> LENGTH: 60
<212> TYPE: PRT
<213> ORGANISM: Chikungunya virus -continued

```
<400> SEQUENCE: 18

Ile Gly Tyr Ala Val Thr His His Ala Asp Gly Phe Leu Met Cys Lys
1               5                   10                  15

Thr Thr Asp Thr Val Asp Gly Glu Arg Val Ser Phe Ser Val Cys Thr
            20                  25                  30

Tyr Val Pro Ala Thr Ile Cys Asp Gln Met Thr Gly Ile Leu Ala Thr
        35                  40                  45

Glu Val Thr Pro Glu Asp Ala Gln Lys Leu Leu Val
    50                  55                  60
```

INFECTIOUS DNA VACCINES AGAINST CHIKUNGUNYA VIRUS

CROSS-REFERENCE TO PRIOR APPLICATIONS

This application is a National Stage of PCT/US2011/000001, filed Jan. 3, 2011, and designating the United States (published in English on Jul. 7, 2011, as WO 2011/082388 A2; the title and abstract were also published in English), which claims priority of U.S. Provisional Patent Application No. 61/291,682, filed Dec. 31, 2009, each hereby expressly incorporated by reference in its entirety and each assigned to the assignee hereof.

GOVERNMENT INTERESTS

The U.S. Government provided the inventors with materials and/or reagents that may be related to the subject matter of this application. Accordingly, the U.S. government may have certain rights in the subject matter.

FIELD

Live attenuated and DNA vaccines against chikungunya virus and system and methods for making and administering such vaccines.

BACKGROUND

A variety of vaccines and systems and methods for making and administering the same have been suggested. However, such vaccines, systems and methods are not optimal.

SUMMARY

Described herein are vectors comprising DNA encoding an infectious RNA molecule and an RNA polymerase promoter, where the DNA encoding an infectious RNA molecule is operably linked to the RNA polymerase promoter and the infectious RNA molecules encodes a chikungunya virus (CHIKV). In certain embodiments, the CHIKV is non-pathogenic. Also described, are vaccines for chikungunya comprising the DNA described above, and methods for using the vaccines to immunize against a CHIKV. Also described, are homogenous clonally purified live attenuated CHIKV virus prepared from cultured cells transfected with the DNA described above, vaccines for chikungunya comprising the same, and methods for using the vaccines to immunize against a CHIKV virus.

This application also provides vectors comprising DNA encoding an infectious RNA molecule and a cytomegalovirus (CMV) RNA polymerase promoter, where the DNA encoding an infectious RNA molecule is operably linked to the CMV RNA polymerase promoter, the CMV RNA polymerase promoter is located from about 13 to about 17 (preferably 15 nucleotides as exemplified on FIGS. 3-7 and 9) nucleotide residues upstream of the 5' end of said DNA encoding an infectious RNA molecule, and the infectious RNA molecule encodes an attenuated CHIKV virus. In certain embodiments, the CHIKV is a chimeric virus containing sequences from CHIKV as well as from another alphavirus. In certain embodiments, the DNA encoding the infectious RNA is modified to improve characteristics of said infectious RNA and of the described vector.

In an exemplary embodiment a vector is described comprising: (a) DNA encoding an infectious RNA molecule; and (b) an RNA polymerase promoter; wherein: (i) the DNA encoding an infectious RNA molecule is operably linked to the RNA polymerase promoter; and (ii) the infectious RNA molecule encodes a chikungunya virus (CHIKV). In some examples, the infectious RNA molecule encodes a non-pathogenic chikungunya virus. In some examples, the RNA polymerase promoter comprises a cytomegalovirus (CMV) RNA polymerase promoter, the CMV RNA polymerase promoter is located from about 13 to about 17 nucleotide residues upstream of the 5' end of the DNA encoding an infectious RNA molecule, and the infectious RNA molecule encodes an attenuated CHIKV virus. In various examples, a vector can comprise the DNA sequence listed in FIGS. 3-7.

In some embodiments, the CHIKV is a chimeric virus containing sequences from CHIKV as well as from another alphavirus. The DNA encoding the infectious RNA may also be modified to improve characteristics of the infectious RNA and of the described vector.

A vaccine for chikungunya virus can comprise a therapeutically effective amount of such vectors. In other examples, a vaccine for chikungunya virus can comprise an attenuated CHIKV virus produced by isolating the CHIKV virus from cells transfected by the DNA vectors described herein. A homogeneous clonally purified live attenuated virus may be prepared from cultured cells transfected with the DNA vectors described herein. Such a preparation is particularly useful as a vaccine.

Alternatively, a vector may comprise (a) DNA encoding an infectious RNA molecule; and (b) an RNA polymerase promoter; wherein: (i) the DNA encoding an infectious RNA molecule is operably linked to the RNA polymerase promoter; and (ii) the infectious RNA molecule encodes an alphavirus and contains sequences from CHIKV as well as from another alphavirus. One example of such a vector comprises the sequence of FIG. 9.

The vectors and vaccines described herein are useful for providing a method for immunizing a mammal against a chikungunya virus comprising the step of administering the vaccine to a mammal, such as an animal or human.

BRIEF DESCRIPTION OF THE DRAWINGS

FIG. 1 illustrates a comparison of live attenuated vaccines, DNA vaccines, and the described CHIKV i-DNA™ vaccine.

FIGS. 3A-3E illustrate an example (nucleotide sequence) of i-DNA™ that encodes the 181/25 live attenuated vaccine (SEQ ID NO: 1). The precise 5' and 3' ends of i-DNA-encoded functional genomic RNA of CHIKV are determined by optimized CMV promoter and ribozyme, respectively.

FIGS. 4A-4E illustrate an example (nucleotide sequence) of i-DNA™ that encodes the 181/25 live attenuated vaccine without ribozyme sequences (SEQ ID NO: 2). The precise 5' end of i-DNA-encoded CHIKV RNA is determined by optimized CMV promoter. The location of 3' end of i-DNA™ encoded CHIKV RNA is unknown but such RNA is capable of replicating and generating live CHIKV.

FIGS. 5A-5E illustrate an example (nucleotide sequence) of i-DNA™ that encodes the 181/25 live attenuated vaccine with the duplicated 26S promoter (SEQ ID NO: 3). In this i-DNA™ construct, capsid (C) and glycoproteins (GPs) of CHIKV are encoded from separate 26S promoters within CHIKV RNA.

FIGS. 6A-6E illustrate an example (nucleotide sequence) of i-DNA™ that encodes the 181/25 live attenuated vaccine with the nuclear transport element at the 3' terminus (SEQ ID NO: 4). In this i-DNA™ construct, a nuclear transport element sequence is introduced prior to polyA. This sequence enhances transport of CHIKV RNA from the nucleus to the cytoplasm.

FIGS. 7A-7E illustrate an example (nucleotide sequence) of i-DNA™ that encodes the chimeric vaccine comprising the TC-83 live attenuated vaccine (SEQ ID NO: 5), in which its structural gene region is replaced with the structural gene region (C and GPs) of CHIKV 181/25 live attenuated vaccine.

FIGS. 9A-9E illustrate an example (nucleotide sequence) of chimeric CHIKV i-DNA™ derived from live attenuated strain 181/25 that contains C-GPs polyprotein from TC-83 (SEQ ID NO: 6). This chimeric i-DNA™ construct can be used as a vaccine against Venezuelan equine encephalitis virus (VEE). Structural polyproteins from the other alphaviruses also can be used in place of the TC-83 to develop CHIKV-based i-DNA™ vaccines against the respective alphaviruses.

FIG. 12 illustrates sequence variation within 181/25 IND vaccine (SEQ ID NOs: 7-18). The vaccine was resuspended in saline and passed once in CHO cells. Viral RNA was isolated, cDNA was prepared by reverse transcription PCR and cloned into pCR2.1 vector. The sequences of cloned cDNA fragments were determined and compared to known CHIKV sequences from GenBank.

DETAILED DESCRIPTION

Figure 2:
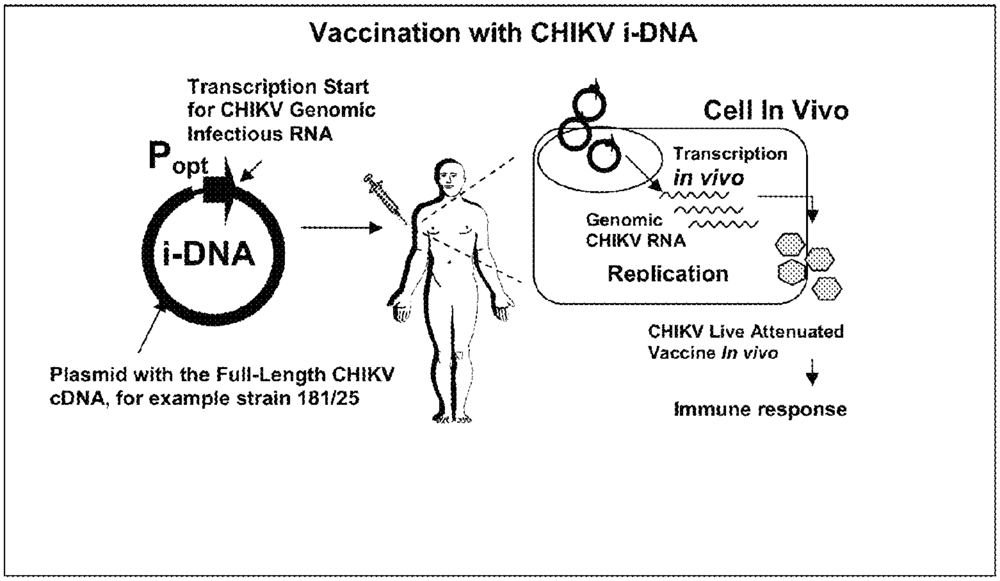
FIG. 2 illustrates an example CHIKV i-DNA™ vaccine and CHIKV i-DNA™ immunization. The full-length CHIKV cDNA is placed downstream from optimized promoter (Popt). In animal cells, for example cells of humans or mice, injected with i-DNA™, transcription from the promoter yields a full-length infectious genomic RNA capable of initiating productive replication of the CHIKV live attenuated virus particles and inducing specific immune responses.
Figure 8:
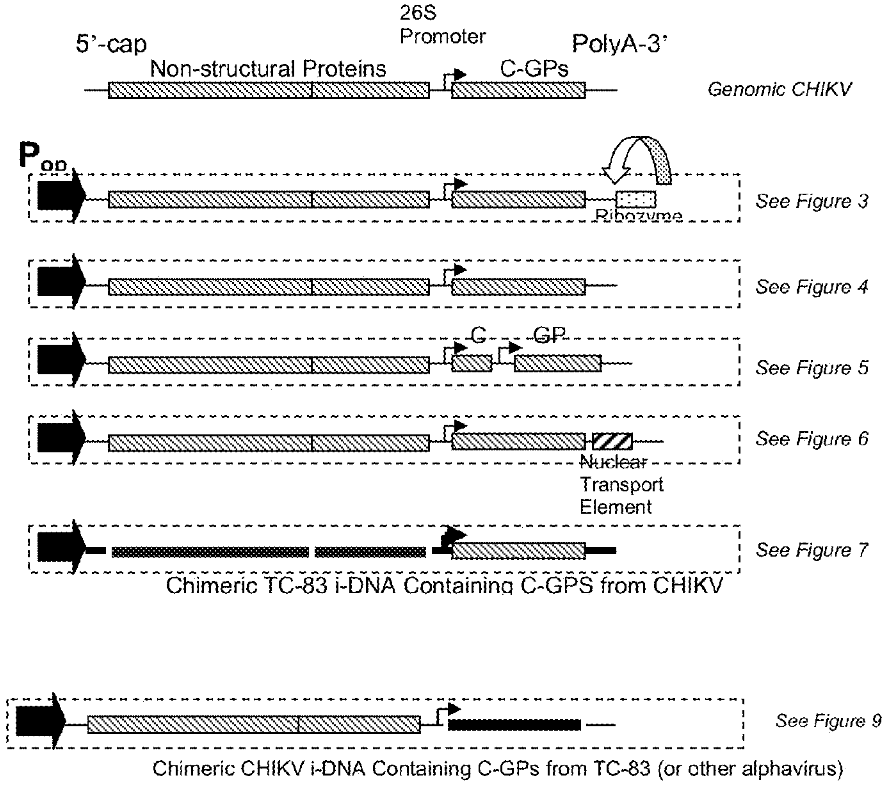
FIG. 8 illustrates the CHIKV i-DNA™ constructs from FIGS. 3-7. The genomic RNA from CHIKV is shown on the top. The i-DNA™ plasmid contains a DNA fragment (dashed box) that encodes (i) optimized eukaryotic promoter Popt (preferably optimized CMV promoter) and (ii) the full-length cDNA of CHIKV functional RNA encoding elements necessary for replication of genomic CHIKV RNA and generation of live attenuated CHIKV in vitro or in vivo. The indicated nucleotide sequence domains can be used in any of the constructs. For example, ribozyme (FIG. 3) can also be used in the constructs described in FIGS. 5-7 and 9.

Chikungunya is a mosquito-borne disease caused by Chikungunya virus (CHIKV). CHIKV is a member of the Alphavirus genus in the family Togaviridae. The Alphavirus genus consists of 29 distinct species (along with O’nyong’nyong virus, Ross River virus, Sindbis virus, Semliki Forest virus, VEE and others) that either cause encephalitis, febrile illness with arthralgia, or are not known to cause disease in humans. Members of this genus are primarily vector-borne; nearly all of them are utilizing mosquitoes as their invertebrate vectors (Powers and Brault, 2009). As used herein, CHIKV includes chimeric viruses that contain sequences from CHIKV as well as from another alphavirus, such chimeric viruses preferably comprising at least 50% CHIKV sequences and/or an antigenic portion of CHIKV.

Like all alphaviruses, CHIKV has a genome consisting of a linear, positive sense, single-stranded RNA molecule of approximately 12 kb in length (Khan et al., 2002). The non-structural proteins required for viral replication are encoded in the 5' two thirds of the genome and are regulated from 49S promoter, while the structural genes are collinear with the 3' one-third and utilize 26S internal promoter. The 5' end of the genome has a 7-methylguanosine cap while the 3' end is polyadenylated. There are also 3' noncoding repeat sequence elements that generate predicted secondary structures (Khan et al., 2002).

CHIKV causes explosive outbreaks and significant morbidity in many countries. The virus is widely spread and can easily be imported into naïve regions due to travel from endemic areas. CHIKV is also responsible for numerous laboratory acquired infections. Different approaches have been used to develop CHIKV vaccine including formalin inactivated (Kitaoka, 1967), live attenuated (Levitt et al., 1986) and chimeric alphavirus vaccine (Wang et al., 2008). Various formulations of potential CHIKV vaccines have been examined and subjected to human clinical trials (reviewed by (Powers and Brault, 2009). However, no licensed vaccine is currently available against chikungunya.

Vaccines are needed to control CHIKV. Ideally, the vaccine should have high degree of safety, induce efficient immunity and protection, be genetically stable, and not require a “cold chain” from vaccine manufacturer to vaccine recipient. Reduced cost and simplicity of production are important, because the main reservoir of CHIKV and the majority of cases are located in the tropical countries with limited resources.

Live attenuated vaccines against viral diseases are attractive because of rapid onset of immunity and efficient protection. Successful application of live attenuated vaccines resulted in the control of infectious diseases caused by many RNA viruses such as poliomyelitis, measles, mumps, rabies, rubella, and yellow fever. Approximately 60% of vaccines licensed for use in the U.S. are live attenuated vaccines. Among four viral vaccines recently approved by the FDA, three represent live attenuated vaccines—against rotavirus, influenza A and B, and varicella-zoster virus. This indicates that a live attenuated platform continues to be very attractive for vaccine development.

However, safety is the major concern for live attenuated vaccines. A typical live attenuated vaccine represents a population of viruses containing multiple genetic variants, or quasispecies that have various characteristics including pathogenic potential. The quasispecies diversity of RNA viruses can be associated with pathogenicity. Additionally, live associated vaccines contain impurities and adventitious agents derived from the cells that are used for vaccine manufacturing. Such impurities/adventitious agents can be associated with allergic reactions and elevated reactogenicity in the vaccine recipients.

Relatively recently, DNA vaccines have become a popular vaccination platform. A typical DNA vaccine contains a vaccine-relevant gene downstream from strong eukaryotic promoter, such as cytomegalovirus (CMV) promoter. For vaccination, DNA vaccine is injected into the tissues of a vaccine recipient, where it penetrates through the cellular and nuclear membranes of permissive cells. In the nuclei of host cells, transcription from CMV promoter occurs and the transcribed mRNA migrates from the nucleus into the cytoplasm, where translation and expression of vaccine-relevant antigen takes place. Thus, antigen is generated directly in the tissues of the vaccine recipient, which results in the induction of immunity to the antigen of interest. The advantage of DNA vaccines are the simplicity, low cost of production, the genetic stability, high level of purity and no need for a cold chain. The disadvantages of DNA vaccines are that multiple booster vaccinations and high quantities of DNA are required to induce an immune response. The need for multiple boost and high quantities of DNA injected into the nuclei of many cells raises concern that DNA vaccines can integrate into the host DNA and cause insertional mutagenesis.

Described herein is a novel chikungunya vaccine that combines the advantages of both live attenuated virus and DNA vaccine platforms. Namely, an "infectious DNA" (i-DNA™) CHIKV vaccine is described that represents a DNA vaccine that generates a live attenuated vaccine against chikungunya in vivo. The difference between the traditional DNA vaccine and the i-DNA™ vaccine described herein is that traditional DNA vaccine encodes a gene of interest, whereas i-DNA™ vaccine encodes the entire functional genomic RNA of live attenuated CHIKV. When CHIKV i-DNA™ is injected into vaccine recipient, it enters the nucleus and transcribes the entire infectious RNA of attenuated CHIKV, which initiates replication of live attenuated vaccine in the tissues in vivo and results in rapid induction of immunity to chikungunya.

This new platform for vaccination against CHIKV combines the advantages of conventional live attenuated and DNA vaccines (FIGS. 1 and 2). Like DNA vaccines, it is genetically stable, inexpensive and simple in manufacturing, and does not require a cold chain. Like live attenuated vaccine, it requires a single small dose to induce effective immunity.

While combining the advantages of both attenuated and DNA vaccine platforms, the CHIKV i-DNA™ vaccine lacks the disadvantages of both. Unlike live attenuated vaccines, the i-DNA™ is genetically stable and represents a homogenous, clonally purified and well-characterized DNA that can be easily purified to high levels of purity. Unlike conventional DNA vaccines, the CHIKV i-DNA™ is capable of inducing effective immunity with a single vaccination, with no multiple boosts. Also, only a low dose of i-DNA™ is needed. For example, a low dose of about 1 ng to about 1 μg, preferably about 10 ng to about 1 μg, and more preferably about 100 ng to about 1 μg of i-DNA™ could be used. Further, when compared with a conventional DNA vaccine, one could use about 5 fold to about 100 fold less i-DNA™, more preferably about 10 fold to about 100 fold less i-DNA™, even more preferably about 25 fold to about 100 fold less i-DNA™ and most preferably about 50 fold to about 100 fold less i-DNA™. The nucleus is only needed to generate the initial few copies of RNA genome, and after that, replication of live attenuated CHIKV virus occurs in the cell cytoplasm, thus drastically reducing the possibility of genetic mutagenesis of host DNA. For example, the use of the CHIKV i-DNA™ could reduce the possibility of genetic mutagenesis of host DNA by at least 50%, preferably by at least about 70%, more preferably by at least about 80%, even more preferably by at least about 90% and most preferably by about 100%.

The i-DNA™ can be utilized in various ways to create vaccines against CHIKV. For example, the i-DNA™ can be introduced by electroporation or any other acceptable way known in the art into eukaryotic cells acceptable for vaccine production. The live attenuated CHIKV generated from an i-DNA™ clone represents a homogenous virus population and contains a lower number of quisispecies thus representing an advantage over traditional live attenuated vaccines. For example, the virus population generated from an i-DNA™ clone could contain at least about 50% less quasispecies, preferably at least about 70% less quasispecies, more preferably at least about 80% less quasispecies, even more preferably at least about 90% less quasispecies and most preferably about 100% less quasispecies than the number of quasispecies generated by a conventional vaccine. Such homeogenous live attenuated CHIKV generated from i-DNA™ plasmid can be configured into a pharmaceutically acceptable formulation suitable for vaccine administration to people. Alternatively, the i-DNA™ can be administered to people in a pharmaceutically acceptable way as shown, for example, in FIG. 2.

A similar system has been developed for flaviviruses, for example West Nile virus (for example, U.S. Pat. No. 7,459,163, incorporated herein by reference in its entirety). An i-DNA™ vaccine for Venezuelan equine encephalitis (VEE) virus, another alphavirus is described in commonly-owned International Application No. PCT/US2009/004133, incorporated herein by reference in its entirety. However, until now, there has been no i-DNA™ vaccine system for CHIKV. The difficulty is in the configuring CHIKV i-DNA™ to combine several characteristics that are normally not present in a CHIKV virus during its normal life cycle.

In exemplary embodiments, CHIKV i-DNA™ plasmid is efficiently grown as a high-copy plasmid in bacteria (which are not a normal host for CHIKV) and, therefore i-DNA™ is preferably free of any strong secondary structures, cryptic origins of replication or open reading frames (ORFs) encoding toxic products or of any other known and unknown elements inhibiting growth of bacteria or synthesis of plasmid DNA.

In other exemplary embodiments, the genomic CHIKV RNA is efficiently transcribed in the host cell nuclei. Nucleoplasm in the nuclei normally represents a hostile environment (because of splicing and other RNA processing mechanisms) for RNAs that are evolved to replicate in the cytoplasm such as CHIKV RNA. After transcription, the resulting RNA is preferably able to avoid splicing machinery and also successfully migrate from the nucleus to the cytoplasm via nuclear pores, the process that is tightly controlled by the cellular proteins and factors. The RNA of cytoplasmic viruses such as CHIKV do not normally have elements that ensure synthesis and transport of intact full-length RNA in the nucleus. Therefore, the i-DNA™ should preferably be free of cryptic splice sites or other elements precluding effective transcription and transport of RNA into the cytoplasm.

In other exemplary embodiments, in order to replicate in the cytoplasm and generate a live attenuated vaccine, the transcribed RNA should be functional and have authentic 5' and 3' ends capable of supporting RNA replication.

In further exemplary embodiments, in order to ensure synthesis and transport from the nucleus to cytoplasm of transcribed CHIKV RNA, certain sequences can be either removed or introduced into CHIKV i-DNA™.

Herein are described examples of several configurations of CHIKV i-DNA™ that can be used to generate live attenuated CHIKV in vitro or in vivo and can be configured into pharmaceutically-acceptable chikungunya vaccines. The CHIKV i-DNA™ vaccines described herein are also expected to protect against O'nyong'nyong virus, a related alphavirus. Accordingly, i-DNA™ vaccines described herein could also be used in a method for immunizing a mammal against the O'nyong'nyong virus, which would include administering an exemplary vaccine to the mammal.

EXAMPLES

Example 1

Live attenuated vaccine candidate CHIK 181/25 (TSI-GSD-218) was generated from CHIKV strain 15561 and later successfully tested in phase II clinical trials (Edelman et al., 2000; Levitt et al., 1986). However, CHIKV 181/25 strain has common drawbacks with other live vaccines. For example, there is the risk of reversion to a virulent form, which has been shown previously (Parker, 1994). In addition to safety risks associated with the possibility of genetic reversion, other weaknesses include heterogeneity of virus population within the vaccine, presence of impurities and adventitious agents derived from cells substrate and during vaccine preparation; costly and inconvenient requirement for a cold chain delivery, difficulties in production of large amounts of live attenuated virus, and the requirement of constant quality control measures to maintain the attenuated genotype unchanged.

An i-DNA™ molecule contains the full-length cDNA copy of the 181/25 genomic RNA under control of the CMV promoter (FIG. 3). The distance between the promoter and the start of CHIKV cDNA (15±2 nucleotides according to our numbering, see nucleotide sequence on FIG. 3 for details) ensures generation of genomic CHIKV RNA with functional 5' terminus capable of RNA amplification and replication. The polyA tail, ribozyme sequence and the transcription termination sequences ensure generation of CHIKV RNA with functional 3' terminus. The entire DNA fragment shown on FIG. 3 includes (1) CMV promoter/enhancer sequences, (2) the full-length CHIKV cDNA, (3) polyA tail, (4) ribozyme, and (5) transcription termination sequences. Such DNA fragment can be cloned and propagated in *E. coli* as a part of plasmids known in the art including but not limited to pcDNA3.1, pCR2.1, pUC19 and others. Following transcription from i-DNA™ shown in FIG. 3, the genomic RNA of live attenuated vaccine is generated in vivo, which initiates limited replication of live attenuated vaccine virus and generation of a protective immune response (FIG. 2).

In addition to mutations contained in the live attenuated virus strain 181/25 of CHIKV, other configurations of attenuating mutations can be used for the development of CHIKV i-DNA™ vaccines. Additional sequence variations including deletions, insertions or substitutions can be used to improve characteristics of CHIKV i-DNA™.

Figure 10A:
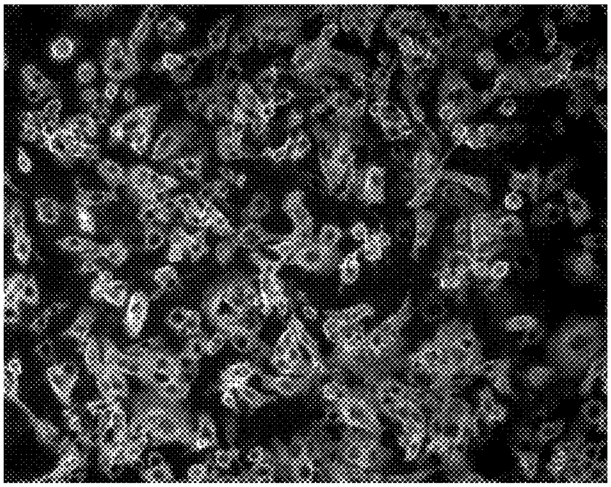
FIG. 10 (A-C) illustrates example photomicrographs of Chinese hamster ovary (CHO) cells transfected with the Full-Length CHIKV i-DNA™, clone #10 (sequence of FIG. 4), by immunofluorescence assay using specific anti-CHIKV antibody at 48 hr post transfection.
Figure 10B:
Figure 10C:
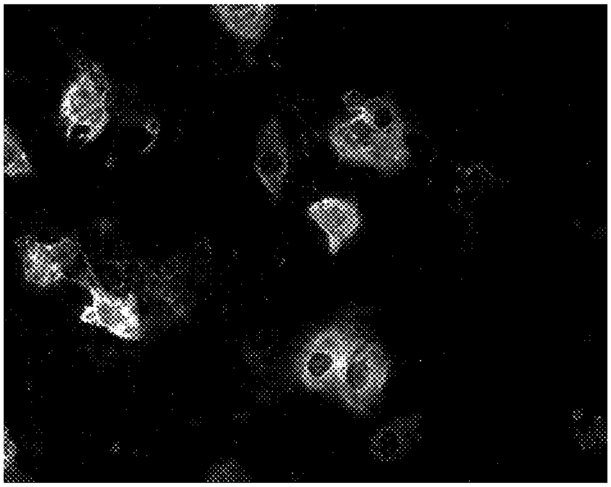

FIG. 4 shows the nucleotide sequence of a variant i-DNA™ that is similar to that shown on FIG. 3 but containing no ribozyme sequences. Surprisingly, such an i-DNA™ without a ribozyme is capable of transcribing the functional infectious CHIKV RNA and generating live attenuated CHIKV virus. FIG. 10 demonstrates that transfection of Chinese hamster ovary (CHO) cells with i-DNA™ plasmid (clone #10, either in supercoiled form or linearized by using NotI enzyme) results in expression of CHIKV antigens in the majority of CHO cells suggesting that (i) no cryptic splicing sites or other restrictive elements were present in the i-DNA™ or encoded RNA and (ii) that transfection results in live virus, which ensures effective spread of antigen expression in transfected CHO cells. Further, i-DNA™ can accommodate additional sequences that can improve certain characteristics of i-DNA™ vaccines. Examples of such i-DNA™ sequences are shown on FIGS. 5 and 6.

Also, chimeric live attenuated alphavirus protecting against CHIKV and O'nyong'nyong virus can be made by placing CHIKV structural genes in place of another alphavirus structural genes. FIG. 7 shows an example of a nucleotide sequence, in which CHIKV structural genes derived from strain 181/25 are introduced into TC-83 live attenuated virus in place of the TC-83 structural genes. Again, such vaccine can either (1) represent homogenous virus generated from i-DNA™ in vitro in a pharmaceutically acceptable way, or (2) represent the i-DNA™ construct formulated in a pharmaceutically acceptable way for administration in vivo.

Alternatively, chimeric vaccines against alphaviruses can be made by introducing structural proteins from other alphaviruses into CHIKV i-DNA. FIG. 9 shows an example of a nucleotide sequence of a chimeric CHIKV i-DNA™ containing the structural polyprotein from TC-83 virus in place of the structural polyprotein of CHIKV 181/25 virus. Such chimeric i-DNA™ can be used for production of either homogenous virus vaccines or i-DNA™ vaccines against VEE infections.

Example 2

Generation of Live Attenuated CHIKV In Vitro Using i-DNA

Figure 11A:
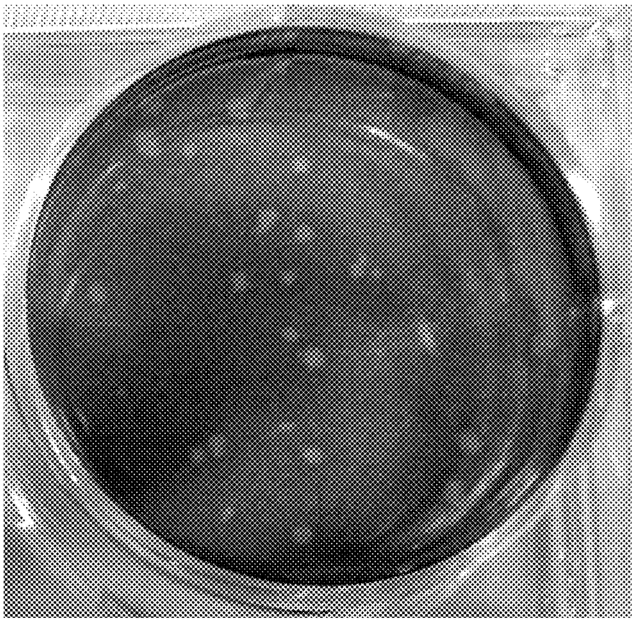
FIG. 11 illustrates (A) determination of the titer and plaque morphology of live attenuated virus derived from i-DNA, clone #10, FIG. 4; and, (B) plaques derived from 181/25 IND vaccine that was passed once in CHO cells. The i-DNA™-derived CHIKV Virus has a uniform plaque size as compared to “classic” IND Vaccine 181/25.

When CHIKV i-DNA™ molecule (FIGS. 3-9) is introduced into cells in vitro, for example by transfection, the CHIKV viral RNA is generated in the cells. The resulting RNA is "infectious" and initiates production of the CHIKV live attenuated virus vaccine in the cells (FIG. 10). The live attenuated CHIKV accumulates in the culture medium and can be harvested and the titer of live attenuated virus and plaque morphology can be determined by plaque assay (FIG. 11A). The live attenuated CHIKV can be formulated in a pharmaceutically acceptable way according to current state of the art.

Example 3

Vaccination In Vivo with Live Attenuated CHIKV Vaccine Generated from i-DNA™ In Vitro CHIKV virus vaccine can be harvested from cultured cells as described in Example 2 and used in a pharmaceutically acceptable formulation for vaccination of animals or people according to current state of the art. Administration can be by any route typically used for vaccination, including subcutaneous, intravenous, intramuscular, combinations thereof and the like. An advantage of vaccine that is generated from the i-DNA™ is that it represents homogeneous progeny virus generated from the same, well-characterized, stable DNA.

Figure 11B:
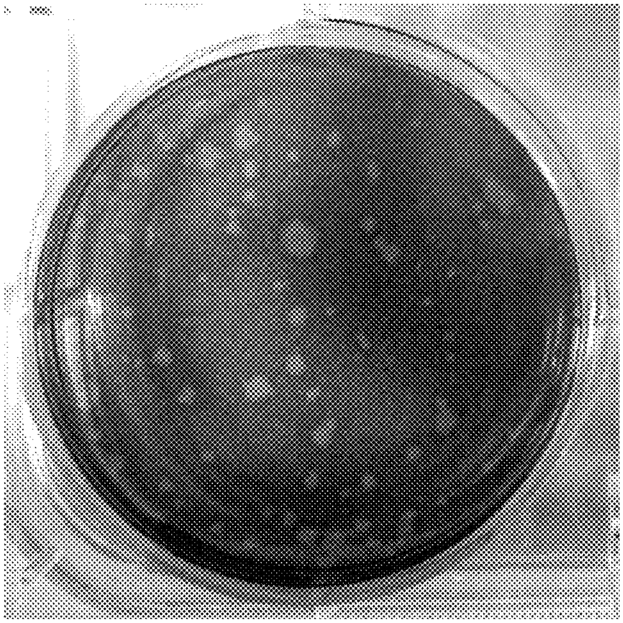

FIG. 11 shows plaque size homogeneity for i-DNA™-derived virus (FIG. 11A) as compared to the more heterogenous plaque sizes in a "classic" 181/25 IND vaccine (FIG. 11B). Homogenous plaque size is expected to result in higher safety of i-DNA-derived live attenuated virus because large plaques in 181/25 IND vaccine (FIG. 11B) can indicate presence of revertants to virulent virus. Revertants to virulent virus are detected in the virus isolated from patients that experience adverse effects after vaccination with 181/25 IND vaccine (Genbank entry EF452494, note isolation source="viremic vaccine recipient").

FIG. 12 shows sequencing results of several clones generated from 181/25 IND vaccine by reverse transcription and PCR. Vaccine 181/25 was passed once in CHO cells, the RNA isolated and Reverse Transcription PCR (RT-PCR) conducted. The RT-PCR fragments were cloned and sequenced.

The cDNA fragments were sequenced and compared to the sequences of several virulent CHIKV strains from GenBank as well as to the original 181/25 sequence. Analysis revealed that several sequenced clones contain "reversion" mutations to the virulent virus. The result shown in FIG. 12 is that in the sequenced region, one out of seven clones has the same sequence as 181/25 IND vaccine, whereas others had nucleotide substitutions present in virulent isolates. Only clone 3.5_40 out of seven has an isoleucine (I) residue at amino acid 301, as in 181/25, whereas other six clones have the threonine (T) residue that is present in the virulent wild type CHIKV isolates and in the VR1 isolate from 181/25-vaccinated sick patient. Heterogeneity was also detected at position 314.

The vaccines described herein can provide higher safety and regulatory advantages. Because the same, clonally purified, i-DNA™ can be used for the production of different vaccine lots, these vaccine will have greater uniformity and lot-to-lot consistency compared to current vaccines, which can accumulate mutations during virus passages.

Example 4

Vaccination In Vivo by Using i-DNA™ Vaccine

Alternatively, CHIKV i-DNA™ (FIGS. 3-8) can be administered in a pharmaceutically-acceptable formulation into the vaccine recipient directly, for example intramuscularly or intravenously, as illustrated in FIG. 2. Direct i-DNA™ administration to the vaccine recipient initiates production of CHIKV vaccine in the tissues of the patient in vivo, and provides successful vaccination against chikungunya. An additional advantage of i-DNA™ immunization versus conventional live attenuated virus vaccine stems from the immunogenic characteristics of the i-DNA™ itself. Bacterially produced DNA, including i-DNA™, contains unmethylated CpG motifs. These motifs activate toll-like receptor (TLR) signaling pathway, which results in induction of innate immunity and production of pro-inflammatory cytokines and type 1 interferons (IFN 1) shortly after DNA injection. Signaling through receptors induces robust cytokine response from myeloid DCs and IFN 1 production from plasmocytoid DCs as well as stimulates cross-presentation of exogenous antigens and CTL T responses. Thus, i-DNA™ immunization leads to activation and maturation of DCs even before virus particles are released. Such pre-activated DCs enhance specific immune responses induced by newly synthesized live attenuated virus.

Example 5 i-DNA™ Vaccines with De-Optimized Codons

One vaccine, i-DNAC, contains the full-length cDNA copy of the 181/25 IND vaccine RNA genome but translational codons within the capsid gene are de-optimized via down-selected codons. Another vaccine, i-DNAE2-E1, also contains the full-length cDNA copy of the 181/25 IND vaccine RNA genome but translational codons within the E2-E1 gene region are similarly de-optimized. E1, E2 and C genes are selected based on immunogenicity of these antigens in mice and on the current knowledge about adaptive immune responses following CHIKV infection in humans. The de-optimized codons change only the nucleotide sequence and do not give rise to changes in the amino acid sequence. These silent mutations increase genetic stability and preserve the attenuated phenotype and are designed so that at least two independent genetic mutations are necessary for each codon to revert to a wild-type CHIKV codon.

The synthetic 181/25 fragment encompassing 3,771 base pairs of 181/25 structural gene region 7567-11313 (C-E1-E2) is synthesized biochemically (GenScript, Piscataway, N.J.). The recombinant 181/25 i-DNA, i-DNAC and i-DNAE2-E1 constructs are transfected into CHO-K1 cells in vitro. Samples of live attenuated viruses are collected from culture medium and cells at 6 hour intervals for 96 hours. The live CHIKV viruses produced via transfection of cells and phenotypic features of these recovered viruses are evaluated in vitro, examining kinetic parameters of replication in tissue culture, antigenic properties, genetic stability, and molecular heterogeneity by the following in vitro assays: (1) plaque assay and phenotype; (2) virus growth curves; (3) western blot; (4) immunofluorescence; (5) at least 10 passages in *E. coli*; (6) reverse transcription PCR, and (7) DNA sequencing of the entire structural region of at least 120 plaque isolates derived from each virus including 181/25 control (to assess population heterogeneity and genetic stability in mammalian cells). The ability of new CHIKV vaccine antigens to react with human antisera from recent CHIKV clinical cases is evaluated via ELISA.

Example 6

Animal Model Testing of i-DNA™ Vaccine

Production of plasmid i-DNA™ from *E. coli* is done using established methods for production of the bacterial cell bank, fermentation, harvest/lysis of the biomass, and downstream DNA purification. This process results in a sterile DNA product with about 95% supercoiled DNA and an A260/A280 ratio of about 1.9, as well as minimal residual endotoxin, RNA, genomic DNA, and protein impurities. Quality control includes (1) endotoxin testing, (2) agarose gel, (3) SDS-PAGE; (4) restriction enzyme analysis and (5) DNA sequencing. A maximum of 100 ng of i-DNA™ is injected intramuscularly (i.m.) into: (1) newborn ICR mice; (2) 14-day-old CD-1 mice; (3) aged (3-month-old) CD-1 mice; and (4) immunosuppressed hamsters.

Alternatively, i-DNA™ is delivered into the quadriceps muscles by in vivo electroporation in a total volume of 0.1 ml using the BTX ECM600 with 2-needle Array Electrode (BTX/Harvard Apparatus, Holliston, Mass.). The PolyPlus InVivo-Jet PEI transfection reagent (PolyPlus, Illkirch, France) can be used as another transfection method. Safety and immunogenicity parameters include (1) viremia; (2) morbidity; (3) cytokine profiles; (4) CHIKV ELISA; (5) virus-specific neutralizing antibody responses; (6) cell-mediated immunity; and (7) anti-DNA™ antibody.

For the ICR and CD-1 mice, sixty animals from each strain are divided into 5 groups (12 mice per group): (1) 181/25 i-DNA; (2) i-DNAC; (3) i-DNAE2-E1; (4) 181/25 virus (positive control); and (5) mock-vaccinated (negative control). Each i-DNA™ plasmid is injected as a single 100 ng dose in 20-40 μl i.m. Control animals are injected with 105 PFU of 181/25 virus vaccine. Blood samples are taken every 2-7 days for viremia and serology. At days 0, 2, 4, 8, and 16 after immunization, 3 mice from each group are euthanized and bled by cardiac puncture. TLR9 activation by i-DNA™ is expected to trigger pro-inflammatory cytokine production at 12-16 h, shortly before the release of the infectious virus, thus enhancing adaptive immune responses. Innate immunity is tested by cytokine ELISA at different time points after i-DNA™ immunization by using reagents for IFN-γ, IL-1α/β, TNF-α, MCP-1, IL-4, IL-6 and IL-12p40 (BD Biosciences, San Jose, Calif.). INF-α and INF-β is measured by ELISA (PBL Biomed Labs, NJ). The levels of biological active IFN are determined using an EMCV-L929 bioassay (Daffis et al., 2007). Specific immune responses are measured by IgG ELISA, plaque reduction neutralization assay (PRNT), and by IFN-γ ELISPOT assay using pools of 15-mer peptides overlapping by 11 amino acids (Mimotopes, Melbourne, Australia) (Muthumani et al., 2008). Briefly, ELISPOT plates are coated with anti-IFN-γ Ab and incubated for 12 h at 40 C. Plates are washed and blocked with 1% BSA.

After washing, 25×104 splenocytes are added to wells in triplets and stimulated overnight by incubation with specific E1-, E2-, and C-derived peptide pools at 37° C. After stimulation, the cells are washed and incubated with biotinylated anti-mouse IFN-γ (R&D Systems). Tissue samples (liver, spleen, lymph nodes, lung, kidney, and brain) are homogenized in PBS with 1% FBS and used for plaque assay or RNA extraction with Trizol.

Cyclophosphamide (CYP) treated Syrian golden hamsters (*Mesocricetus auratus*) (Harlan Sprague Dawley) are used to evaluate safety and immunogenicity of vaccines in the immunocompromised conditions (Mateo et al., 2007). A total of 26 hamsters are used in this study. The CYP-treated animals are divided into six groups. Three groups receive the original and modified i-DNAs. The three control groups include a group that receives the 181/25 vaccine; a control group that receives the CYP treatment but no vaccine, and a control group that receives no CYP and no vaccine (Vertebrate Animals). The i-DNA™ constructs are injected i.m. as a single dose (100 ng). The 181/25 control virus is injected in 100 μl (105 PFU). Animals are examined daily for 8 weeks (end-point) for any evidence of adverse effects. Temperature and body weight is recorded. Animals are bled every 2 days for the 1st week, then every 7 days for virus detection and serology.

REFERENCES

Each of the below references is incorporated herein by reference in its entirety.

Daffis S, Samuel M A, Keller B C, Gale M Jr, Diamond M S. Cell-specific IRF-3 responses protect against West Nile virus infection by interferon-dependent and -independent mechanisms. PLoS Pathog. 2007 Jul. 27; 3(7):e106.

Edelman, R., C. O. Tacket, S. S. Wasserman, S. A. Bodison, J. G. Perry, and J. A. Mangiafico, 2000b, Phase II safety and immunogenicity study of live chikungunya virus vaccine TSI-GSD-218: Am. J. Trop. Med. Hyg., v. 62, p. 681-685.

Khan, A. H., K. Morita, C. Parquet Md Mdel, F. Hasebe, E. G. Mathenge, and A. Igarashi, 2002, Complete nucleotide sequence of chikungunya virus and evidence for an internal polyadenylation site: J Gen Virol, v. 83, p. 3075-84.

Kitaoka, M., 1967, Japanese encephalitis vaccine including a preliminary report on dengue fever and Chikungunya vaccines: Jpn J Med Sci Biol, v. 20 Suppl, p. 41-56.

Levitt, N. H., H. H. Ramsburg, S. E. Hasty, P. M. Repik, F. E. Cole, Jr., and H. W. Lupton, 1986, Development of an attenuated strain of chikungunya virus for use in vaccine production: Vaccine, v. 4, p. 157-62.

Mateo R I, Xiao S Y, Travassos da Rosa A P, Lei H, Guzman H, Lu L, Tesh R B. Yellow fever 17-D vaccine is neurotropic and produces encephalitis in immunosuppressed hamsters. Am J Trop Med Hyg. 2007 November; 77(5):919-24.

Muthumani K, Lankaraman K M, Laddy D J, Sundaram S G, Chung C W, et al. Immunogenicity of novel consensus-based DNA vaccines against Chikungunya virus. Vaccine. 2008; 26:5128-5134.

Powers, A., and A. Brault, 2009, O'nyong-nyog and chikungunya, p. 589-607. in: Vaccines for biodefense and emerging and neglected diseases; edited by Alan D. T. Barrett and Lawrence R. Stanberry. Academic Press, Elsevier, Amsterdam, London, San Diego.

Parker, M. D., 1994, Structural protein gene sequences of Chikungunya vaccine virus, its parent and a virulent revertant, Virology Division, USAMRIID, Fort Detrick, Frederick, Md. 21701, USA. GenBank Accession No. L37661.

Wang, E., E. Volkova, A. P. Adams, N. Forrester, S. Y. Xiao, I. Frolov, and S. C. Weaver, 2008, Chimeric alphavirus vaccine candidates for chikungunya: Vaccine, v. 26, p. 5030-9.

Yamshchikov, V. Infectious DNA as a vaccine against West Nile and other flaviviruses. U.S. Pat. No. 7,459,163

The invention claimed is:

1. A vector comprising:

(a) DNA encoding an infectious RNA molecule; and (b) a eukaryotic RNA polymerase promoter;

wherein:

(i) the DNA encoding an infectious RNA molecule is operably linked to the eukaryotic RNA polymerase promoter; and (ii) the infectious RNA molecule encodes a chikungunya virus (CHIKV).

2. The vector of claim 1, wherein the infectious RNA molecule encodes a non-pathogenic CHIKV.

3. The vector of claim 1, wherein:

the eukaryotic RNA polymerase promoter comprises a cytomegalovirus (CMV) RNA polymerase promoter, the CMV RNA polymerase promoter is located from about 13 to about 17 nucleotide residues upstream of the 5' end of the DNA encoding an infectious RNA molecule, and the infectious RNA molecule encodes an attenuated CHIKV virus.

4. The vector of claim 1, wherein the CHIKV is a chimeric virus containing sequences from CHIKV as well as from another alphavirus.

5. The vector of claim 1, wherein the vector, comprises sequences that allow transport of the transcribed infectious RNA molecule from nucleus to cytoplasm or that allow generation of transcribed infectious RNA molecule comprising functional 5' and 3' termini for replication and amplification.

6. A vector comprising:

(a) DNA encoding an infectious RNA molecule; and (b) a eukaryotic RNA polymerase promoter;

wherein:

(i) the DNA encoding an infectious RNA molecule is operably linked to the eukaryotic RNA polymerase promoter; and (ii) the infectious RNA molecule encodes an alphavirus and contains sequences from CHIKV as well as from another alphavirus.

7. The vector of claim 6, comprising the DNA sequence listed in SEQ ID NO: 6.

8. A vaccine comprising the vector of claim 7.

9. A method for immunizing a mammal against a CHIKV, wherein the method comprises administering to the mammal an effective amount of the vaccine of claim 8.

10. A vaccine comprising an infectious virus isolated from cells transfected with the vector of claim 7.

11. A vector comprising a sequence selected from the group consisting of SEQ ID NO: 1, SEQ ID NO: 2, SEQ ID NO: 3, SEQ ID NO: 4, and SEQ ID NO: 5.

12. A homogenous clonally purified live attenuated CHIKV population prepared from cultured cells transfected with the vector of claim 11.

13. A vaccine comprising the live attenuated virus of claim 12.

14. A method for immunizing a mammal against a CHIKV, wherein the method comprises administering to the mammal an effective amount of the vaccine of claim 13.

15. The vector of claim 1, wherein the infectious RNA molecule encodes an attenuated CHIKV.

16. A method of preparing a vaccine for immunizing a mammal against a CHIKV, wherein the method comprises transfecting the vector of claim 15 into a eukaryotic cell and isolating homogeneous clonally pure infectious viruses from a culture medium comprising the transfected eukaryotic cell, thereby obtaining a vaccine.

17. A vaccine comprising the vector of claim 15.

18. A method for immunizing a mammal against a CHIKV, wherein the method comprises administering to the mammal an effective amount of the vaccine of claim 17.

19. The vector of claim 6, wherein the infectious RNA molecule encodes an attenuated alphavirus and contains sequences from an attenuated CHIKV.

20. A vaccine comprising the vector of claim 19.

21. A method for immunizing a mammal against a CHIKV, wherein the method comprises administering to the mammal an effective amount of the vaccine of claim 20.

22. An isolated transfected eukaryotic cell comprising the vector of claim 1.

23. An isolated transfected eukaryotic cell of claim 22, wherein the infectious RNA molecule encodes an attenuated CHIKV.

24. An isolated transfected eukaryotic cell comprising the vector of claim 6.

25. An isolated transfected eukaryotic cell of claim 24, wherein the infectious RNA molecule encodes an attenuated alphavirus and contains sequences from an attenuated CHIKV.

26. A method of immunizing a mammal against a CHIKV, wherein the method comprises administering to the mammal an effective amount of the vaccine of claim 10.

27. A vaccine comprising the vector of claim 11.

28. A method of immunizing a mammal against a CHIKV, wherein the method comprises administering to the mammal an effective amount of the vaccine of claim 27.

29. A method of immunizing a mammal against a CHIKV, wherein the method comprises administering to the mammal an effective amount of the vector of claim 15.

30. A method of immunizing a mammal against a CHIKV, wherein the method comprises administering to the mammal an effective amount of the vector of claim 19.

* * * * *